US005994143A

United States Patent [19]
Bieniarz et al.

[11] Patent Number: 5,994,143
[45] Date of Patent: *Nov. 30, 1999

[54] POLYMERIC FLUOROPHORES ENHANCED BY MOIETIES PROVIDING A HYDROPHOBIC AND CONFORMATIONALLY RESTRICTIVE MICROENVIRONMENT

[75] Inventors: Christopher Bieniarz, Highland Park; Jeffrey B. Huff, Park Ridge; Michael J. Cornwell, Morton Grove; Seshagiri R. Tata Venkata, Chicago, all of Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/595,092

[22] Filed: Feb. 1, 1996

[51] Int. Cl.$^6$ .................. G01N 33/00; G01N 33/533; C09B 5/00
[52] U.S. Cl. .................. 436/91; 436/92; 436/546; 436/106; 436/119; 436/800; 8/648; 548/100; 548/416; 548/452; 548/469; 548/471; 548/513; 549/1; 549/6; 549/7
[58] Field of Search .................. 435/7.21; 525/54.1; 436/539, 546, 106, 119, 800, 91, 92; 424/193.1; 8/648; 548/100, 416, 452, 469, 471, 513; 546/1; 549/1, 6, 7

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 5,002,883 | 3/1991 | Bieniarz et al. | 435/176 |
| 5,030,697 | 7/1991 | Hugl et al. | 525/326.9 |
| 5,298,583 | 3/1994 | Heiliger et al. | 526/286 |
| 5,401,469 | 3/1995 | Kobayashi et al. | 422/82.07 |
| 5,401,847 | 3/1995 | Glazer et al. | 546/107 |

FOREIGN PATENT DOCUMENTS

| | | |
|---|---|---|
| 320308 | 6/1989 | European Pat. Off. .......... C23Q 1/68 |
| 0361229 | 4/1990 | European Pat. Off. . |
| 439182 | 7/1991 | European Pat. Off. .......... C12Q 1/68 |
| 0513560 | 11/1992 | European Pat. Off. . |
| 8605505 | 9/1986 | WIPO . |
| 9220746 | 11/1992 | WIPO . |
| 9502700 | 1/1995 | WIPO .............. C12Q 1/00 |

OTHER PUBLICATIONS

B. Dietrich, "Coordination Chemistry of Alkali and Alkaline–Earth Cations with Macrocyclic Ligands" *J. Chem. Ed.* 62 No. 11 (1985) 954–964.
D.J. Cram, K.N. Trueblook, "Concept, Structure, and Binding in Complexation", *Top. Curr. Chem.* 98 (1981) 43–106.
B. Xu and T. Swager, "Host–Guest Mesomorphism: Cooperative Stabilization of a Bowlic Columnar Phase", *J. Am. Chem. Soc.* 1995, 117, 5011–5012.
J. Rebek, Jr., "Binding Forces, Equilibria, and Rates: New Models for Enzymic Catalysis", *Acc. Chem. Res.* (1984) vol. 17, 258–264.
J. Rebek, Jr., "Model Studies in Molecular Recognition", *Science* 235 (1987) 1478–1484.

W.L. Mock, N.–Y.Shih, "Host–Guest Binding Capacity of Cucurbituril", *J. Org. Chem.*, 1983, 48 (20) 3618–3619.
F. Diederich, et al., "2,2'7,7'–Tetrahydroxy–1,1'–binaphthyl: a Versatile Chiral Spacer for Novel Mono–and Ditopic Cyclophane Hosts with Apolar Binding Sites", *Angew Chem. Int. Ed. Engl.* (1988) vol. 27, No. 12, 1705–1711.
D.B. Dess, et al., "Readily Accessible 12–I–g$^1$ OXidant for the Conversion of PRimary and Secondary Alcohols to Aldehydes and Ketones", *J. ORg. Chem.*, 1983, 48 (1983) 4155–4156.
L.D. Melton, et al., "Synthesis of Monosubstituted Cyclohexaamyloses", *Carbohydrate Research*, 18, 1971, 29–37.
R.C. Petter, et al., "Cooperative Binding by Aggregated Mono–6–(alkylamino)–β–cyclodextrins", *J. Am. Chem. Soc.*, 1990, 112, 3860–3868.
M. Fiore, et al., "The Abbott Imx™ Automated Benchtop Immunochemistry Analyzer System", *Clin. Chem.*, 1988, 34/9 1726–1732.
J.B. Huff, C. Bieniarz, "Synthesis and Reactivity of 6–β–Cyclodextrin Monoaldehyde: An Electrophilic Cyclodextrin for the Derivatization of Macromolecules under Mild Conditions", *J. Org. Chem.*, 1994, 59, 7511–7516.
J.K. Poudrier, "Corn Meets Nanotechnology and They're Getting Along 'Amaizeingly' Well", *Today's Chemist at Work*, Feb. 1995, 25–30.
L.J. Ong, A.N. Glazer, "Crosslinking of allophycocyanin", *Physiol. Veg.*, 1985, 23 (1), 777–787.
A. Chigir et al., "Polymeric Analogs of Polymethine Dyes", *Chemical Abstracts*, vol. 71, No. 16, (1969).
Anthony C. Stevens et al., "Synthesis of Protein–Reactive (Aminostyryl)pyridinium Dyes", *Bioconjugate Chem.*, 1993, 4, 19–24.
J.–M. Lehn, "Design of Organic Complexing Agents. Strategies towards Properties", *Struct. Bonding* (Berlin) 16 (1973) 1–69.
J.–M. Lehn, "Cryptates: The Chemistry of Macropolycyclic Inclusion Complexes", *Acc. Chem. Res.* 11 (1978) 49–57.
P.G. Potvin, J.–M. Lehn in R.M. Izatt, J.J. Christensen (Eds.): Synthesis of Macrocycles: The Design of Selective Complexing Agents (*Progress in Macrocycle Chemistry*, vol. 3), Wiley, New York 1987, p. 167.
D.J. Cram, "Preorganization—From Solvents to Spherands", *Angew. Chem. Int. Ed. Engl.*, 25 (1986) 1039–1057).
Ph. Hebert et al., J. Photochem. Photobiol. A: Chem., vol. 84., pp. 45–55., 1994.

*Primary Examiner*—Keith D. MacMillan
*Assistant Examiner*—P. Ponnalun
*Attorney, Agent, or Firm*—David L. Weinstein

[57] ABSTRACT

Fluorescent conjugates suitable for use in flow cytometry and other biological applications. The fluorescent conjugates comprise an antibody having a polymeric dye bound thereto. The polymeric dye is preferably enhanced by a hydrophobic and conformationally restrictive moiety either bound thereto or in close association therewith. The hydrophobic and conformationally restrictive moiety is preferably derived from a cyclodextrin. The polymeric dye comprises a polymeric entity having signal-generating groups, such as aminostyryl pyridinium dye residues attached thereto. The fluorescent conjugates exhibit exceptional stability characteristics and avoid many of the problems of energy transfer, bio-conjugability, and solubility.

4 Claims, 17 Drawing Sheets

POLYMERIC FLUOROPHORES ENHANCED BY MOIETIES PROVIDING A HYDROPHOBIC AND CONFORMATIONALLY RESTRICTIVE MICROENVIRONMENT

BACKGROUND OF THE INVENTION

1. Field of the Invention

The invention relates to fluorescent dyes that are useful in various assays and, more particularly, to fluorescent polymeric dyes, wherein fluorescence is enhanced by at least partially hosting fluorophoric moieties with moieties providing a hydrophobic and conformationally restrictive microenvironment.

2. Discussion of the Art

A variety of assay techniques are employed in quantitative and qualitative analysis of chemical and biochemical mixtures. One assay technique, referred to as "fluorescence", is useful in many biochemical studies. This assay technique utilizes a fluorescent chemical to label certain molecules to distinguish those molecules from unlabeled, but similar, molecules. A chemical is considered to be fluorescent if it absorbs light at a given wavelength (the "excitation" wavelength) and emits light at a longer wavelength (the "emission" wavelength). The fluorescent chemicals used in this type of assay are often referred to as fluorescent dyes.

There are numerous optical techniques for detecting fluorescent dyes employed in fluorescence assays. One such technique is flow cytometry. Flow cytometry is employed in fluorescence assays to identify particular molecules or cells and to separate or distinguish those molecules or cells from a mixture. In a typical flow cytometry procedure, a fluorescent dye is linked to an antibody. The antibody is specific to an antigen of a particular molecule or a cell-surface molecule of a particular cell desired to be detected. The linking of the antibody and fluorescent dye is referred to as "conjugation", and the linked antibody-fluorescent dye complex is referred to as a "conjugate".

After an appropriate antibody and an appropriate dye are linked to form a conjugate, the conjugate is added to a mixture suspected of containing the antigen or cell-surface molecule sought to be detected. When the conjugate is added to the mixture and appropriate conditions are maintained, the antibody of the conjugate binds with the antigen or cell-surface molecule. The entire mixture in which the antigen or cell-surface molecule is contained and to which the conjugate was added is then subjected to a laser beam of the excitation wavelength for the particular fluorescent dye. The laser beam of this wavelength causes the molecules or cells that contain the bound antibody-fluorescent dye conjugate to fluoresce. A flow cytometer may detect and measure the amount of laser light scattered by the bound molecule or cell, and by that measurement, the quantity, quality, and other determinations relating to the detected antigen or cell-surface molecule may be made.

It has typically been necessary to take steps to increase the intensity of the fluorescent dyes for better detection. Several means have been employed to increase the intensity. However, there are significant limitations that reduce the effectiveness of those means.

One means for increasing the intensity of fluorescent dyes at a given wavelength has been the mechanism of fluorescence energy transfer, whereby a transfer of energy from an excited state is made from a donor molecule to an acceptor molecule. The transfer is usually accomplished by positioning one fluorophore close to another fluorophore. As used herein, the expression "fluorophore" means a carrier of fluorescence.

The first of the closely-positioned fluorophores may be excited by light of a given wavelength. Then, instead of emitting light of a longer wavelength, the excited fluorophore transfers energy to the second fluorophore. That transferred energy excites the second fluorophore, which then emits light of an even longer wavelength than would have been emitted by the first fluorophore. An example of such an energy transfer arrangement involves phycobiliprotein-cyanine dye conjugates. Subjecting these conjugates to an about 488 nm laser light excites the phycobiliprotein. The phycobiliprotein will then, without itself irradiating, transfer energy to the cyanine fluorophore at the excitation wavelength of the cyanine, which is coincident with the emission wavelength of the phycobiliprotein, about 580 nm. Consequently, the cyanine fluorophore is thereby excited and subsequently emits light of its emission wavelength of about 680 nm. This type of energy transfer system in often referred to as a "tandem energy transfer system."

Energy transfer is not a very simple means for increasing fluorescence for a number of reasons. Two fundamental requirements in energy transfer are an appropriate relative spatial distance relationship of the donor and acceptor molecules and an appropriate relative angular relationship of the absorption and emission dipoles of the two molecules. Obtaining and maintaining these fundamental relationships is extremely difficult, if not impossible, in many circumstances. Additionally, there are many other requirements, including overlap of the emission spectrum of the donor with the absorption spectrum of the acceptor, stability of the fluorophores, change in fluorescent characteristics upon conjugation, quantum efficiency of the transfer, non-specific binding of the fluorophores to other compounds, and others. Eliminating the need for meeting these requirements would be an improvement in the art.

Another means for increasing fluorescent intensity of fluorescent dyes is to attach a multiplicity of fluorophores to a polymer and attach the polymer to an antibody. In this arrangement, each of the fluorophores attached to the polymer may be excited by a laser light and emit light at its emission wavelength. However, the use of polymers for this purpose has generally not been effective. The primary problem encountered with polymers is that when a multiplicity of fluorophores are randomly placed on a single polymer, signal quenching among the fluorophores results. Further, even if the polymer/antibody conjugate emits a greater cumulative quantity of light due to the multiplicity of fluorophores, the emission wavelength is only that applicable to the particular fluorophores. Fluorophores of the prior art have had a limited range of wavelength variation between excitation wavelength and emission wavelength. It would be desirable to provide both a polymer to which may be attached a multiplicity of fluorophores without quenching and a fluorescent dye that emits light of a wavelength much greater than the excitation wavelength. Such a polymeric arrangement and wavelength range would enable more accurate detection.

Yet another means for increasing the intensity of fluorescent dyes involves the use of cyclodextrins. Cyclodextrins are well known water soluble cyclic oligosaccharides having a hydrophobic central cavity and a hydrophilic peripheral region. Generally, the shape of a cyclodextrin molecule is substantially cylindrical, with one end of the cylinder having a larger opening than the other. The smaller opening is known as the primary rim, and the larger opening is known as the secondary rim. A cavity into which small molecules can enter through the larger secondary rim is present between the two openings of the cyclodextrin molecule and, in aqueous systems, this cavity of a cyclodextrin molecule provides a hydrophobic microenvironment for the complexing of hydrophobic molecules of low molecular weight. The cyclodextrin molecule acts as a host for the hydrophobic molecule of low molecular weight, i.e., the guest.

Efforts to generate polymeric cyclodextrins have been made in an attempt to increase the fluorescence associated with fluorophores. Theoretically, the complexing properties of a single cyclodextrin molecule can be magnified by having several cyclodextrin molecules in close proximity to each other, for the reason that having several cyclodextrin molecules in close proximity to each other increases the probability that a guest molecule will enter the cavity of a cyclodextrin molecule. According to the theory, if a polymeric cyclodextrin molecule were created, it would be capable of hosting a plurality of guest molecules. Further, if the guest molecules were signal-generating groups, there would be several fluorophores in close proximity to each other, and the fluorescence associated with the polymer would be greater than that of a single fluorophore. Hence, according to the theory, if a conjugate were made with a polymeric cyclodextrin containing a plurality of fluorophores, fluorescence of the polymer would be greater than that of a conjugate comprising a single fluorophore.

Several polymeric cyclodextrins have been manufactured to validate the above-described theory. However, those polymers suffer from problems that severely limit their effectiveness. The polymeric cyclodextrins are synthesized by using cyclodextrin monomers that have been modified to contain several reactive groups on the cyclodextrin monomer's primary and secondary rims, thereby allowing these monomers to react via their primary and secondary rims, and react multiple times via their multiple reactive groups. When a cyclodextrin molecule is bound by its secondary rim, the larger opening to the hydrophobic cavity is hindered. As a result, it is difficult for a guest molecule to enter the cavity of the cyclodextrin molecule, and the cyclodextrin's utility as a host is compromised. Further, polymers derived from cyclodextrin monomers having multiple reactive groups results in a high degree of cross-linking. When cross-linking occurs, not only are the cyclodextrin molecules bound by the secondary rims, causing the problems mentioned previously, but a matrix of cyclodextrins forms. Consequently, the number of cyclodextrin monomers polymerized is limited and many of the cyclodextrin monomers polymerized become buried within the matrix. Although many cyclodextrin molecules are in close proximity, very few of them have accessible secondary openings and very few guest/host complexes are able to form.

Another means for increasing intensity of fluorescent dyes is judicious selection of a suitable dye, among the many fluorescent dyes from which to choose. It has been common practice to employ naturally-occurring substances as fluorescent dyes for fluorescence testing. The more common naturally-occurring dyes include the phycobiliproteins, such as phycoerythrin, and others. As previously mentioned in connection with the discussion of energy transfer, phycobiliproteins are still being used in some tandem energy transfer systems. However, phycobiliproteins present certain problems in their use. A particular problem with phycobiliproteins is their instability. Exposure to light and other environmental effects can cause photo-bleaching, thereby adversely affecting fluorescence assays.

In recent years, a number of synthetic fluorescent dyes have been manufactured and employed for fluorescence assays. A well-known class of fluorescent dyes are the cyanine dyes. These dyes are polymethine dyes containing the —N—(C=C—C$\frac{}{n}$N—moiety.

Cyanine fluorescent dyes also present problems when employed in fluorescence biological testing procedures, such as flow cytometry. For example, many of these dyes are expensive to use and difficult to manufacture. Further, many of the cyanine dyes do not have a sufficiently large interval, i.e., Stokes' shift, between their excitation wavelength and their emission wavelength to be effective for fluorescence detection methods without utilizing energy transfer involving another fluorophore. Those dyes that do have a sufficiently large interval between excitation wavelength and emission wavelength are often sensitive to the environment.

Another class of fluorescent dyes that has been considered for use in biological testing procedures includes the aminostyryl pyridinium dyes. Because of environmental sensitivity, these dyes have been considered unsuitable for fluorescence labeling applications, such as flow cytometry. The environmental sensitivity of aminostyryl pyridinium dyes is well studied and described by Anthony C. Stevens et al., "Synthesis of Protein-Reactive (Aminostyryl) pyridinium Dyes", *Bioconjugate Chem.* 1993, 4, 19–24.

It would be desirable to develop a fluorescent dye whereby the need for energy transfer is eliminated and problems associated with environmental sensitivity are overcome.

SUMMARY OF THE INVENTION

In one aspect, this invention involves a polymeric dye comprising a polymeric entity having attached thereto a plurality of synthetic signal-generating groups. The polymeric dye is preferably an optimized highly-fluorescent polymer. The polymeric dye can be synthetically derived. It is preferred that the polymeric dye further contain hosting moieties either covalently bonded to the polymeric entity or in close proximity to the polymeric entity.

The signal-generating groups are derived from dyes having at least one anilino moiety coupled to a heterocyclic moiety containing at least one nitrogen atom in the heterocycle by means of an ethylenically unsaturated linking group. If the polymeric entity is nucleophilic, the signal-generating groups must be electrophilic. If the polymeric entity is electrophilic, the signal-generating groups must be nucleophilic. If the polymeric entity is nucleophilic, it can contain repeating units selected from the groups consisting of acrylamide hydrazido, hydrazide, and lysine. If the polymeric entity is electrophilic, it can contain repeating units selected from the group consisting of acrylic, glutamic, aspartic, and styrene sulfonic. If the signal-generating groups are electrophilic, they can contain carboxylic groups. If the signal-generating groups are nucleophilic, they can contain amine groups or hydrazide groups or both amine groups and hydrazide groups.

The hosting moiety can be covalently bound to the polymeric entity, but it need not be covalently bound to the polymeric entity. The hosting moiety can be attached to an entity other than the polymeric entity to which are attached the synthetic signal-generating groups. The hosting moiety is a hydrophobic and conformationally restricting moiety. The hosting moiety is preferably a cyclodextrin, more preferably a derivative of β-cyclodextrin aldehyde. The signal-generating groups are sensitive to proteins, nucleic acids, macromolecules, and lipids in a normal environment, but substantially insensitive to these materials in this hydrophobic and conformationally restricting microenvironment.

The signal-generating moiety of the polymeric dye is preferably a pyridinium anilino derivative. The pyridinium anilino derivative can comprise a pyridinium anilino derivative of the formula:

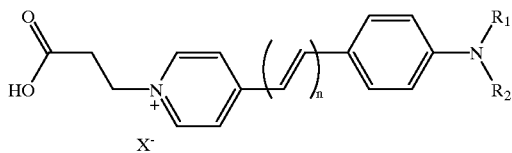

where $R_1$ represents an alkyl group and $R_2$ represents an alkyl group and n represents an integer from 1 to 3, inclusive, and $X^-$ represents a negatively charged counter ion In another embodiment, the signal-generating moiety of the polymeric dye is a benzothiazolium aniline derivative of the formula:

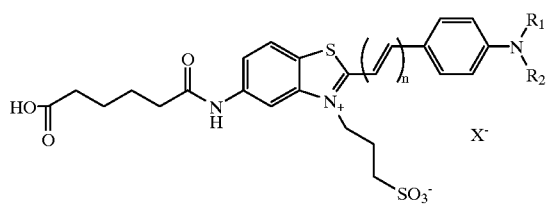

where $R_1$ represents an alkyl group and $R_2$ represents an alkyl group and n represents an integer from 1 to 3, inclusive, and $X^-$ represents a negatively charged counter ion In another aspect, the invention involves a conjugate comprising an antibody and at least one polymeric dye of this invention conjugated with the aforementioned antibody.

The invention may be employed in a number of applications, including, but not limited to, multiplexing assays, including multiplexing by multicolor fluorescence immunoassay, flow cytometry, immuno-phenotyping assays, imaging applications, immunological staining, fluorescence microscopy, immuno-chromatographic staining, fluorescence polarization immunoassay (FPIA), fluorescence in situ hybridization (FISH), fluorescence detection of analytes, and others. The invention is particularly effective for flow cytometry applications. However, it is not limited to those applications and, in fact, is suitable for many applications in which fluorescence testing or detection is involved and which are subject to problems like those previously discussed with respect to the prior art.

This invention reduces the problems typically encountered with phycobiliprotein instability and bio-conjugability along with the problems associated with using tandem systems in energy transfer processes. Additionally, many of the signal-generating groups suitable for use in this invention are synthetic. Synthetic signal-generating groups are typically more stable than naturally-occurring fluorophores.

The present invention decreases the environmental sensitivity of these and other dyes by providing these dyes with an appropriate and desired microenvironment. By so fixing the dyes in such a microenvironment, the effectiveness of the fluorescing properties of these dyes is not significantly affected by macro-environment, conjugation, or other factors.

BRIEF DESCRIPTION OF THE DRAWINGS

FIG. 3 also compares fluorescence of polymeric dye 11B with polymeric dye 11D at emission wavelength of 580 nm.

FIG. 6 also shows fluorescence response of polymeric dye 17B as a function of concentration of polymeric dye 17B and fluorescence response of polymeric dye 17B in a 0.25 mg/ml cyclodextrin stock diluent as a function of concentration of polymeric dye 17B.

DETAILED DESCRIPTION OF THE INVENTION

Figure 1:
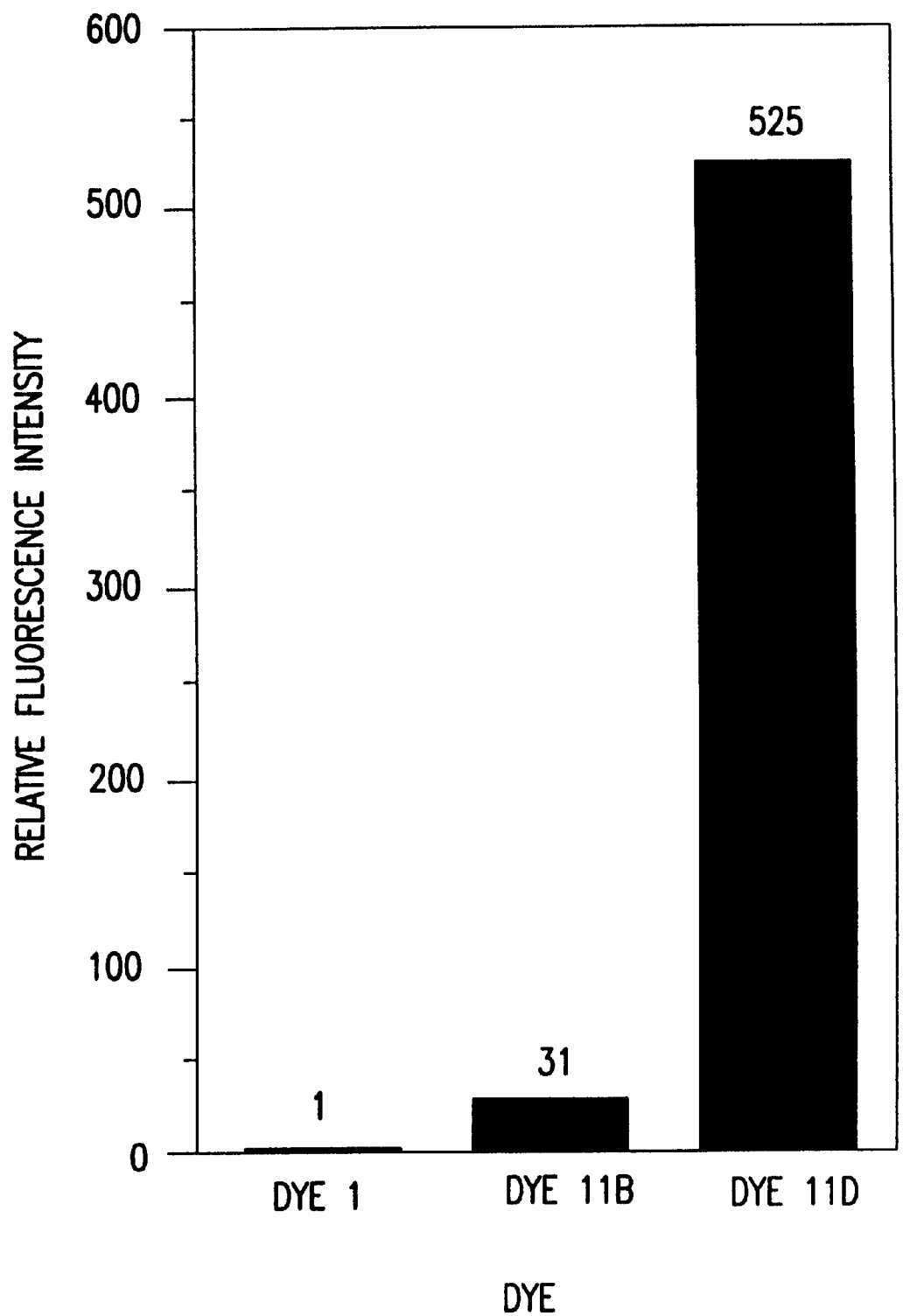
FIG. 1 compares fluorescence intensity of Dye 1, polymeric dye 11B, and polymeric dye 11D at excitation wavelength of 488 nm and emission wavelength of 614 nm.

The following definitions are applicable to this disclosure:

The term "analyte", as used herein, refers to a compound or composition to be detected. An analyte has at least one epitope or binding site. An analyte can be any substance for which there exists a naturally-occurring binding member or for which a binding member can be prepared. Analytes include, but are not limited to, toxins, organic compounds, proteins, peptides, microorganisms, cells contained in human or animal blood, cell surface antigens, nucleic acids, hormones, steroids, vitamins, drugs (including those administered for therapeutic purposes as well as those administered for illicit purposes), virus particles, and metabolites of or antibodies to any of the foregoing substances. Representative examples of analytes include ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); pestradiol, progesterone; IgE antibodies; vitamin B2 microglobulin; glycated hemoglobin (Gly. Hb); cortisol; digitoxin; N-acetylprocainamide (NAPA); procainamide; antibodies to rubella, such as rubella-lgG and rubella-lgM; antibodies to toxoplasmosis, such as toxoplasmosis IgG (Toxo-lgG) and toxoplasmosis IgM (Toxo-lgM); testosterone; salicylates; acetaminophen; hepatitis B virus surface antigen (HBsAg); antibodies to hepatitis B core antigen, such as anti hepatitis B core antigen IgG and IgM (Anti-HBc); human immune deficiency virus 1 (HIV) and 2 (HTLV); hepatitis B e antigen (HBeAg); antibodies to hepatitis B e antigen (Anti-HBe); thyroid stimulating hormone (TSH); thyroxine (T4); free triiodothyronine (Free T3); carcinoembroyoic antigen (CEA); and alpha fetal protein (AFP); and drugs of abuse and controlled substances, including but not limited to, amphetamine; methamphetamine; barbiturates, such as amobarbital, secobarbital, pentobarbital, phenobarbital, and barbital; benzodiazepines such as Librium and Valium; cannabinoids such as hashish and marijuana; cocaine; fentanyl; LSD; methapualone; opiates such as heroin, morphine, codeine, hydromorphone, hydrocodone, methadone, oxycodone, oxymorphone and opium; phencyclidine; and propoxyphene. The term "analyte" includes any antigenic substances haptens, antibodies, macromolecules, and combinations thereof.

The term "cyclodextrin", as used herein, refers collectively to $\alpha$, $\beta$, or $\gamma$ cyclodextrin, unless expressly stated otherwise to be a particular one of those.

The expression "optimized highly-fluorescent polymer", as used herein, refers to a polymeric entity that has a plurality of signal-generating groups immobilized thereon. The immobilized signal-generating groups are attached to the polymeric entity in such a manner as to maximize the signal generated from the signal-generating groups and to minimize the quenching effect associated with having a plurality of signal-generating groups spaced too close to each other.

The expression "primary reagent", as used herein, refers to a reagent that specifically binds an analyte. The primary reagent is used as a bridge between the analyte, to which it is bound, and a conjugate, which binds the primary reagent.

The expression "signal-generating group", as used herein, refers to a fluorescent moiety (sometimes referred to as a fluorophore) that is capable of absorbing energy and emitting light or fluorescing. Representative examples of parent dyes that provide signal-generating groups include aminostyryl pyridinium dyes, benzothiazole alanine diene, benzothiazole pyridinium triene, fluorescein, cascade blue, "TEXAS RED" (Sulforhodamine 101 acid chloride), p-phthallocyanines, cyanine dyes, thiazoles, dansyl, napthalene, p-toluidinyl napthalene sulfonic acid, coumarin, and phycoerythrin, allophycocyanine. Methods of deriving signal-generating groups from the parent dyes are well-known to those of ordinary skill in the art.

The expression "specific binding member", as used herein, means a member of a specific binding pair. A binding pair comprises two different and distinct molecules, wherein one of the molecules specifically binds to the other molecule by chemical or physical means. In addition to antigen and antibody specific binding pairs, other specific binding pairs include, but are not limited to, avidin and biotin, carbohydrates and lectins, complementary nucleotide sequences, complementary peptide sequences, effector and receptor molecules, an enzyme cofactor or substrate and an enzyme, an enzyme inhibitor and an enzyme, polymeric acids and bases, dyes and protein binders, peptides and specific protein binders (e.g., ribonuclease, S-peptide and ribonuclease S-protein), and the like. Furthermore, binding pairs can include members that are analogues of the original binding member, for example, an analyte-analogue or a binding member made by recombinant techniques or molecular engineering. If the binding member is an immuno-reactant, it can be, for example, a monoclonal or polygonal antibody, a recombinant protein or recombinant antibody, a chimeric antibody, or a mixture(s) or fragment(s) of the foregoing.

The expression "test sample", as used herein, refers to a material suspected of containing the analyte. The test sample can be used directly as obtained from the source or following a pre-treatment to modify the character of the sample. The test sample can be obtained from any biological source, such as a physiological fluid, including, but not limited to, blood, saliva, ocular lens fluid, cerebral spinal fluid, sweat, urine, milk, ascites fluid, mucous, synovial fluid, peritoneal fluid, amniotic fluid, and the like, and fermentation broths, cell cultures, and chemical reaction mixtures, and the like. The test sample can be pretreated prior to use, such as by preparing plasma from blood, diluting viscous fluids, and the like. Methods of treatment can involve filtration, distillation, concentration, inactivation of interfering components, and the addition of reagents. In addition to biological or physiological fluids, other types of liquid samples can be used. Representative examples of such liquid samples include water, food products, and the like, for the performance of environmental or food production assays. In addition, a solid material suspected of containing the analyte can be used as the test sample. In some instances, it may be beneficial to treat a solid test sample to form a liquid medium or extract the analyte.

In one aspect, the present invention provides a polymeric dye comprising:
(1) a polymeric entity;
(2) a plurality of signal-generating groups attached to said polymeric entity.

Preferably, the polymeric dye further comprises a plurality of hosting moieties for said signal-generating groups, said hosting moieties either covalently bonded to the polymeric entity or in close proximity to the polymeric entity. As used herein, "close proximity" typically means 100 Angstroms or less on average, preferably from 10 to 20 Angstroms on average.

Polymeric Entity

The signal-generating groups are attached to the polymeric entity. The polymeric entity facilitates bioconjugation and solubility of the polymeric dye. In addition, the polymeric entity allows for binding of a plurality of signal-generating groups to a single cell or molecule.

In the preferred embodiment of the present invention, the polymeric entity is a water-soluble polymer having functional groups that allow for attachment of signal-generating groups by covalent bonds. Preferably, the polymeric entity comprises amine functional groups, such as, for example: —C(O)—NH—NH$_2$, —NH$_2$, —NHR wherein R represents a member selected from the group consisting of alkyl group having 1 to 3 carbon atoms, inclusive, isopropyl, —(CH$_2$)$_2$CO$_2$—, —(CH$_2$)$_2$SO$_3$—, —(CH$_2$)$_2$NH$_3$$^+$, —(CH$_2$)$_2$NH$_2$$^+$(CH$_2$)$_2$SO$_3$—, —(CH$_2$)$_2$O(CH$_2$)$_2$O(CH$_2$)$_2$OH and —(CHOH)$_4$CH$_2$OH. The polymeric entity may also have combinations of the above-listed amine functional groups. The polymeric entity can comprise electrophilic functional groups, such as carboxyl groups, sulfonyl chloride groups, and activated ester groups. Preferably, the polymeric entity has a weight average molecular weight or number average molecular weight of from about 5,000 to about 500,000, more preferably from about 100,000 to about 250,000, and most preferably from about 150,000 to about 200,000.

When signal-generating groups are to be attached to the polymeric entity by covalent bonds, it is preferred to use as precursors for signal-generating groups parent dyes having a reactive group that is suitable for forming covalent bonds with the amine functional groups of the polymeric entity. Parent dyes that are capable of such a reaction include, but are not limited to, those having succinimidyl active ester groups, acid halide groups, sulfonyl halide groups, aldehyde groups, iodoacetyl groups, or maleimide groups. Examples of classes of parent dyes that may have the aforementioned functional groups include, but are not limited to, hemicyanine dyes, e.g., pyridinium aniline dyes, quinolinium aniline dyes, acridinium aniline dyes, benzothiazolium aniline dyes, benzoxazolium aniline dyes, benzimidizolium aniline dyes, naphthathiazolium aniline dyes, naphthindolium aniline dyes, naphthoxazolium aniline dyes, naphthimidizolium aniline dyes, and indolium aniline dyes.

As previously described, signal quenching is caused when a plurality of signal-generating groups are randomly covalently bonded to a single polymeric entity in close proximity to one another. Quenching can be substantially reduced by optimizing the number of signal-generating groups covalently bonded to the polymeric entity. Through optimization of the number of signal-generating groups covalently bonded to the polymeric entity, the conjugate of the present invention is able to emit a signal that can be better detected by a detection device, such as a flow cytometer.

Signal-Generating Group

The signal-generating group emits light having a sufficiently long wavelength relative to the wavelength of the excitation light, thereby dispensing with the requirement of an energy transfer mechanism and the problems related thereto. As used herein, "sufficiently long" typically means at least 50 nanometers, more preferably at least 100 nanometers, and most preferably at least 200 nanometers. A plurality of signal-generating groups can be attached to the polymeric entity. Even though the signal-generating group may itself be environmentally sensitive, and, consequently, unstable, and, for that reason, may have limited or problematic bioconjugability, enhancement by hosting moieties fixes the signal-generating group in a suitable microenvironment, thereby preserving the effectiveness of the signal-generating group.

A wide variety of signal-generating groups can be used for the invention. Signal-generating groups that exhibit high Stokes' shift are particularly useful. As used herein, high Stokes' shift ranges from about 50 to about 200 nanometers.

The signal-generating groups are derived from parent dyes having at least one anilino moiety coupled to a heterocyclic moiety containing at least one nitrogen atom in the heterocycle by means of an ethylenically unsaturated linking group. If the polymeric entity is nucleophilic, the signal-generating groups must electrophilic. If the polymeric entity is electrophilic, the signal-generating groups must be nucleophilic. If the polymeric entity is nucleophilic, it can, for example, contain repeating units selected from the groups consisting of acrylamide hydrazido, hydrazide, and lysine. If the polymeric entity is electrophilic, it can, for example, contain repeating units selected from the group consisting of acrylic, glutamic, aspartic, and styrene sulfonic. If the signal-generating groups are electrophilic, they can contain carboxylic groups. If the signal-generating groups are nucleophilic, they can contain amine groups or hydrazide groups or both amine groups and hydrazide groups. Representative classes of signal-generating groups suitable for this invention include hemicyanine dyes, e.g., pyridinium aniline dyes, quinolinium aniline dyes, acridinium aniline dyes, benzothiazolium aniline dyes, benzoxazolium aniline dyes, benzimidizolium aniline dyes, naphthathiazolium aniline dyes, naphthindolium aniline dyes, naphthoxazolium aniline dyes, naphthimidizolium aniline dyes, and indolium aniline dyes.

In general, parent dyes for signal-generating groups suitable for this invention can be represented by the formula:

A—L—B where A represents a heterocyclic group;
L represents a linking group; and
B represents an anilino group.

It is preferred that the group A contain from one to three rings. If more than one ring is included in the heterocyclic group, it is preferred that they be fused. Atoms that can be in the heterocyclic ring, other than the carbon atoms, are preferably nitrogen, oxygen, and sulfur atoms. The ring atoms can contain substituents other than hydrogen. However, these substituents must not adversely affect the interaction between the signal-generating groups and the hosting moiety. It is preferred that the group B have the formula:

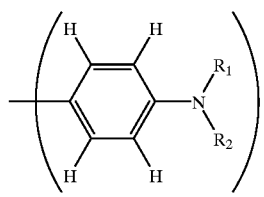

where $R^1$ represents an alkyl group having from 1 to 6 carbon atoms; and
$R^2$ represents an alkyl group having from 1 to 6 carbon atoms. The ring atoms of B can contain substituents other than hydrogen. However, these substituents must not adversely affect the interaction between the signal-generating groups and the hosting moiety. It is preferred that L have the formula:

where n represents 1, 2, or 3.

Though a number of signal-generating groups may be employed for the invention, a preferred signal-generating group includes synthetic aminostyryl pyridinium, aminostyryl benzothiazolium, quinolinium, and acridinium dyes. Those dyes and the synthesis thereof are known to those of ordinary skill in the art. See, for example, Anthony C. Stevens et al., "Synthesis of Protein-Reactive (Aminostyryl)pyridinium Dyes", *Bioconjugate Chem.*, 1993, 4, 19–24, incorporated herein by reference. The preferred pyridinium anilino dye is a monomeric aminostyryl fluorogen having the formula:

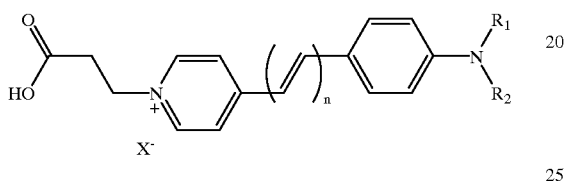

where $R_1$ represents an alkyl group and $R_2$ represents an alkyl group and n represents an integer from 1 to 3, inclusive, and $X^-$ represents a negatively charged counter ion The excitation wavelength of this dye is about 488 nm and the emission wavelength is about 580 nm when=1; the excitation wavelength of this dye is about 488 nm and the emission wavelength is about 680 nm when n=2; and the excitation wavelength of this dye is about 544 nm and the emission wavelength is about 790 nm when n=3. This particular dye, or an amine or carboxylic derivative thereof, can serve as the precursor of the signal-generating group of the polymeric dye of the invention. Exceptional fluorescence results can be obtained in flow cytometry applications the signal-generating group is derived from this dye.

As has previously been described, the aminostyryl pyridinium dyes had not been considered suitable for many of the fluorescence assays, such as flow cytometry, and other fluorescence processes, primarily because those dyes are environmentally sensitive and emission intensity is very weak in aqueous solutions.

Another dye that has been found to have exceptional fluorescing properties when serving as the signal-generating group is benzothiazolium anilino dye having the following structure:

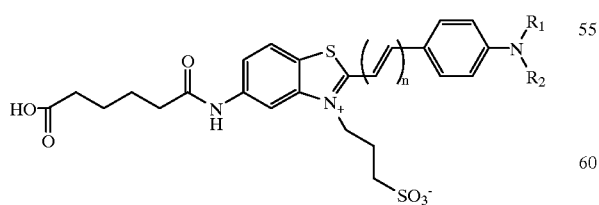

where $R_1$ represents an alkyl group and $R_2$ represents an alkyl group and n represents an integer from 1 to 3, inclusive The excitation wavelength of this dye is about 488 nm and the emission wavelength of this dye is about 580 nm when employed as a fluorophore in a polymer enhanced by covalent attachment of β-cyclodextrin aldehyde when n=1. The excitation wavelength of this dye is about 488 nm and the emission wavelength of this dye is about 680 nm when employed as a fluorophore in a polymer enhanced by covalent attachment of β-cyclodextrin aldehyde when n=2. The excitation wavelength of this dye is about 488 nm and the emission wavelength of this dye is about 750 nm when employed as a fluorophore in a polymer enhanced by covalent attachment of β-cyclodextrin aldehyde when n=3. Certain analogues of these anilino dyes will also yield exceptional fluorescence results. These analogues include, but are not limited to, the following dyes, where n represents an integer from 1 to 3, inclusive, and $X^-$ represents a negatively charged counter ion. amino pyridinium anilino

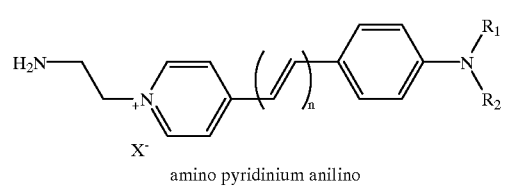
amino pyridinium anilino

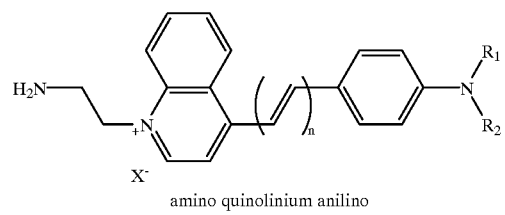
amino quinolinium anilino

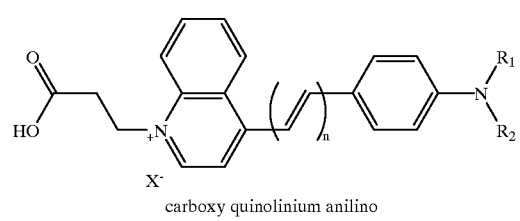
carboxy quinolinium anilino

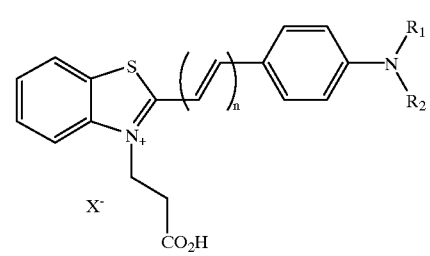
carboxy benzothiazolium anilino

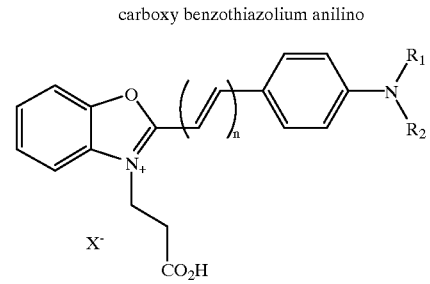
carboxy benzoxazolium anilino

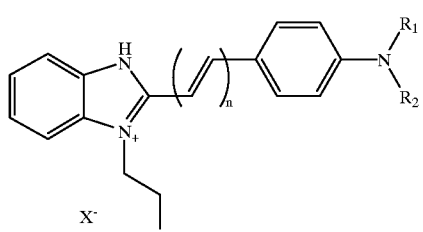
carboxy benzimidazolium anilino
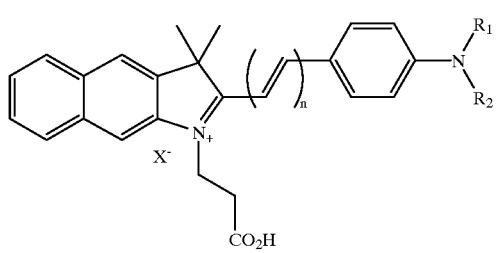
carboxy naphthindolium anilino
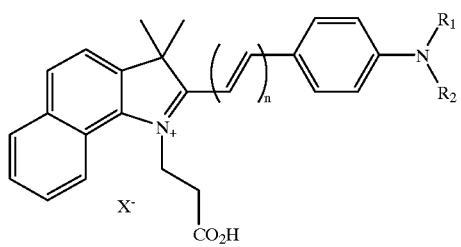
carboxy naphthindolium anilino
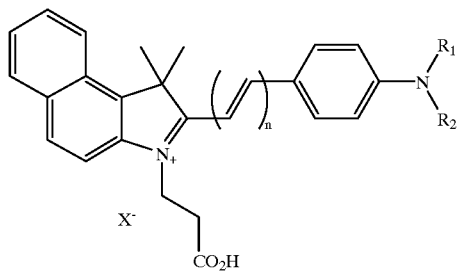
carboxy naphthindolium anilino
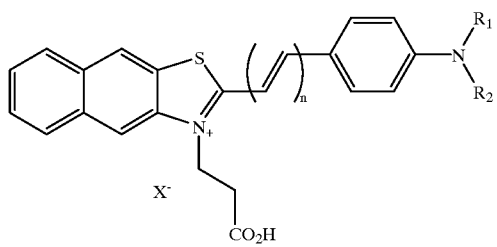
carboxy naphthothiazolium anilino
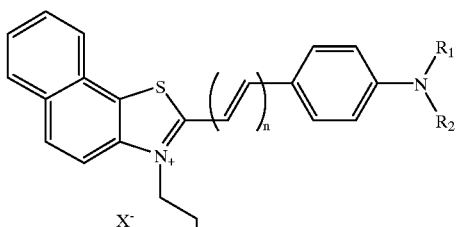
carboxy naphthothiazolium anilino
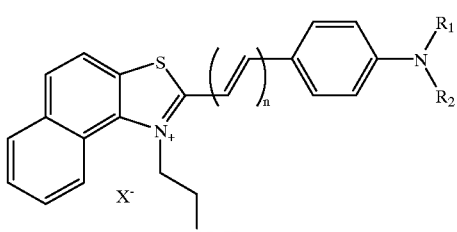
carboxy naphthothiazolium anilino
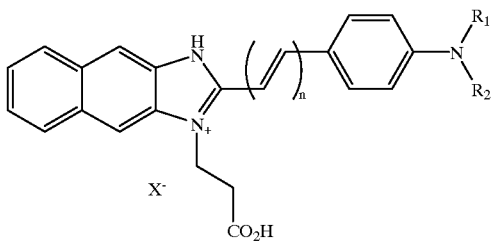
carboxy naphthimidizolium anilino
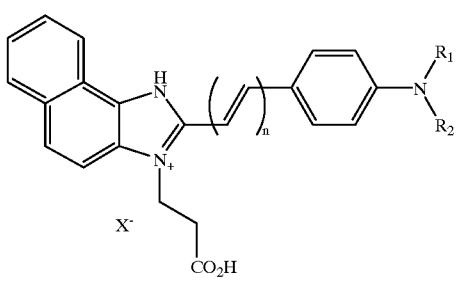
carboxy naphthimidizolium anilino
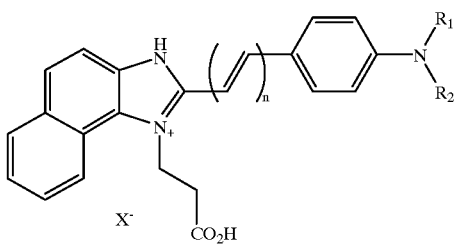
carboxy naphthimidizolium anilino -continued

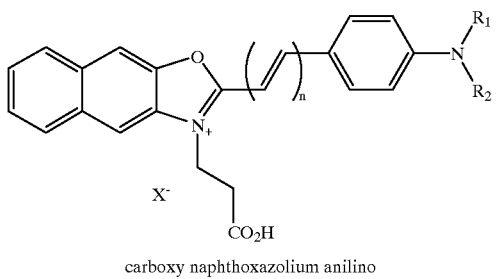

carboxy naphthoxazolium anilino

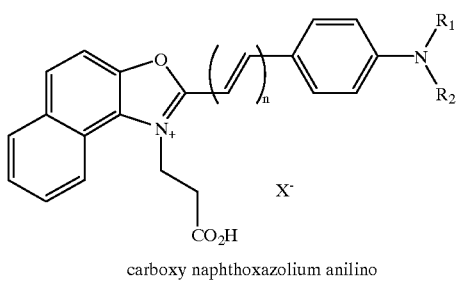

carboxy naphthoxazolium anilino

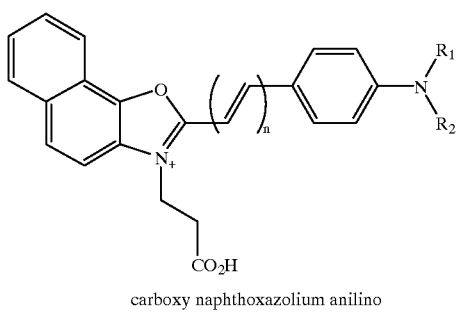

carboxy naphthoxazolium anilino

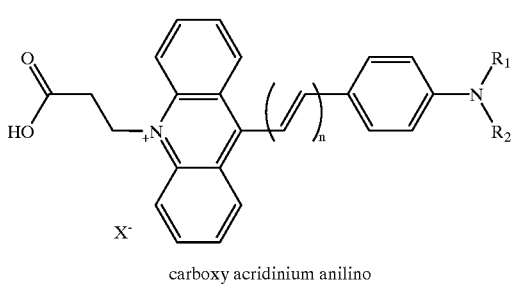

carboxy acridinium anilino

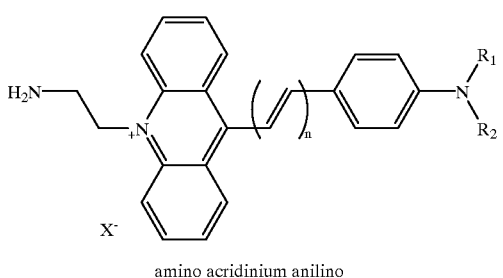

amino acridinium anilino

The parent dyes may be substituted or unsubstituted, i.e., the heterocyclic portion of the parent dye can contain substituents other than hydrogen. Furthermore, the anilino portion of the dye can contain substituents other than hydrogen. The particular nature of these optional substituents is not critical. However, these substituents must not adversely affect the interaction of the signal-generating groups with the hosting moiety. Substituents that are suitable for either the heterocyclic portion of the dye or the anilino portion of the dye include, but are not limited to, alkyl, alkenyl, amino, methoxy, chloro, fluoro, bromo, hydroxy, and nitro.

The process of binding the signal-generating groups to the polymeric entity is referred to as loading the polymer. However, merely loading the polymeric entity with signal-generating groups may not result in a polymeric dye that emits the maximum amount of fluorescence achievable. If the polymeric entity is overloaded, quenching may result; if the polymeric entity is underloaded, signal-generating groups that could have been added without experiencing quenching will be left out, thereby resulting in a lower than maximum level of fluorescence. Thus, it is preferred that the number of signal-generating groups attached to a polymeric entity be optimized in order to generate a polymer capable of emitting the greatest level of fluorescence.

Optimizing the number of signal-generating groups on a polymeric entity can be accomplished by executing a series of loadings and then determining which level of loading yields the polymeric dye that emits the greatest level of signal. Generally, this procedure can be carried out by creating a panel of trial loadings that combine varying concentrations of signal-generating groups with a constant amount of polymeric entity. The loaded polymeric entities can then be separated from any unreacted materials by a variety of methods known to those of ordinary skill in the art, such as precipitation, isoelectric focusing, or, preferably, size exclusion chromatography. The separated polymers can then be tested for their ability to emit a signal to determine which loading concentration yields the polymeric dye that emits the greatest level of signal. Typically, the polymeric dye displaying the greatest level of signal has been optimally loaded, and the concentration at which it was loaded can be used to optimally load amounts of the polymeric entity for scale-up purposes. As used herein, "optimal loading" means attaching the maximum number of signal-generating groups to the polymeric entity without bringing about quenching or adversely affecting bioconjugability.

The preferred method for determining the optimum number of signal-generating groups for attachment to a particular polymeric entity involves the steps of:

(1) calculating the molecular weight of the selected polymeric entity;

(2) determining the total molar quantity of reactive groups, e.g., amine functional groups, present on the polymeric entity;

(3) creating a panel consisting of a series of stock solutions, each of which contains a different concentration of signal-generating groups;

(4) loading signal-generating groups onto the polymeric entities via reaction with reactive groups, e.g., amine-functional groups;

(5) purifying (separating) loaded polymer from unreacted materials;

(6) analyzing polymeric dyes for their ability to emit signals; and (7) scaling-up.

The stock solutions comprise varying concentrations of the dyes having signal-generating groups dissolved in a suitable solvent, such as, for example, dimethylformamide (DMF) or dimethylsulfoxide (DMSO). The molar loading ratio of signal-generating groups to reactive groups of the polymeric entity, typically amine-functional groups, in the panel can be varied as follows: 5%, 10%, 15%, 20%, 40%, 75%, 100%, 140%, and 200%. The panel concentrations are preferably chosen to include sufficiently large molar loading ratios so that quenching will occur, or dye is maximally loaded, thereby clearly delineating the point at which the polymeric entity is optimally loaded. After the panel has been set up, each panel member is added to individual and equimolar solutions of the polymeric entity.

Each solution of loaded polymer can then be separated from unreacted polymeric entity and/or dyes having signal-generating groups by techniques known to one of ordinary skill in the art. As previously mentioned, after the polymers are separated, they can be analyzed for their ability to emit signal and a scaled-up amount of polymer can then be produced using the data so obtained.

Additional optimization panels can be executed to more accurately determine the optimal loading concentration. It is to be understood, of course, that the manner by which a polymer is optimized is not intended to be limited to the methods described herein, and that other methods can be employed as well.

The polymeric dye can be attached to a specific binding member by means of a variety of techniques known to one of ordinary skill in the art. It is preferred to attach the polymeric dye at or near the Fc portion of an antibody by a covalent bond, thereby forming a conjugate. While not wishing to be bound by any theory, it is speculated that attaching the polymer to an antibody in this manner sterically hinders the Fc portion of the antibody, thereby preventing it from binding, for example, Fc receptors present on the surface of certain cell populations. Additionally, the site specific attachment leaves the bindable regions of the antibodies unhindered and capable of binding their intended target. It is to be understood, of course, that the manner by which a specific binding member is attached to a polymeric dye is not intended to be limited to the methods described herein, and that other methods known to one of ordinary skill in the art can be employed as well.

A polymeric dye can be attached to an antibody to form a conjugate by oxidizing the Fc region of the antibody and then reacting the oxidized antibody with a polymeric dye of the type described herein. The antibody is preferably oxidized at a concentration of from about 1.0 mg/mL to about 20.0 mg/mL, more preferably from about 1.0 mg/mL to about 10.0 mg/mL, and most preferably from about 2.0 mg/mL to about 5.0 mg/mL. If the antibody is obtained in concentrations outside of these ranges, it can be concentrated by methods known to those of ordinary skill in the art or diluted with an appropriate buffer. The antibody is preferably oxidized in a buffer having a pH of from about 6.5 to about 8.0, more preferably from about 7.0 to about 8.0, and most preferably from about 7.5 to about 8.0. The oxidation of the Fc region of the antibody can be carried out with an oxidizing agent known to those of ordinary skill in the art. Such oxidizing agents include, but are not limited to, sodium periodate, bromine, and the like. Solutions containing the oxidizing agents typically have a concentration of oxidizing agent of from about 100 mM to about 250 mM, preferably from about 175 mM to about 200 mM. The oxidation of the antibody can take place at a temperature of from about 2° C. to about 30° C. Preferably, oxidation takes place at a temperature of from about 2° C. to about 8° C. for from about 15 minutes to about 5 hours, preferably from about 1 hour to about 2 hours. After the antibody has been oxidized, it can be purified, by methods known in the art, and placed in an appropriate buffer, which preferably has a pH ranging from about 3 to about 6, more preferably ranging from about 4 to about 5. The oxidized antibody can then be coupled to the polymeric dye. It is to be understood, of course, that the manner by which an antibody is oxidized is not intended to be limited to the methods described herein, and that other methods known in the art can be employed as well.

When reacting an oxidized antibody with a polymeric dye, the concentration of the polymeric dye can range from about 1.0 mg/mL to about 20.0 mg/mL, preferably from about 2.0 mglmL to about 5.0 mg/mL, in an appropriate buffer. Buffers suitable for this reaction preferably have a pH ranging from about 4.0 to about 7.0, more preferably ranging from about 4.0 to about 5.0. Suitable buffers for the reaction include, but are not limited to, triethanolamine, phosphate. The amount of polymeric dye added to the oxidized antibody can range from about 1.0 to about 20 equivalents of polymeric dye to one equivalent of antibody, based on the molecular weight of the antibody and the estimated molecular weight of the polymeric dye. The reaction between the oxidized antibody and the polymeric dye can take place at a temperature of from about 2° C. to about 30° C., preferably from about 2° C. to about 8° C. in a light tight container. The reaction can be allowed to run for from about 2 to about 48 hours, preferably from about 12 to about 15 hours. Upon completion of the reaction, the conjugate can be separated from the unreacted components of the reaction mixture by means of separation methods known to those of ordinary skill in the art.

In cases where polymeric dyes having primary or secondary amine functional groups are attached to a specific binding member by a covalent bond, an additional step is preferred. As a result of the initial reaction between the antibody and polymeric dye, a Schiff base is formed, and reduction of the Schiff base can be accomplished by methods known ito one of ordinary skill in the art, such as the use of a suitable reducing agent, such as $NaCNBH_3$, at a concentration ranging from about 0.25 mg/mL to about 2.0 mg/mL. The reduced conjugate can then be separated from excess reactants by separation techniques known to one of ordinary skill in the art. It is to be understood, of course, that the manner by which a Schiff Base is reduced is not intended to be limited to the methods described herein, and that other methods can be employed as well.

It is preferred that the signal-generating groups covalently bonded to the polymeric entity be hosted within a hydrophobic cavity of a molecule that is covalently bound to the polymeric entity. In this preferred embodiment, the signal-generating groups do not need to have any reactive group. However, as will be understood by those of ordinary skill in the art, the signal-generating group will be one that is capable of being hosted by the particular hosting moiety being used.

Hosting Moiety

The hosting moiety must provide a hydrophobic and conformationally restrictive microenvironment. The hydrophobicity allows the hosting moiety to be compatible with the signal-generating groups. The conformational restrictivity is believed to improve fluorescence of the signal-generating groups. Representative example of host moieties characterized by small molecules include cyclodextrins, e.g., α-cyclodextrins, β-cyclodextrins, γ-cyclodextrins; carcerands; calixiranes; molecular clefts; cucurbiterils; and cyclophanes. Carcerands are described in J.-M. Lehn, *Struct. Bonding (Berlin)* 16 (1973) 1; J.-M. Lehn, *Acc. Chem. Res.* 11(1948) 49; P. G. Potvin, J.-M. Lehn in R. M. lzatt, J. J. Christensen (Eds.): *Synthesis of Macrocycles: The Design of Selective Complexing Agents (Progress in Macrocycle Chemistry,* Vol. 3), Wiley, New York 1987, p. 167; D. J. Cram,*Angew. Chem.* 98 (1986) 1041;*Angew. Chem. Int. Ed. Engl.* 25 (1986) 1039; B. Dietrich, *J. Chem. Ed.* 62 (1985) 954; and D. J. Cram, K. N. Trueblood, *Top. Curr. Chem.* 98

(1981) 43. Calixiranes are described in B. Xu and T. Swager, "Host-Guest Mesomorphism: Cooperative Stabilization of a Bowlic Columnar Phase", *J. Am. Chem. Soc.* 1995, 117, 5011–5012. Molecular clefts are described in J. Rebek, Jr., *Acc. Chem Res.* 17 (1984) 258 and *Science* 235 (1987) 1478. Cucurbiturils are described in Mock, W. L., Shih, N. Y., *J. Org. Chem.,* 1983, 48 (20), 3618–3619. Cyclophanes are described in F. Diederich, M. R. Heester, M. A. Uyeki, *Angew. Chem.* 1988, 100, 1775; *Angew Chem. Int. Ed. Engl,* 1988, 27, 1705.

Enhancement of the signal generated by the signal-generating groups of the polymeric dyes described herein is preferably achieved by attaching cyclodextrin, preferably β-cyclodextrin aldehyde, via covalent bond to the polymeric entity, preferably to the backbone of an optimized highly-fluorescent polymer. Alternatively, the cyclodextrin need not be covalently bonded to the polymeric entity, but need only be in close proximity to the polymeric entity.

The enhancement of an optimized highly-fluorescent polymer with β-cyclodextrin aldehyde via covalent bonding will be described below. The enhancement of an optimized highly-fluorescent polymer with one of the alternative hosting moieties is substantially similar to that enhancement achievable with a cyclodextrin. Attachment of cyclodextrin aldehyde to the polymeric entity of the polymeric dye by covalent bonding is preferred, because it has been found to provide the greatest enhancement of fluorescence. The cyclodextrin molecule can be attached to the polymeric entity by the primary rim of the cyclodextrin molecule by selectively incorporating a single reactive group on the primary rim of the cyclodextrin molecule. Thus, the secondary rim will be unhindered and the hydrophobic cavity will be accessible to guest molecules. Attaching the primary rim of a cyclodextrin molecule to a polymeric entity having amine functional groups can be accomplished by converting a single aldehyde group on the primary rim of the cyclodextrin molecule and then reacting that group with an amine group present on the polymeric entity, whereby the cyclodextrin molecule is attached to the polymeric entity via a single covalent bond. As previously mentioned, the generation of a single aldehyde group at the primary rim of a cyclodextrin molecule can be accomplished by methods known in to one of ordinary skill in the art. For example, an aldehyde can be generated at the primary rim of cyclodextrin by using the Dess-Martin periodonane reagent. D. B. Dess et al., *J. Org. Chem.,* 48, 4155–4156 (1983). This reaction can be carried out in a heterogeneous system containing stoichiometric amounts of Dess-Martin reagent and cyclodextrin dissolved in tetrahydrofuran (THF). Although 6-cyclodextrin monoaldehyde is produced, Dess-Martin reagent is potentially explosive and is no longer readily available from commercial sources. Other routes to the monoaldehyde involve three to four steps that produce toxic and potentially explosive azide intermediates.

Alternatively, a method of producing 6-cyclodextrin monoaldehydes that does not involve the production of dangerous intermediates has been discovered. The method can be carried out with materials that are readily available commercially. Generally, the method involves two steps and can be carried out as shown below in Scheme 1.

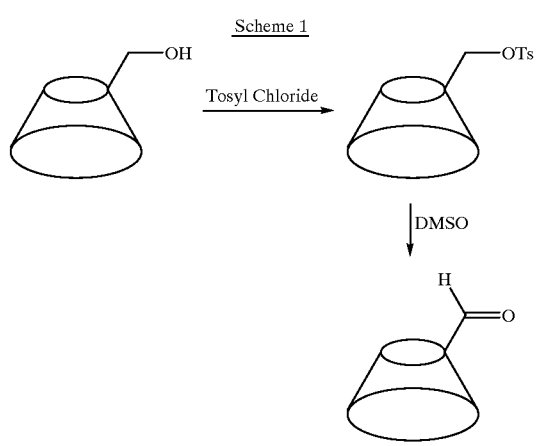

Scheme 1

The first step of the method involves converting a cyclodextrin to its monotosylate derivative. The tosylate derivative is then oxidized to yield the cyclodextrin monoaldehyde.

There are several methods for converting the cyclodextrin to its monotosylate derivative. See L. D. Melton et al., *Carbohydrate Research,* 18, 1971, 29–37 or R. C. Petter et al., *J Am. Chem. Soc.* 1990, 112, 3360–3368, incorporated herein by reference. After the monotosylate has been formed, it can be separated from the reaction mixture by methods known to those of ordinary skill in the art, preferably, High Performance Liquid Chromotography (HPLC). The solid monotosylate can then be recovered by removing the solvent from the solution containing dissolved cyclodextrin monotosylate by methods known to those of ordinary skill in the art. The solid cyclodextrin monoaldehyde can then be used in the second step of the process.

The oxidation step of the method can be carried out by a variety of methods. Typically, the oxidation step involves a dimethylsulfoxide (DMSO)-mediated reaction that can be catalyzed through the addition of a base. It was found that heating the monotosylate derivative to a temperature of from about 75° C. to about 85° C. in DMSO resulted in the slow conversion (about 1–3 days) of the tosylate derivative to the monoaldehyde.

The addition of base to the DMSO-mediated reaction can be used to increase the rate of conversion from the monotosylate to the monoaldehyde. For example, a trace amount of sodium hydroxide (NaOH) can be used to accelerate the reaction. Preferred bases for use in this step of the process include hindered amine bases, such as diisopropyl amine, N-methyl morpholine, triethyl amine, trimethyl amine, and the like. Diisopropylethyl amine (also known as Hunig's Base) is a particularly preferred hindered amine base. The conversion of the monotosylate to the monoaldehyde is preferably accomplished when the monotosylate is present in solution at a concentration of from about 0.5% to about 20% by weight, more preferably from about 1% to about 15% by weight, and most preferably from about 2% to about 10% by weight. The amount of hindered amine base suitable for the conversion can range from about 0.1 to about 1.0 molar equivalents of the monotosylate in solution, preferably from about 0.3 to about 0.7 molar equivalents of the monotosylate in solution. The cyclodextrin monoaldehyde thus formed can be separated from any unreacted material by methods known to one of ordinary skill in the art and reacted with an amine-functional polymer. Alternatively, the final reaction mixture can be directly reacted with an amine-functional polymer.

The cyclodextrin monoaldehyde provided herein can easily be attached to compounds that have amine or hydrazide functional groups by means of standard covalent chemistry methods known to those of ordinary skill in the art. Examples of such amine functional groups include, but are not limited to: $-C(O)-NH-NH_2$, $-NH_2$, $-NHR$ wherein R represents a member selected from the group consisting of alkyl having 1 to 3 carbon atoms, inclusive, isopropyl, $-(CH_2)_2CO_2-$, $-(CH_2)_2SO_3-$, $-(CH_2)_2NH_3^+$, $-(CH_2)_2NH_2^+$, $(CH_2)_2SO_3-$, $-(CH_2)_2O(CH_2)_2O(CH_2)_2OH$ and $-(CHOH)_4CH_2OH$. Examples of compounds that have these amine functional groups include, but are not limited to, amine functional polymers such as polyacrylamide hydrazide and amine functional solid phases, such as aminated microparticles.

In cases where primary or secondary amine functional compounds are reacted with cyclodextrin monoaldehyde to form covalent bonds, an additional step is preferred. After the initial reaction between the compound and the monoaldehyde takes place, a Schiff base is formed and the reduction of the Schiff base can be accomplished in the manner previously described.

The cyclodextrin monoaldehyde can be attached to amine functional polymeric entities that do not contain signal-generating groups or to amine functional polymeric dyes, which contain signal-generating groups. If the cyclodextrin monoaldehyde is added to an amine functional polymeric entity that does not contain signal-generating groups, the polymeric entity can subsequently be rendered fluorescent by addition of signal-generating fluorophores to the polymeric entity. One way in which the polymeric entity can be rendered fluorescent is through the attachment of the signal-generating groups to the amine functional polymeric entity by covalent bonds.

The fluorescence of conjugates containing the polymeric dyes of this invention can be enhanced by adding cyclodextrin to the conjugate by means of a non-covalent bond. When cyclodextrin is used in this manner, no modification need be made to the cyclodextrin molecule or to the conjugate. While not wishing to be bound by any theory, it is believed that the cyclodextrin associates with the signal-generating groups present on the polymeric dye by hosting the covalently bonded signal-generating groups within the hydrophobic center of the cyclodextrin molecule. When cyclodextrin is used to enhance the fluorescence of a polymeric dye, it is preferably used in concentrations ranging from about 5 mM to about 200 mM, preferably from about 10 mM to about 20 mM.

As previously mentioned the conjugate of this invention has a variety of uses. The preferred method of using the conjugate of this invention is in a flow cytometry application that employs a fluorescent conjugate or multiple fluorescent conjugates to detect cells contained in a test sample. An example of a flow cytometer is the Fluorescence Activated Cell Sorter (FACS II) manufactured by Becton, Dickinson & Co, Franklin Lakes, N. J. In general, an imaging system contains an excitation source and a detection device. The excitation source excites the signal generating group associated with the conjugate and the detection device detects the signal emitted from the excited signal generating group.

In a typical imaging system analysis, a test sample is incubated with a fluorescent conjugate, which specifically binds certain cells that may be present in the test sample. The incubation takes place for a time and at a temperature conducive for the binding of the conjugate to specific cell populations contained in the sample. The cells bound with the conjugate are commonly referred to as being stained and the staining procedure can be executed multiple times, sequentially or at the same time, with multiple conjugates, which emit signals of varying wavelengths. After the staining procedure is complete, the sample can be analyzed using a flow cytometer.

In an alternative preferred embodiment of flow cytometry with the polymeric dye of the present invention, a test sample is incubated with a solution of primary reagent, which specifically binds certain cells that may be present in the test sample to form primary complexes. The unbound reagent, if any, can be washed from the sample, and a fluorescent conjugate specific for the bound primary reagent is then incubated with the primary complexes. The unbound conjugate, if any, can then be removed from the primary complexes and the fluorescence associated with the cells can then be determined as above. It will be understood that the staining procedure can be repeated multiple times with primary reagents specific for different cell markers and conjugates which fluoresce at the same or at different wavelengths. It will also be understood, of course, that the staining procedure can be accomplished in a sequential manner or in a batch type manner, wherein all of the components necessary for cell staining are added to the sample before the fluorescence associated with the cells is determined.

In an alternative embodiment, the conjugate and method of the present invention can be adapted for use in conventional solid phase immunoassays such as, for example, a sandwich type immunoassay. A sandwich type immunoassay typically involves contacting a test sample suspected of containing an analyte with a substantially solid inert plastic, latex or glass bead or microparticle, or other support material which has been coated with a specific binding member that forms a binding pair with the analyte. The binding member-coated support material is commonly referred to as a "capture reagent". After the analyte is bound to the support material, the remaining test sample is removed from the support material. The support material, to which the analyte is bound, is treated with a conjugate, which generally comprises a second binding member labeled with a signal-generating group. The conjugate becomes bound to the analyte, which is bound to the support material. The combination of support material having the first binding member, the analyte, and the conjugate bound thereon is separated from any unbound conjugate, typically with one or more wash steps. The signal generated by the signal generating group, through appropriate excitation, can then be observed visually, or more preferably by an instrument, to indicate the presence or amount of an analyte in a test sample. It will be understood, of course, that the order and number of the steps employed to perform such assays are not intended to limit the invention described herein.

As previously mentioned, the analyte detected by such an immunoassay can be the product or products of an amplification reaction. Accordingly, the analytes can comprise nucleic acid sequences or are otherwise the products of a hybridization reaction such as LCR, which is described in European Patent Applications EP-A-320-308 and EP-A-439-182, and PCR, which is described in U.S. Pat. Nos. 4,683,202 and 4,683,195, all of which are incorporated herein by reference. In cases where the analytes comprise, for example, LCR or PCR reaction products or sequences, the sequences can comprise or be modified to comprise a binding member that forms a binding pair with an indicator reagent and a binding member that forms a binding pair with a capture reagent.

Automated systems suitable for performing sandwich type immunoassays such as, for example, a Microparticle Enzyme Immunoassays (MEIAs) are well known in the art. A particularly preferred and commercially available automated instrument which can be employed to perform MEIAs is the IMx® system, which is available from Abbott Laboratories, Abbott Park, Ill. Protocols for MEIAs such as those performed by the Abbott IMx® instrument are well known in the art and have been described in Fiore, M. et al., Clin. Chem., 34/9: 1726–1732 (1988), incorporated herein by reference.

The hosting group-enhanced polymeric dyes of this invention provide exceptional results in flow cytometry, far exceeding those obtained with the heretofore known fluorescent dyes, polymers, and conjugates. These polymeric dyes can be used in place of the heretofore known fluorescent dyes, polymers, and conjugates, such as phycobiliprotein-Cy5 tandems and the like.

Conventional signal-generating groups (i.e., fluorophores) with high Stokes' shifts are too dim to detect with reasonable sensitivity for multiplexing applications. The invention overcomes that problem and may be employed in a number of applications, including, but not limited to, multiplexing assays, including multiplexing by multicolor fluorescence immunoassay, flow cytometry, immuno-phenotyping assays, imaging applications, immunological staining, fluorescence microscopy, immunochromatographic staining, fluorescence polarization immunoassay (FPIA), fluorescence in situ hybridization (FISH), fluorescence detection of analytes, and others. The invention is particularly effective for flow cytometry applications. However, it is not limited to those applications and, in fact, is suitable for many applications in which fluorescence testing or detection is involved and which are subject to problems like those previously discussed with respect to the prior art.

Additionally, many of the signal-generating groups suitable for use in this invention are synthetic. Synthetic signal-generating groups are typically more stable than naturally-occurring fluorophores.

The present invention decreases the environmental sensitivity of these and other dyes by providing these dyes with an appropriate and desired microenvironment. By so fixing the dyes in such a microenvironment, the effectiveness of the fluorescing properties of these dyes is not significantly affected by macroenvironment, conjugation, or other factors.

The invention will be more specifically illustrated by the following non-limiting examples. In these examples, the following buffers were employed:

Phosphate buffer that contained 100 mM phosphate and 100 mM NaCl, pH 5.5 (hereinafter "Buffer No. 1")

Phosphate buffer that contained 100 mM phosphate and 100 mM NaCl, pH 7.0 (hereinafter "Buffer No. 2")

Triethanolamine buffer that contained 50 mM triethanolamine, 160 mM NaCl, pH 8.0 (hereinafter "Buffer No. 3")

Acetate buffer, pH 4.5 (0.1 N acetate, 0.1 N NaCl) (hereinafter "Buffer No. 4")

Acetate buffer, pH 5.5 (0.1 N acetate, 0.1 N NaCl) (hereinafter "Buffer No. 5")

Phosphate buffer that contained 50 mM triethanolamine, 160 mM NaCl, pH 7.0 with 0.1 mM ZnCl$_2$ and 1 mM MgCl$_2$. (hereinafter "Buffer No. 6")

HEPES buffer, pH 6.8 (0.1 N HEPES)(hereinafter "Buffer No. 7")

Phosphate buffer that contained 100 mM phosphate and 100 mM NaCl, pH 7.5 (hereinafter "Buffer No. 8")

20 mM phosphate buffer, pH 7.0 (0.02 N phosphate, 0.02 N sodium chloride) (hereinafter ""Buffer No. 9") In these examples, the following trademarks were employed:

"SEPHACRYL S-300", Pharmacia LKB Biotechnology AB

"CENTRICON-30", W.R. Grace & Co.

"PARR", Parr Instrument Co.

"CELITE", Celite Corporation

"SEPHADEX G-25", Pharmacia LKB Biotechnology AB

"CENTRIPREP-30", W.R. Grace & Co.

"BIO-GEL TSK-50XL", Toso-Haas Corporation

"BIO-SIL SEC-300", BioRa1d Corporation

EXAMPLE I

Preparation Of Cyclodextrin Derivative Of Acrylamide Hydrazide Pyridinium Aniline Monoene Polymer Dye 1 was prepared by reacting 4-(diethylamino) benzaldehyde with Synthetic Intermediate I in the presence of base. Synthetic Intermediate I was prepared by reacting 4-methyl pyridine with 3-iodo propionic acid. Acrylamide hydrazide pyridinium aniline monoene polymer 11B was prepared by reacting Dye 1 at the carboxyl substituent with a hydrazine moiety of acrylamide hydrazide polymer 11A using 1-ethyl-3-(3-dimethylaminopropyl) carbodiimide (hereinafter "EDAC") as a dehydrating agent. The resultant polymeric dye 11B was further reacted with cyclodextrin aldehyde 6 to produce a cyclodextrin derivative of acrylamide hydrazide pyridinium aniline monoene polymer 11D.

Preparation of Dye 1

A reaction mixture was prepared by combining 4-(diethylamino)benzaldehyde (0.5 g, 2.8 mmoles, Aldrich Chemical Co., Milwaukee, Wis.), an intermediate (Synthetic Intermediate I, 0.462 g), and piperidine (1 mL) in anhydrous ethanol (5 mL).

The reaction mixture was heated to a temperature of 100° C. and maintained at that temperature for four hours, then was cooled to room temperature (25° C.). The ethanol solvent was removed in vacuo, and the product subsequently was purified by preparative HPLC on a C-8 reverse phase column eluted with 2:1 methanol/water liquid phase. The yield of Dye 1 was 29%. The preparation is illustrated in Scheme 2A.

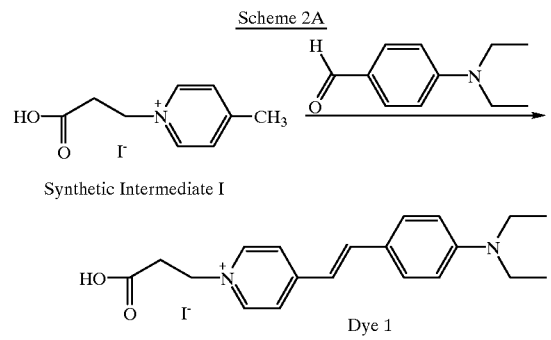

Synthetic intermediate I was prepared by refluxing a solution that consisted of 4-methyl pyridine (1 g, Aldrich Chemical Co., Milwaukee, Wis.) and 3-iodopropionic acid (10.7 g, Aldrich Chemical Co., Milwaukee, Wis.) in ethanol. The preparation is illustrated in Scheme 2B.

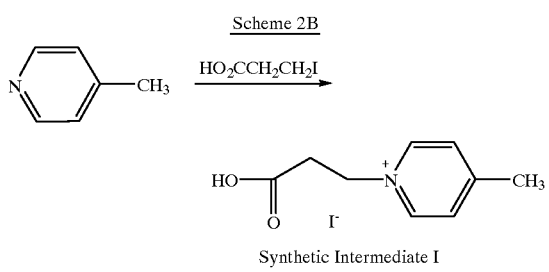

Synthetic Intermediate I

Synthetic Intermediate I was purified by silica gel chromatography using a gradient of 5 to 20% $CH_3OH$ in $CH_2Cl_2$ mobile phase.

Alternatively, Dye 1 can be synthesized using a modified synthetic route as described by Stevens, A. C. et al., *Bioconjugate Chemistry*, 1993, 4, 19–24, incorporated herein by reference.

Preparation Of Polymeric Dye 11B

Polymeric dye 11B was prepared by attachment of Dye 1 to polymeric entity 11A using EDAC as a dehydrating agent. Polymeric entity 11A (5 mg, Sigma Chemical Co., catalog #P-9505, MW 180,000) was dissolved in 1.0 ml phosphate buffer that contained 100 mM phosphate and 100 mM NaCl, pH 5.5 (hereinafter "Buffer No. 1"). Approximately 150 molar equivalents of Dye 1 (1.4 mg, $4.2 \times 10^{-6}$ mole) was added to this solution. Several 10 mg aliquots of solid EDAC were added at approximately ½ hour intervals while the reaction mixture was being stirred over the course of several hours. Purification was accomplished by size exclusion chromatography ("SEPHADEX G-25") using Buffer No. 1 as the mobile phase. The void volume fractions were then pooled.

Preparation Of Polymeric Dye 11D

After the chromatography step was carried out as described above, the concentration of the stock solution of resultant polymeric dye 11B in Buffer No. 1 was 0.5 mg/mL. An aliquot (3.0 mL) of the stock solution of polymeric dye 11B in Buffer No. 1 (1.5 mg of polymeric dye 11B) was taken and cyclodextrin aldehyde 6 (9.0 mg, prepared as described in Huff, J. B., Bieniarz, C., *J. Org. Chem.* 1994, 59, 7511–7516, incorporated herein by reference) was added to the aliquot. The resulting solution was allowed to incubate at room temperature (25° C.) for at least 24 hours. The resultant polymeric dye 11D was purified on a medium pressure column ("SEPHACRYL S-300") at a flow rate of approximately 1.0 mL/min using a peristaltic pump. The high molecular weight fractions were collected, pooled, and concentrated using a microconcentrator ("CENTRICON-30").

The relative fluorescence intensities of Dye 1, polymeric dye 11B, and polymeric dye 11D with excitation at 488 nm and emission at 614 nm are shown in FIG. 1. In FIGS. 1–9, fluorescence intensity, whether relative or corrected, is expressed in arbitrary units.

EXAMPLE II

Preparation Of Polymeric Dye 11D

Polymeric dye 11D was prepared as described in EXAMPLE I. Dye 1 was prepared as described in EXAMPLE I. The attachment of Dye 1 to polymeric entity 11A was effected by using EDAC as a dehydrating agent as described in EXAMPLE I.

Figure 2:
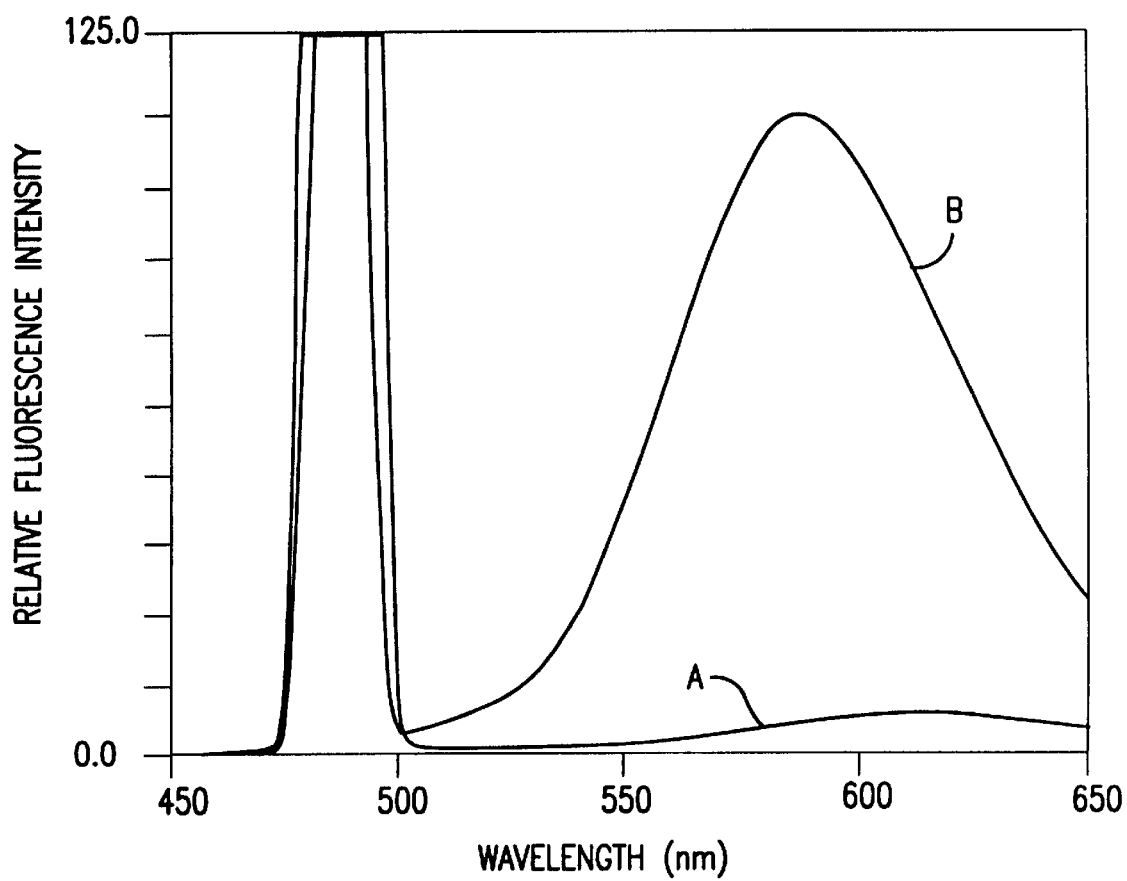
FIG. 2 compares fluorescence emission of polymeric dye 11B and polymeric dye 11D.
Figure 3:
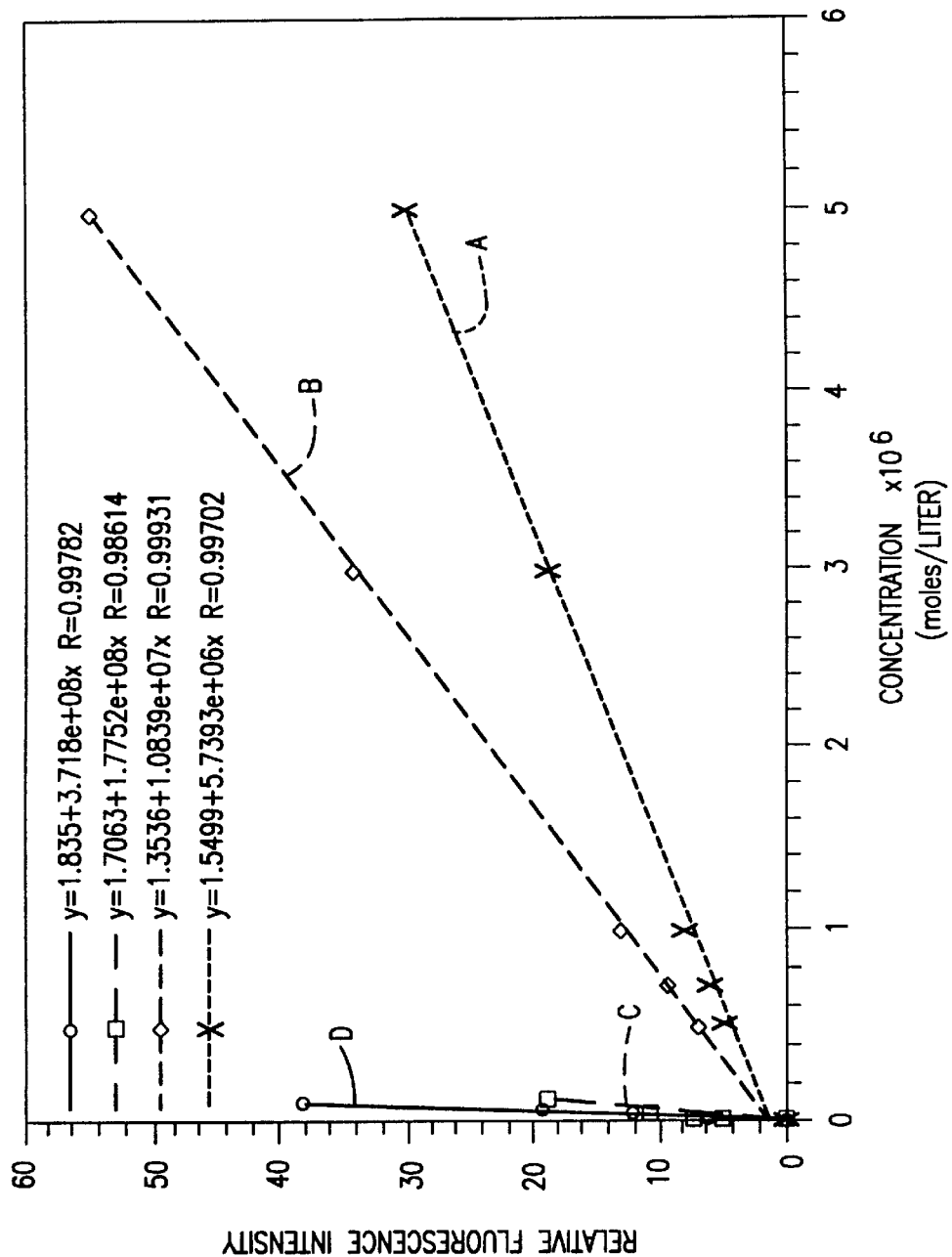
FIG. 3 shows response in fluorescence signal of polymeric dye 11D as a function of concentration of polymer.

Signal enhancement was improved substantially by the addition of cyclodextrin aldehyde 6 to the solution of polymeric dye 11B. Cyclodextrin and Dye 1 were attached to the acrylamide hydrazide polymeric backbone via the carboxylic group of the dye, as shown in Scheme 3. The resultant polymeric dye 11D, which had covalently attached cyclodextrin (via cyclodextrin aldehyde 6), can be diluted to provide linear response to concentration of polymeric dye as shown in FIG. 3. In FIG. 3, Curve A indicates the fluorescence intensity of polymeric dye 11B as a function of concentration, where the excitation wavelength is 488 nm and the emission wavelength is 580 nm; Curve B indicates the fluorescence intensity of polymeric dye 11B as a function of concentration, where the excitation wavelength is 488 nm and the emission wavelength is 614 nm; Curve C indicates the fluorescence intensity of polymeric dye 11D as a function of concentration, where the excitation wavelength is 488 nm and the emission wavelength is 580 nm; Curve D indicates the fluorescence intensity of polymeric dye 11D as a function of concentration, where the excitation wavelength is 488 nm and the emission wavelength is 614 nm. A comparison of relative fluorescence intensity as a function of wavelength is shown in FIG. 2. In FIG. 2, Curve A indicates the relative fluorescence intensity of polymeric dye 11B as a function of wavelength; Curve B indicates the relative fluorescence intensity of polymeric dye 11D as a function of wavelength.

Scheme 3
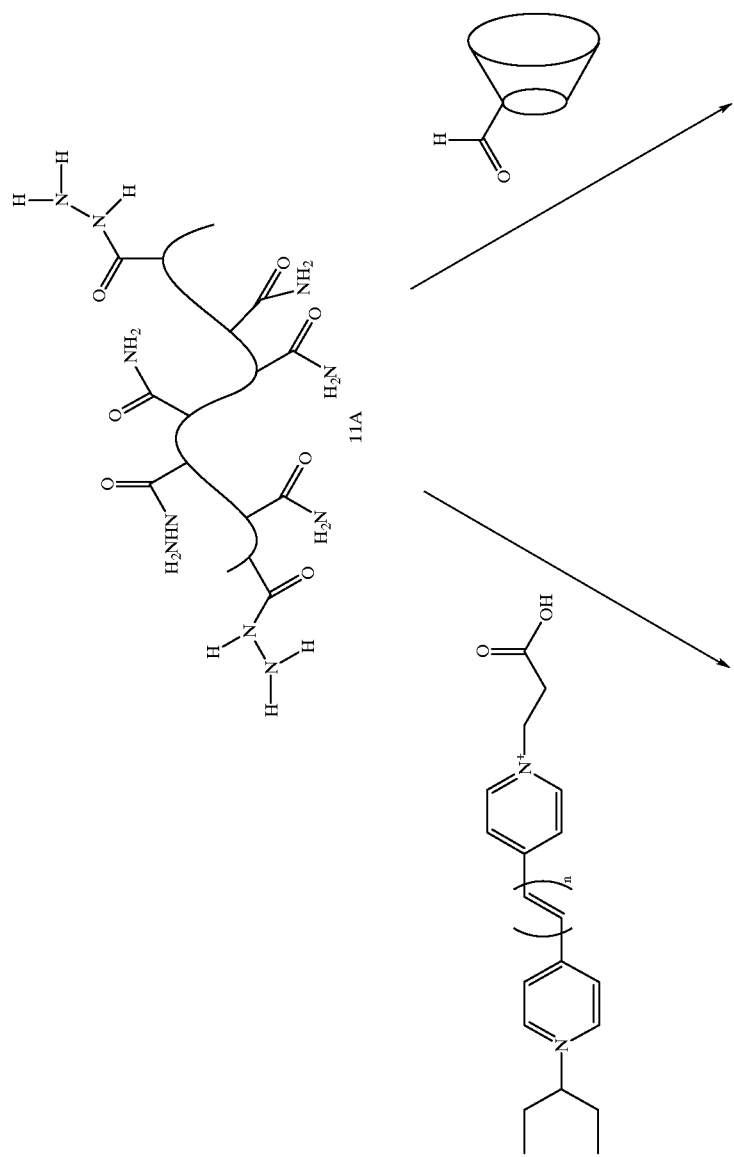

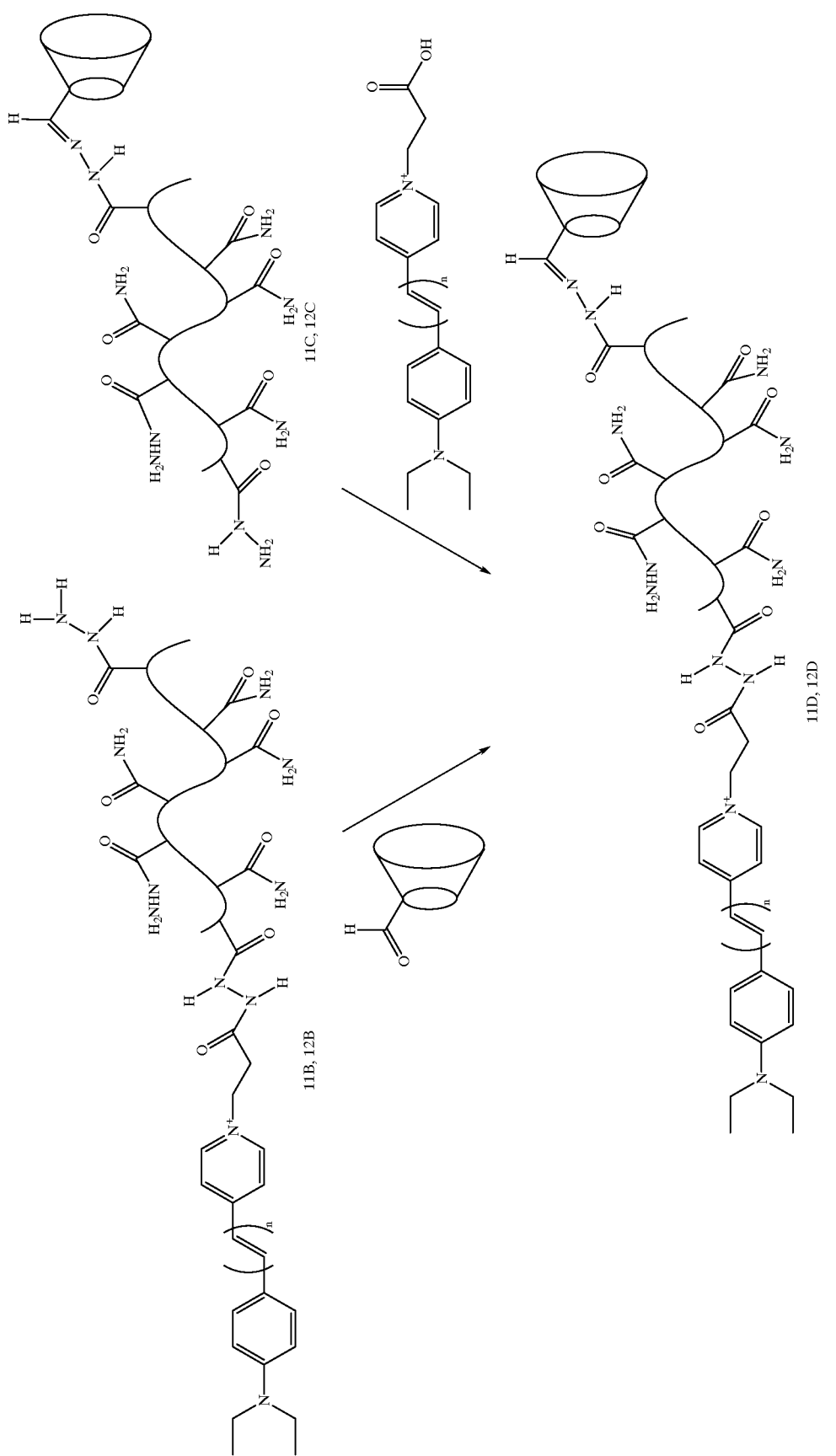

In polymeric dyes 11B and 11D, n=1. In polymeric dyes 12B and 12D, n=2.

EXAMPLE III

Preparation Of Cyclodextrin Derivative Of Acrylamide Hydrazide Pyridinium Aniline Diene Polymer Dye 3 was prepared by reacting trans-4-(diethylamino) cinnamaldehyde with Synthetic Intermediate I in the presence of base. Polymeric dye 12B was prepared by reaction of Dye 3 at the carboxyl substituent with a hydrazine moiety of polymer 11A using EDAC as a dehydrating agent. The resultant polymeric dye 12B was further reacted with cyclodextrin aldehyde 6 to produce the polymeric dye 12D.

Preparation Of Dye 3

A reaction mixture was prepared by combining trans-4-(diethylamino)cinnamaldehyde (0.43 g, Aldrich Chemical Company, Milwaukee, Wis.), Synthetic Intermediate 1 (0.62 g), and piperidine (1 mL) in methanol (10 mL). The reaction mixture was heated to a temperature of 110° C. and maintained at that temperature for ½ hour, and then was cooled on an ice bath (0° C.). The methanol solvent was removed by filtration onto a sintered glass funnel. The resultant precipitate was washed with diethyl ether. The solid product was then purified either by preparative HPLC on a C-8 reverse phase column eluted with 70:30 methanol/water liquid phase or by precipitation with diethyl ether. The preparation is illustrated in Scheme 4.

chromatography on a column ("SEPHADEX G-25") in phosphate buffer that contained 100 mM phosphate and 100 mM NaCl, pH 7.0 (hereinafter "Buffer No. 2"). The void volume material that contained the polymeric dye was collected and was concentrated using a microconcentrator ("CENTRICON-30 ") to approximately 1.5 mL.

Example IV

Preparation Of Polymeric Dye 12B

Polymeric dye 12B was also prepared in the following manner: Polymer 11A (10.0 mg, Sigma Chemical Co., catalog #P-9905, MW 180,000) was dissolved in a Buffer No. 1 (2.0 mL) by means of magnetic stirring for at least 8 hours at room temperature (25° C.). Dye 3 (2.9 mg, 0.0536 mmole, 150 molar equivalents of dye per mole of polymer) was dissolved in N,N-dimethyl formamide (200 μL) to form a stock solution The entire stock solution containing Dye 3 was then added to the solution containing polymer 11A with stirring. Finally, four aliquots (250 mg each) of solid EDAC were added to the stirred reaction mixture at the initial time, and at times of ½ hour, 2 hours, and 3 ½ hours. The reaction mixture was stirred for 3 to 4 additional hours.

Polymeric dye 12B was purified by size exclusion chromatography on a column ("SEPHADEX G-25") in Buffer No. 2. The void volume material was collected and polymeric dye 12B was then concentrated using a microconcentrator ("CENTRICON-30") to approximately 1 to 2 mL.

Figure 4:
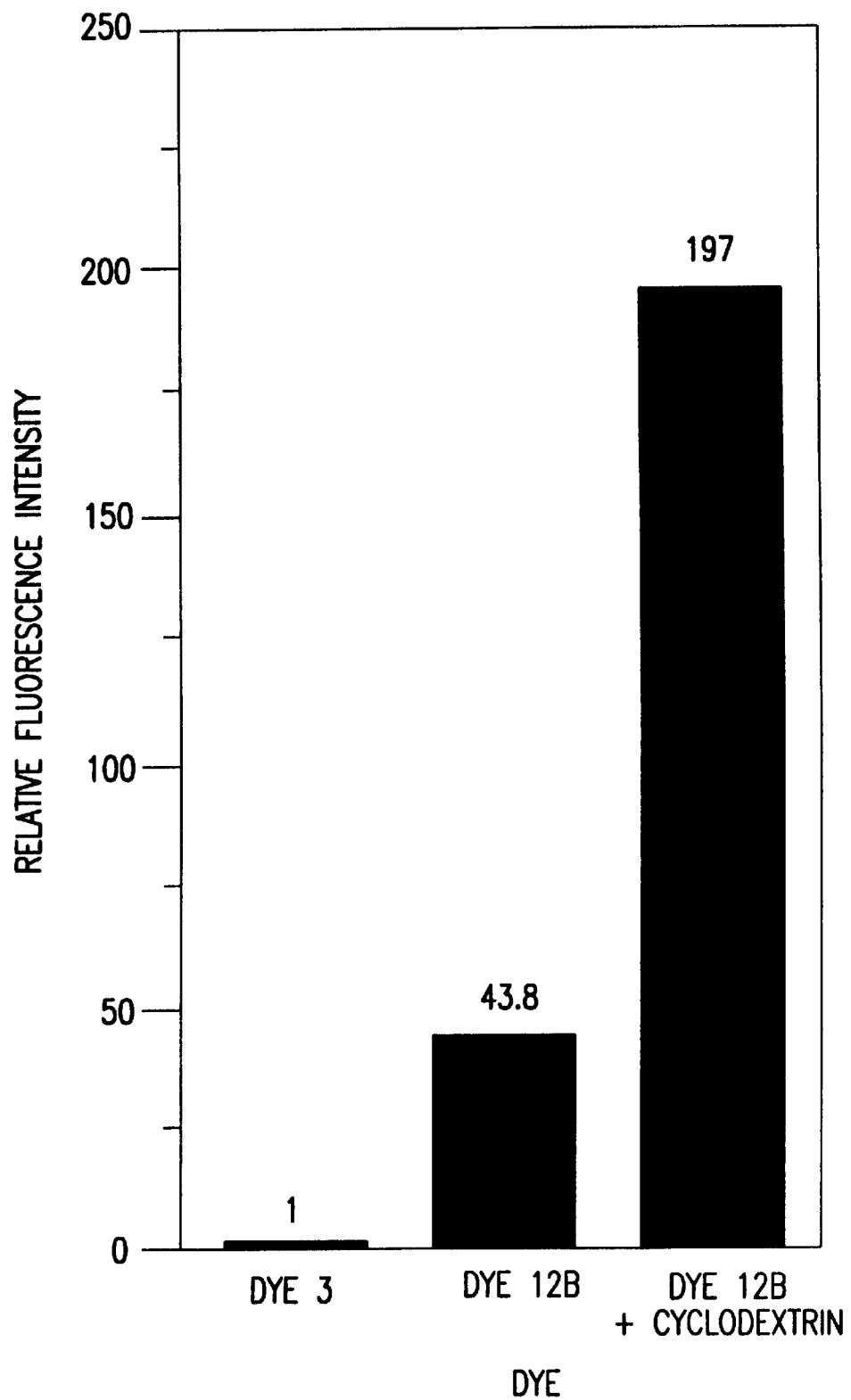
FIG. 4 shows response in fluorescence signal of polymeric dye 12B free of cyclodextrin and in the presence of cyclodextrin that is not covalently bonded to the polymeric entity.

A comparison of the relative fluorescence intensity of Dye 3, polymeric dye 12B, and polymeric dye 12B in the presence of 0.1 M cyclodextrin is shown in FIG. 4.

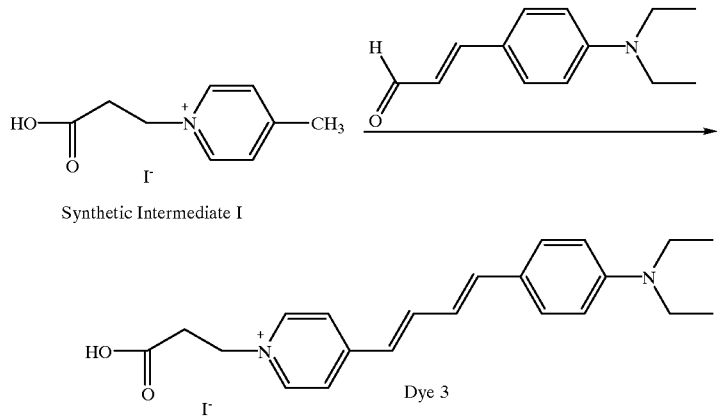

Scheme 4

Preparation Of Polymeric Dye 12B

Polymer 11A (4 mg, Sigma Chemical Company, catalog #P-9905, MW 180,000) was dissolved in Buffer No. 1 (2.0 mL) by means of magnetic stirring for at least 8 hours at room temperature (25° C.). Dye 3 (1.45 mg, 0.0268 mmole, 75 molar equivalents of the dye per mole of polymer) was dissolved in N,N-dimethylformamide (DMF) (200 μL) to form a stock solution, and the resulting stock solution was then added to the reaction mixture containing polymer 11A with stirring. Four aliquots (50 μL each) of an EDAC stock composed of 2.37 mg EDAC dissolved in 200 μL of Buffer No.1 were added at ½ hour intervals (2.5 molar equivalents of EDAC per mole of dye for each aliquot) to the reaction mixture. The reaction mixture was stirred for from 3 to 4 hours, and the polymeric dye was purified by size exclusion

Preparation Of Polymeric Dye 12D

Polymeric dye 12B was reacted with cyclodextrin aldehyde to yield polymeric dye 12D. Polymeric dye 12B (250 μL at a concentration of 1.1 mg/mL) was reacted with cyclodextrin aldehyde (1.5 mg, prepared as described in Huff, J. B., Bieniarz, C., J. Org. Chem., 1994, 59, 7511–7516) at a final concentration of 6.0 mg/mL of cyclodextrin in Buffer No. 1. The reaction was conducted for about four hours at ambient temperature in the dark. The resultant polymeric dye 12D was then purified by size exclusion chromatography ("SEPHADEX G-25"), and the void volume fractions were pooled and concentrated using a microconcentrator ("CENTRICON-30").

EXAMPLE V

Preparation Of Cyclodextrin Derivative Of Acrylamide Hydrazide Benzothiazolium Aniline Monoene Polymer Polymeric dye 17D was prepared by the reaction of cyclodextrin monoaldehyde with acrylamide hydrazide benzothiazolium aniline monoene polymer. The latter polymer, in turn, was made by reaction of Dye 2 with polymer 11A using EDAC as a dehydrating agent. Dye 2 was synthesized by the condensation of Synthetic Intermediate V and trans-4-(diethylamino)cinnamaldehyde in the presence of piperidine, and the appropriate structural adduct was isolated from the reaction mixture by HPLC. Alternatively, Dye 2 can be prepared by the condensation of 2-methylbenzothiazolium compound intermediate (hereinafter "Synthetic Intermediate V") and 4-(diethylamino)benzaldehyde in the presence of piperidine.

The synthesis of Dye 2 is illustrated in Scheme 5.

Scheme 5
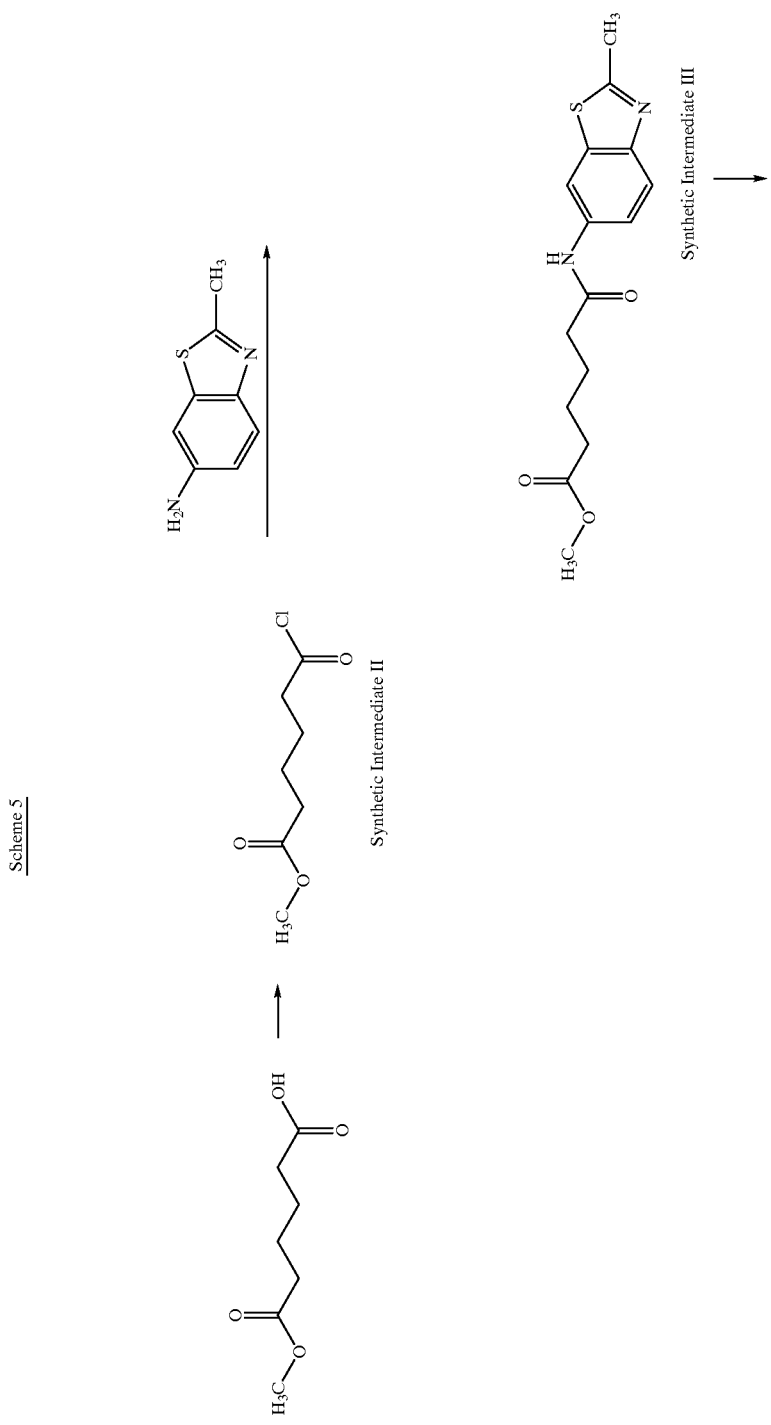

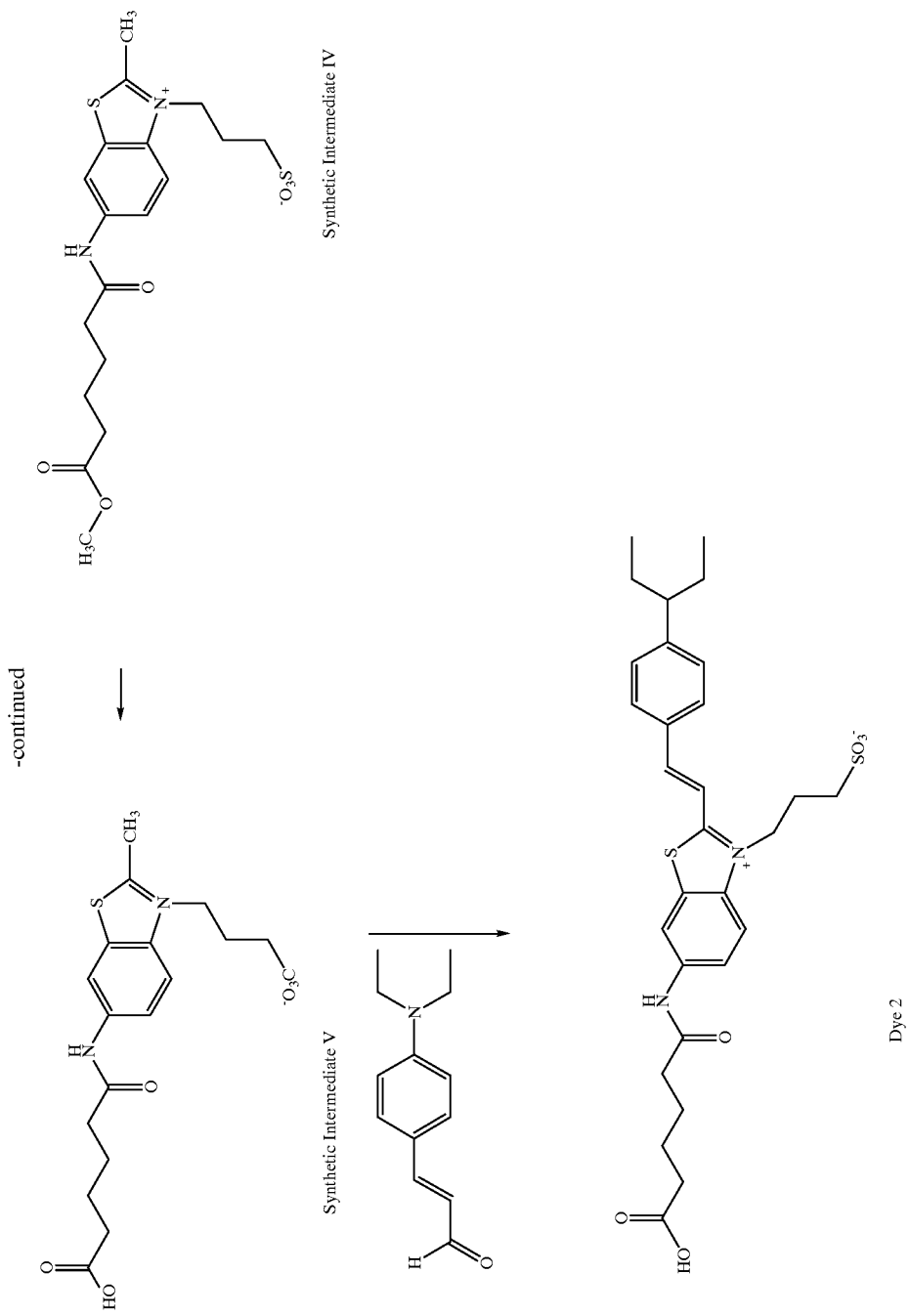

Preparation Of Synthetic Intermediate V

Adipic acid monoethyl ester (17.42 g, Aldrich Chemical Co., St. Louis, Mo.) was reacted with $SOCl_2$ (9.0 mL, Aldrich Chemical Co., St. Louis, Mo.) by refluxing a reaction mixture composed of the two compounds in the presence of a drop of N,N-dimethyl formamide as a catalyst for the reaction. The reaction mixture was heated to a temperature of 90° C. and maintained at that temperature for ½ hour. The bulk of the excess $SOCl_2$ was removed in vacuo. Then a minimal amount of diethyl ether was added to the mixture, and the mixture was heated in vacuo to remove the $SOCl_2$/diethyl ether azeotrope. This step involving azeotrope removal was repeated twice. The remaining traces of thionyl chloride and diethyl ether were then removed via exposure to high vacuum for one hour. Synthetic intermediate II was isolated as an oil and was used without further purification.

Synthetic Intermediate II (5.83 g) and 5-amino-2-methylbenzothiazole (6.0 g, Aldrich) were dissolved in pyridine with dimethylaminopyridine (0.46 g) as an acylation catalyst. The reaction mixture was heated for several hours at a temperature of 110° C. The bulk of the pyridine solvent was removed in vacuo, and the remaining traces were removed by pyridine/$CH_2Cl_2$ azeotrope. The reaction mixture was partitioned into $CH_2Cl_2$ and saturated $NaHCO_3$. The organic layer was dried over anhydrous $Na_2SO_4$, filtered, and the solvent was removed in vacuo. The residue was dissolved in a minimal amount of $CH_2Cl_2$ and diethyl ether was added. The precipitate was filtered off and discarded. The filtrate was collected, and the solvent was removed in vacuo to yield crystalline Synthetic Intermediate Ill.

The amide Synthetic Intermediate III (7.4 g) was dissolved in a minimal amount of acetonitrile, and 1,3-propane sultone (6.9 g) was added to the solution. The reaction mixture was refluxed for 72 hours until thin layer chromatography (TLC) indicated that no more starting material remained. The reaction product was then isolated by dissolving in methanol and precipitating with diethyl ether. A quaternized ester, Synthetic Intermediate IV, was recovered as a white solid.

The quaternized ester Synthetic Intermediate IV was hydrolyzed in 0.02 to 0.4 N HCl. The degree of hydrolysis was carefully monitored by TLC, and the hydrolysis was stopped at completion. The quaternized ester Synthetic Intermediate IV (0.30 g) was dissolved in 0.4 N HCl (30 mL). In an alternate method, the quaternized ester Synthetic Intermediate IV (0.5 g) was dissolved in 4.0 N HCl in lieu of 0.4 N HCl to achieve the same result. The 2-methylbenzothiazolium hydrolysis product, Synthetic Intermediate V, was isolated by first freezing the reaction mixture and then removing the solvent by use of a rotary evaporator at approximately 0.1 mm Hg pressure.

Preparation Of Dye 2

Synthetic Intermediate V (100 mg, 0.24 mmole) and trans-4-(diethylamino)cinnamaldehyde (50 mg, 0.24 mmole) were dissolved in methanol (4 ml) and piperidine (0.25 ml) was added to solution. The reaction mixture was heated to reflux for four hours. Excess solvent was removed, and the residue was redissolved in methanol. A solid material was precipitated with diethyl ether and was collected by filtration. The benzothiazolium aniline monoene, Dye 2, was dried on a vacuum pump overnight. If desired, the pure dye can be obtained by reversed phase HPLC chromatography, and the structure can be confirmed by [1] H NMR and mass spectral analysis.

In an alternative method, Synthetic Intermediate V (100 mg, 0.24 mmole) and trans-4-(diethylamino) cinnamaldehyde (0.24 mmole) can be dissolved in methanol (4 ml), and piperidine (0.25 ml) can be added to the solution. The reaction mixture can be heated to reflux for four hours. Excess solvent can then be removed, and the residue can be redissolved in methanol. The solid product can then be precipitated with diethyl ether and collected by filtration.

Preparation Of Polymeric Dye 17B

Polymeric dye 17B (a precursor to polymeric dye 17D) was synthesized by attachment of Dye 2 to polymer 11A using EDAC as a dehydrating agent. The preparation is shown in Scheme 6.

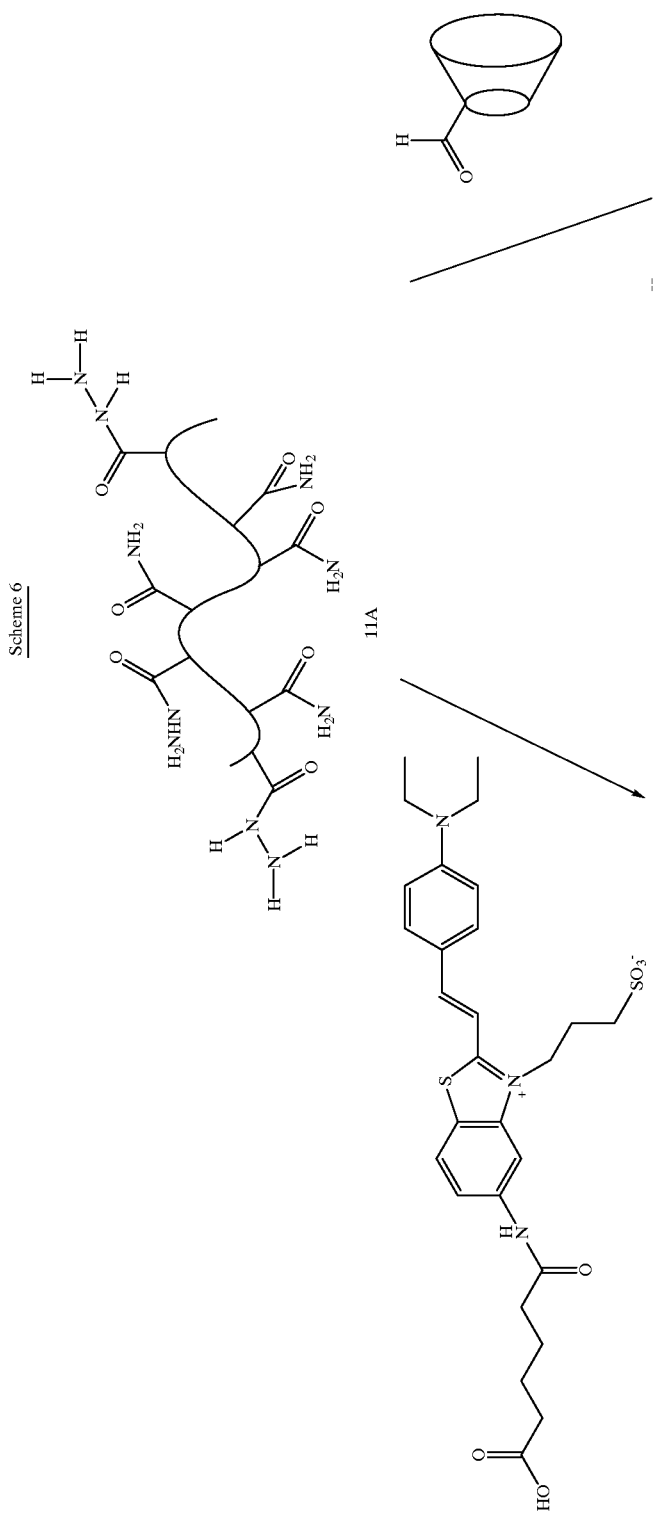

-continued
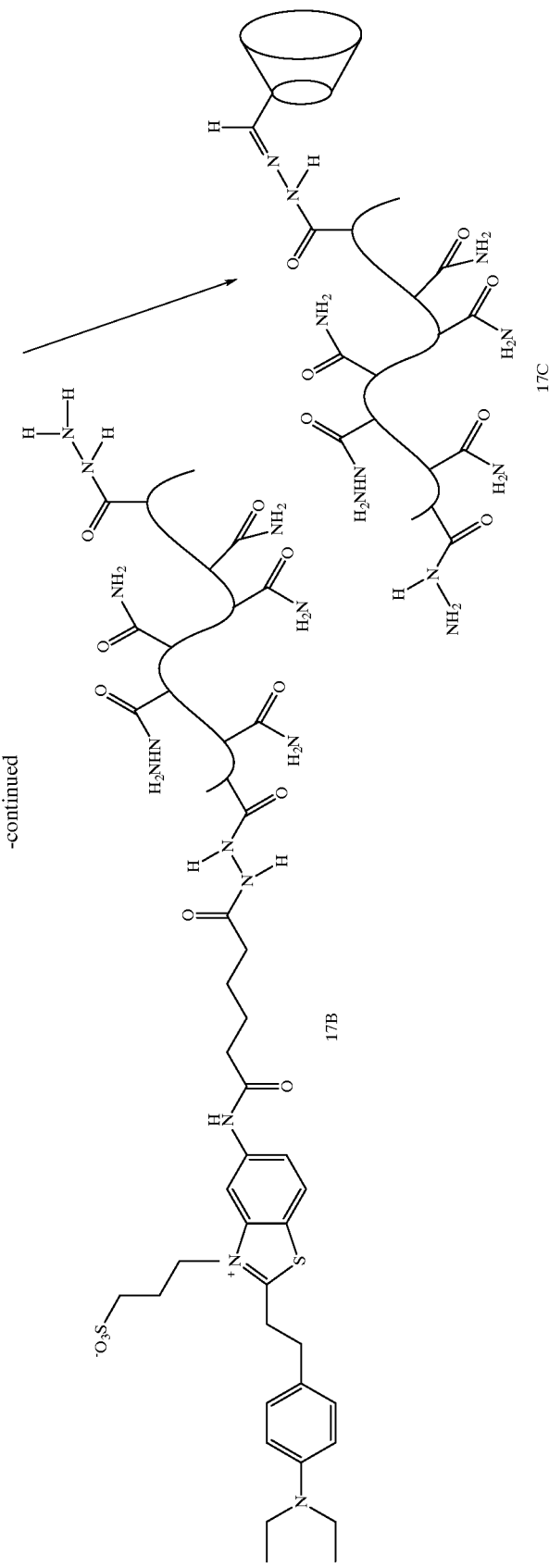

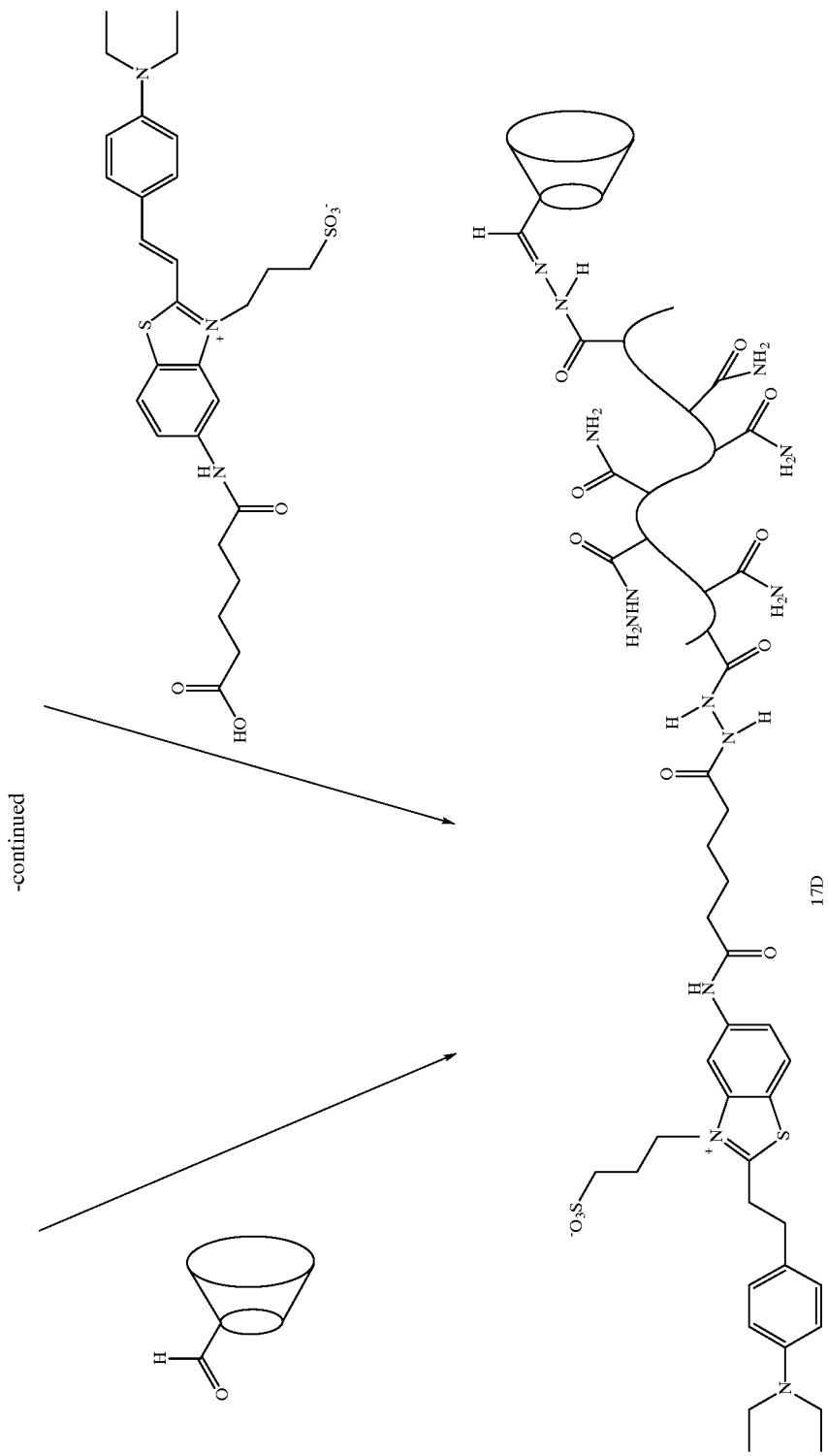

Polymer 11A (20 mg, Sigma Chemical Co., catalog # P-9505, MW 180,000) was dissolved in Buffer No. 1 (4.0 mL), to give a concentration of polymer of 5 mg/mL ($2.78 \times 10^{-8}$ mole polymer). Approximately 150 molar equivalents of Dye 2 (5.0 mg, $4.17 \times 10^{-6}$ mole) were added to the solution containing the polymer by dissolving Dye 2 (5.0 mg) in DMSO, and adding this solution to the buffered aqueous solution of the polymer. Five 300 mg aliquots of solid EDAC were added at approximately ½ hour intervals as the reaction mixture was stirred in the dark overnight.

The polymeric dye from the reaction mixture was separated from unbound dye by elution in Buffer No. 1 on a column ("SEPHADEX G-25"). The void volume fractions were collected (approximately 3.0 mL total volume), and the product was concentrated using a centrifugal microconcentrator ("CENTRICON-30").

Preparation Of Polymeric Dye 17D

Polymeric dye 17B was diluted to a concentration of 1.0 mg/mL in Buffer No. 1 to form as stock solution. An aliquot of polymeric dye 17B in solution (3.0 mL, 3.0 mg of polymer) was taken from the stock solution containing Polymeric dye 17B, and cyclodextrin aldehyde 6 (1.9 mg, prepared as described in Huff, J. B., Bieniarz, C., *J. Org. Chem.*, 1994, 59, 7511–7516) was added. The solution was allowed to incubate at room temperature (25° C.) for 72 hours in the dark. The resultant polymeric dye 17D was purified on a column ("SEPHACRYL S-300") by elution in Buffer No. 2 at a flow rate of approximately 1 to 3 mumin using a peristaltic pump. The high molecular weight fractions were collected (approximately 5.0 mL), pooled, and concentrated using a microconcentrator ("CENTRICON-30").

Figure 5:
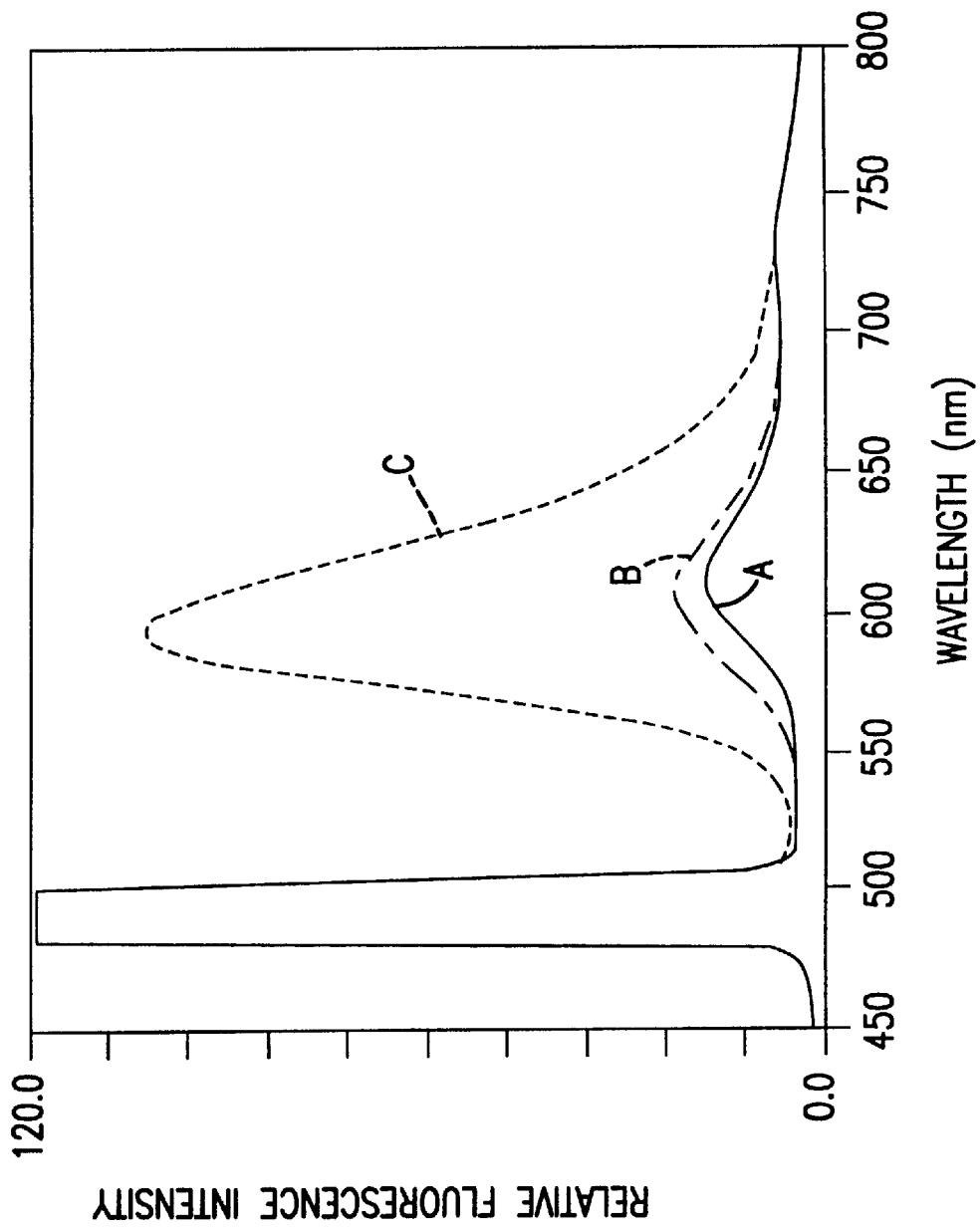
FIG. 5 compares fluorescence spectrum of polymeric dye 17B with cyclodextrin modification, without cyclodextrin modification, and with the addition of cyclodextrin that is not covalently bonded to the polymeric entity at identical cyclodextrin concentration of 0.25 mg/ml.
Figure 6:
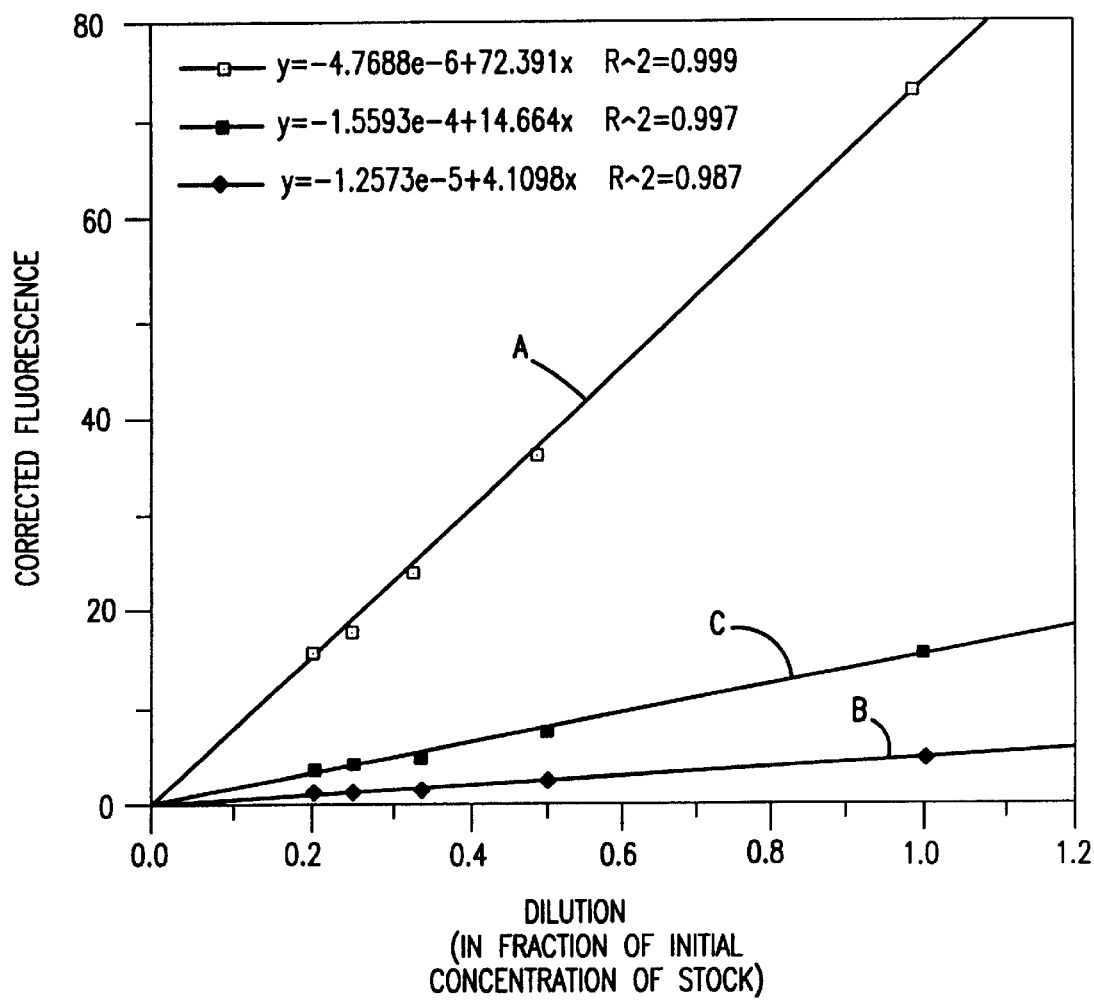
FIG. 6 shows fluorescence response of polymeric dye 17D as a function of concentration of polymeric dye 17D.

A comparison of fluorescence emission for polymeric dye 17B alone, polymeric dye 17B plus cyclodextrin not covalently bonded, and polymeric dye 17D (covalently attached cyclodextrin) is shown in FIG. 5. In FIG. 5, Curve A indicates the relative fluorescence intensity of polymeric dye 17B as a function of wavelength; Curve B indicates the relative fluorescence intensity of polymeric dye 17B plus cyclodextrin not covalently bonded as a function of wavelength; Curve C indicates the relative fluorescence intensity of polymeric dye 17D as a function of wavelength. FIG. 6 shows the dilution curves of polymeric dye 17D. These curves demonstrate a linear fluorescence response to concentration of polymeric dye 17D. Also included is the dilution curve for polymeric dye 17B alone and polymeric dye 17B in a 0.25 mg/ml cyclodextrin stock diluent. In FIG. 6, Curve A indicates fluorescence of polymeric dye 17D as a function of dilution of dye; Curve B indicates fluorescence of polymeric dye 17B as a function of dilution of dye; Curve C indicates polymeric dye 17B plus cyclodextrin not covalently bonded as a function of dilution of dye.

EXAMPLE VI

Preparation Of Cyclodextrin Derivative Of Acrylic Acid Pyridinium Aniline Monoene Polymer 13D Dye 4 was covalently bonded to acrylic acid polymer by using EDAC methodology. Cyclodextrin monoamine 7 was covalently bonded to acrylic acid pyridinium aniline monoene polymer using EDAC methodology.

Preparation Of Dye 4

4-Methyl pyridine (10 g) was reacted with 3-bromopropylphthalimide (28.8 g) in ethanol solvent (20 mL) as the reaction mixture was heated to 100° C. and held at that temperature for 20 minutes. The N-quaternized species of N-(3-phthalimidopropyl) -4-methylpyridinium bromide (hereinafter "Synthetic Intermediate VI") was purified by removing the solvent in vacuo and redissolving the residue in methanol. This solution was then titrated with diethyl ether and cooled to a temperature of from 2 to 8° C. until precipitate had formed. The precipitate (23.3 g, Synthetic Intermediate VI) was then separated by filtration. Preparation of Synthetic Intermediate VI is illustrated in Scheme 7.

Scheme 7

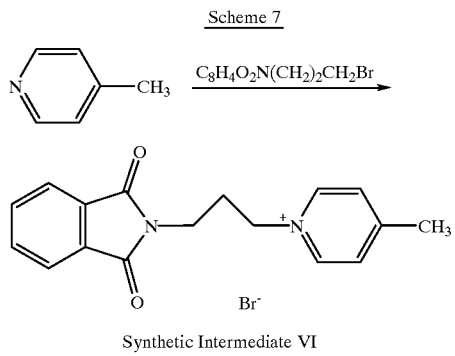

Synthetic Intermediate VI

Synthetic Intermediate VI (5.0 g) was dissolved in pyridine (10 mL). 4-(diethylamino)benzaldehyde (7 g, Aldrich Chemical Co.) was added to the reaction mixture. The resultant suspension was then solubilized by the addition of anhydrous ethanol (4 mL). This reaction mixture was stirred for four hours at a temperature of 100° C., and the solvent was removed in vacuo. The imide intermediate was purified by silica gel column chromatography eluted with a mixture of $CH_2Cl_2$ (95% by volume)/methanol (5% by volume). The imide intermediate was hydrolyzed to free amine compound Dye 4 by refluxing in concentrated HCl (30 mL) for five hours. The acidic reaction mixture was cooled to room temperature, and the remaining solvent was removed in vacuo. The residue was purified to provide Dye 4 by preparative HPLC using a C-8 reversed phase column and methanol with 0.5% trifluoroacetic acid as the mobile phase. Preparation of this dye is illustrated in Scheme 8.

Scheme 8

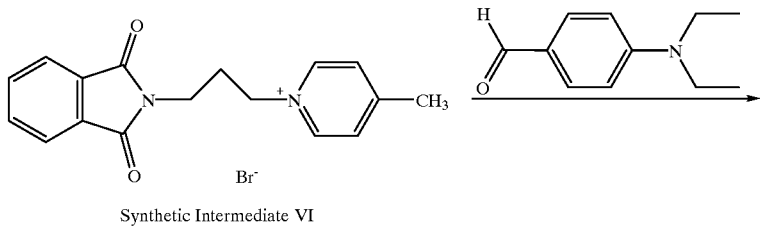

Synthetic Intermediate VI

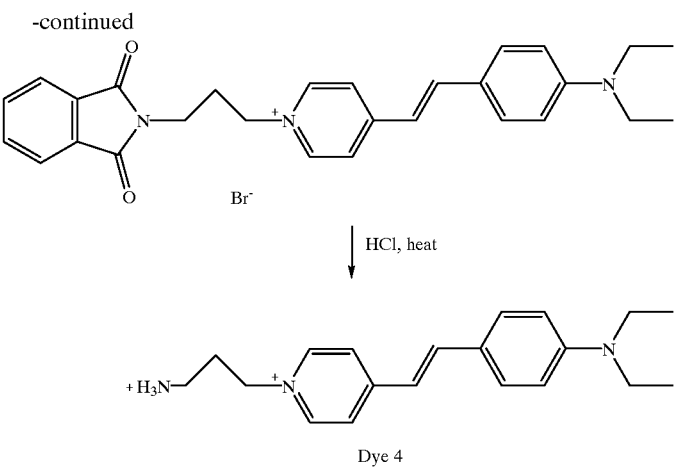

Dye 4

Preparation Of Cyclodextrin Monoamine

Cyclodextrin amine was prepared as illustrated in Scheme 9.

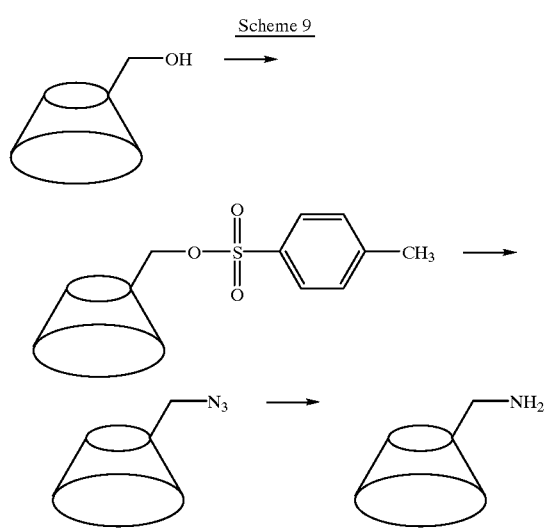

Scheme 9

Preparation Of Cyclodextrin Monotosylate

Beta-cyclodextrin was obtained from the Aldrich Chemical Company. Cyclodextrin monotosylate was prepared as described in Petter, R. C., Salek, J. S., Sikorski, C. T., Kumaravel, G., Lin, F.-T., *J. Amer. Chem. Soc.* 1990, 112, 3360–3368, incorporated herein by reference.

Preparation Of Cyclodextrin Monoazide

A reaction mixture was prepared by the addition of beta-cyclodextrin tosylate (3.06 g) and sodium azide (0.76 g) to dimethyl formamide solvent (60 mL). The resulting mixture was heated to a temperature of 80° C. and held at that temperature overnight, and then concentrated in vacuo. The concentrated residue was filtered through reversed phase (C-18) silica (40 g, Fluka, #60756) in a sintered glass funnel. Unreacted cyclodextrin monotosylate was washed from the C-18 silica with water, and the cyclodextrin monoazide product was removed from the C-18 silica by washing though the column with a mixture of acetonitrile (50% by volume) and water (50% by volume) followed by washing through the column with acetonitrile (100%). Fractions from the C-18 silica washings were checked by normal phase TLC using a solvent mixture of isopropanol (55% by volume)/ammonium hydroxide (35% by volume)/water (10% by volume). The ammonium hydroxide was concentrated ammonium hydroxide in water. The C-18 silica wash fractions that were free of monotosylate, as determined by TLC, were combined and concentrated under reduced pressure. The concentrated material was dissolved in methanol, and the product, cyclodextrin monoazide, was precipitated with diethyl ether. The solid cyclodextrin monoazide product was then filtered and washed with diethyl ether.

Preparation Of Cyclodextrin Monoamine 7

Cyclodextrin monoazide (0.51 g) was dissolved in water (50–100 mL). Carbon containing 5% palladium (150 mg) was added to the solution under a nitrogen atmosphere. The carbon/palladium catalyst did not dissolve. The reaction suspension was placed under a hydrogen atmosphere and shaken overnight (at 20 psi $H_2$ pressure) in a shaker/hydrogenator ("PARR"). The reaction mixture was monitored by normal phase TLC using a mixture of isopropanol (55% by volume)/ammonium hydroxide (35% by volume)/water (10% by volume) as a developing solvent. The ammonium hydroxide was concentrated ammonium hydroxide in water. The reaction mixture was filtered through a filter aid ("CELITE") two times. After confirming the lack of unreacted starting material in the reaction mixture, the aqueous filtrate was concentrated in vacuo, and cyclodextrin monoamine (0.28 g) was obtained. An additional wash of the reaction residue on filter aid ("CELITE") with water (500 mL) followed by concentration yielded additional cyclodextrin monoamine (0.057 g). Both batches of product were combined and used without further purification for the preparation of polymeric dyes 13D, 15D, and 18D.

Preparation Of Acrylic Acid Pyridinium Aniline Monoene Polymer (Polymeric Dye 13B)

A stock solution of acrylic acid polymer 13A (about 200,000 MW, Polysciences, Warrington, Pa.) was prepared by dissolving acrylic acid polymer in deionized water at a concentration of 20 mg/mL. A reaction mixture was prepared by combining a 1 mL aliquot of the stock solution of acrylic acid polymer and Dye 4 (0.68 mg, 20 mole equivalents). Aliquots of solid EDAC (3.3 mg each) were added at ½ hour intervals in five increments over a two hour period while the reaction mixture was stirred continuously. The resultant polymeric dye 13B was purified by collection of the void volume on a size exclusion column (100–300 mesh, "SEPHADEX G-25").

Preparation Of Cyclodextrin Derivative Of Acrylic Acid Pyridinium Aniline Monoene Polymer (Polymeric Dye 13D)

A reaction mixture containing Dye 4 (0.68 mg), cyclodextrin monoamine 7 (4.0 mg), and a solution of acrylic acid polymer (1.0 mL, 20 mg/mL) in deionized water was prepared. Five aliquots of EDAC (10 mg each) were added to the reaction mixture over a period of two hours. The mixture was stirred continuously. The resultant polymeric dye was purified by size exclusion chromatography ("SEPHADEX G-25"). The void volume fractions were combined and concentrated to 3.0 mL using a centrifugal concentrator ("CENTRIPREP-30"). The mixture was frozen using a dry ice/acetone bath, and subsequently lyophilized to obtained the pure solid polymeric dye 13D. Preparation of polymeric dye 13D is illustrated in Scheme 10.

Figure 7:
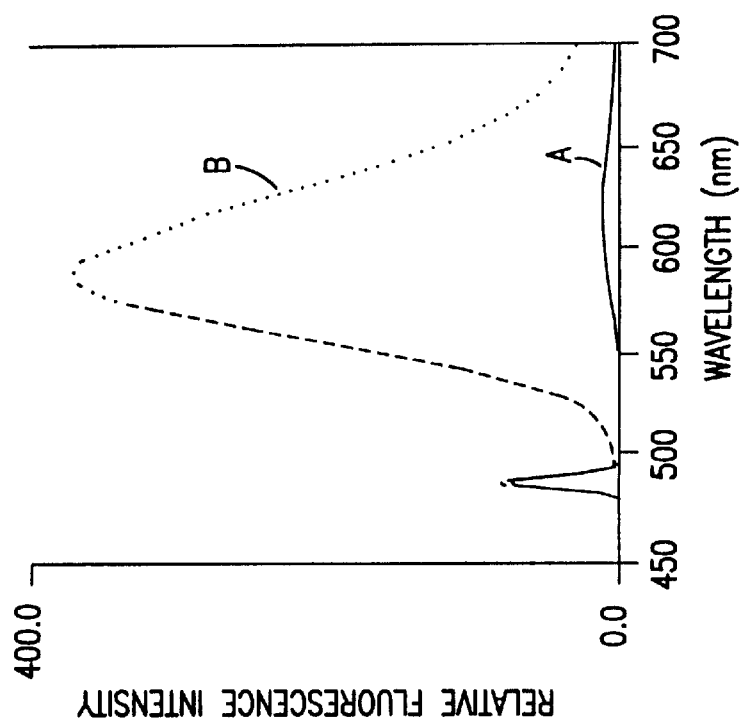
FIG. 7 compares fluorescence of purified polymeric dye 13B with purified cyclodextrin amine modified polymeric dye 13D at excitation wavelength of 488 nm.

FIG. 7 compares the fluorescence of purified polymeric dye 13B at $1.1 \times 10^{-7}$ M (Curve A) with purified polymeric dye 13D at $1.1 \times 10^{-7}$ M (Curve B) (both using 488 nm excitation).

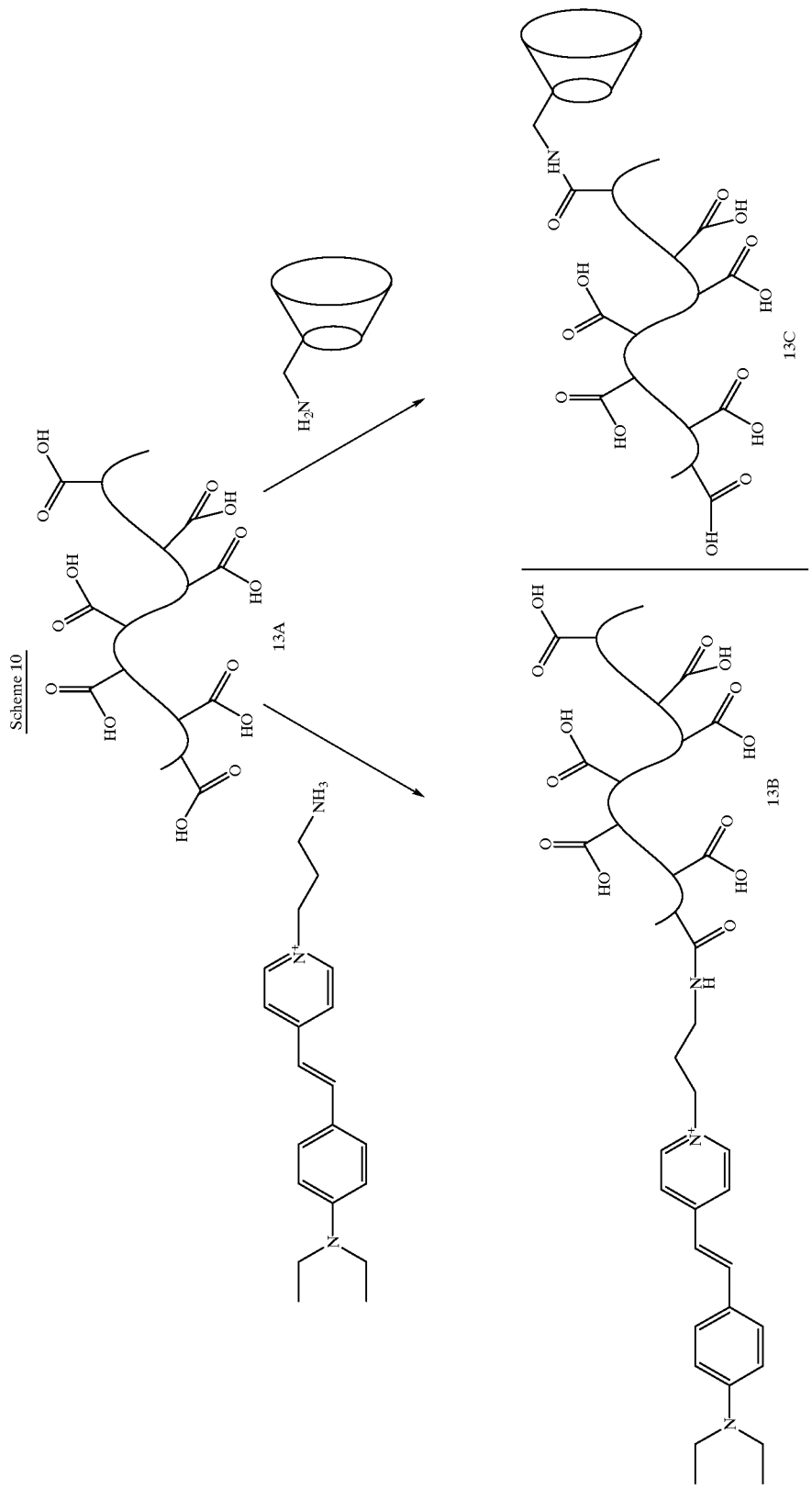

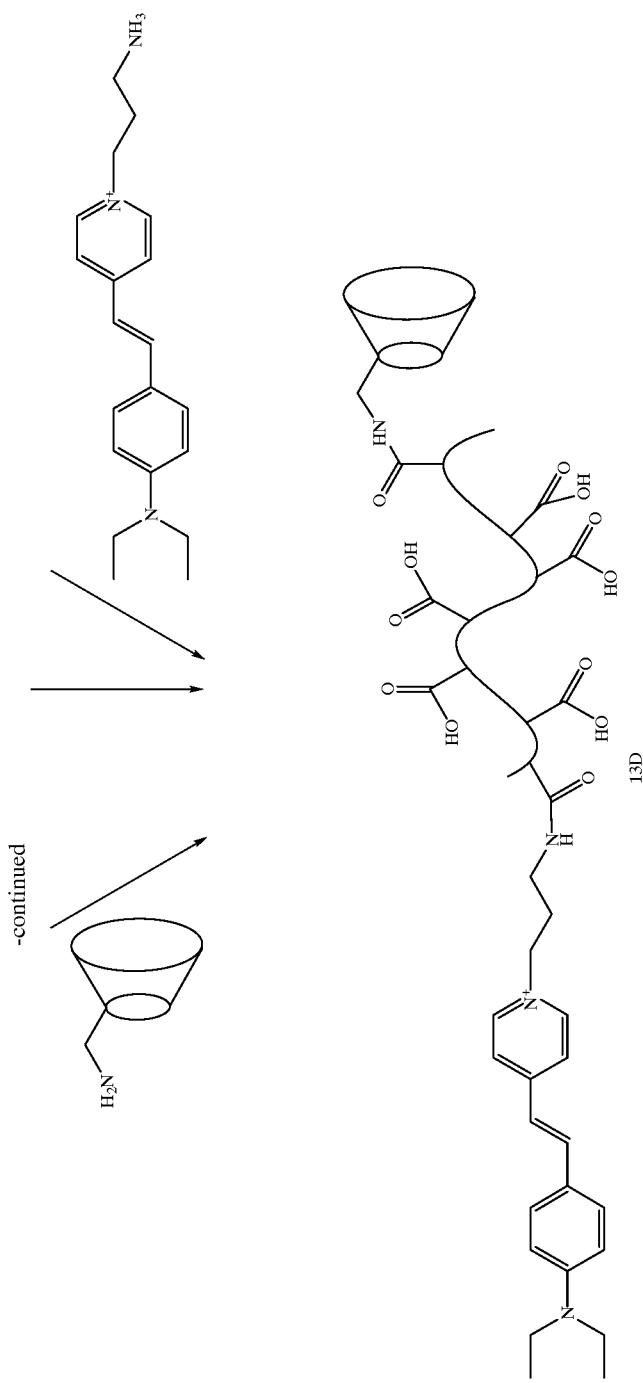

EXAMPLE VII

Preparation Of Permethylcyclodextrin Derivative Of Acrylic Acid Pyridinium Aniline Monoene Polymer Both permethylcyclodextrin 8 and Dye 4 were covalently bonded to acrylic acid polymer by using EDAC methodology.

Preparation Of Permethylcyclodextrin Monoazide

Beta-cyclodextrin was obtained from the Aldrich Chemical Company. The cyclodextrin monotosylate was prepared as described in Petter, R. C., Salek, J. S., Sikorski, C. T., Kumaravel, G., Lin, F.-T., *J Amer. Chem. Soc*, 1990, 112, 3360-. The cyclodextrin monotosylate was then converted to the cyclodextrin monoazide as described in Example VI and then converted into the permethylcyclodextrin monoazide in the following manner.

Beta-cyclodextrin monoazide (0.242 g, 0.2 mmole) was suspended in a mixture containing 3.5 mL dimethylformamide and 3.5 mL dimethylsulfoxide, and the resulting suspension was stirred for ½ hour until the stirred suspension was observed to be clear. Then, BaO (1.95 g) and Ba(OH)$_2$.8H$_2$O (1.95 g) were added to the suspension in successive portions. The suspension was cooled to a temperature of 0° C. using an ice bath. Dimethyl sulfate (3.3 mL, 34 mmoles) was added to the suspension over a period of one hour. The reaction mixture was stirred for 48 hours at a temperature of 2–8° C. The reaction was quenched by the addition of concentrated ammonium hydroxide (10 mL), and the remaining solvent was removed under reduced pressure. The remaining solid was stirred in one liter of CHCl$_3$, and the resulting suspension was filtered. The resultant solid was then once again washed with CHCl$_3$ (one liter). The CHCl$_3$ extracts were combined, reduced to a minimum volume by removing most of the CHCl$_3$ under reduced pressure and adding hexane (1 L) to give permethylcyclodextrin monoazide (140 mg).

Preparation Of Permethylcyclodextrin Monoamine

Permethylcyclodextrin monoazide (100 mg) was dissolved in water (20 mL). Then, solid carbon containing 10% palladium (30 mg) was added, and the reaction mixture was shaken vigorously overnight using a "PARR" shaker under a hydrogen atmosphere at about 20 psi pressure. The resultant product was filtered through a filter aid ("CELITE"), and the filtrate was concentrated under reduced pressure to yield the product permethylcyclodextrin monamine 8. Permethylcyclodextrin monoamine 8 was prepared as illustrated in Scheme 11.

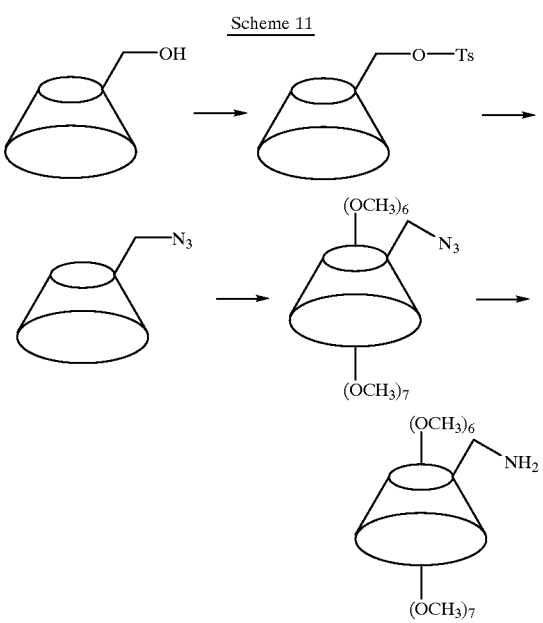

Scheme 11

Preparation Of Permethylcyclodextrin Derivative Of Acrylic Acid Pyridinium Aniline Monoene Monoamine Polymer (Polymeric Dye 14D)

Dye 4 was prepared in the manner previously described. Polyacrylic acid (5 mg) was dissolved in deionized water (0.25 mL). To this solution were added Dye 4 (3.4 mg) and permethylcyclodextrin monoamine 8 (24 mg). Five aliquots of EDAC (each 52 mg) were added to the reaction mixture, each aliquot being added at a ½ hour interval. The resulting product was purified by centrifugation ("CENTRIPREP-30") followed by repeated washes with fresh deionized water until no remaining dye passed through the membrane. Preparation of polymeric dye 14D is illustrated in Scheme 12.

Scheme 12
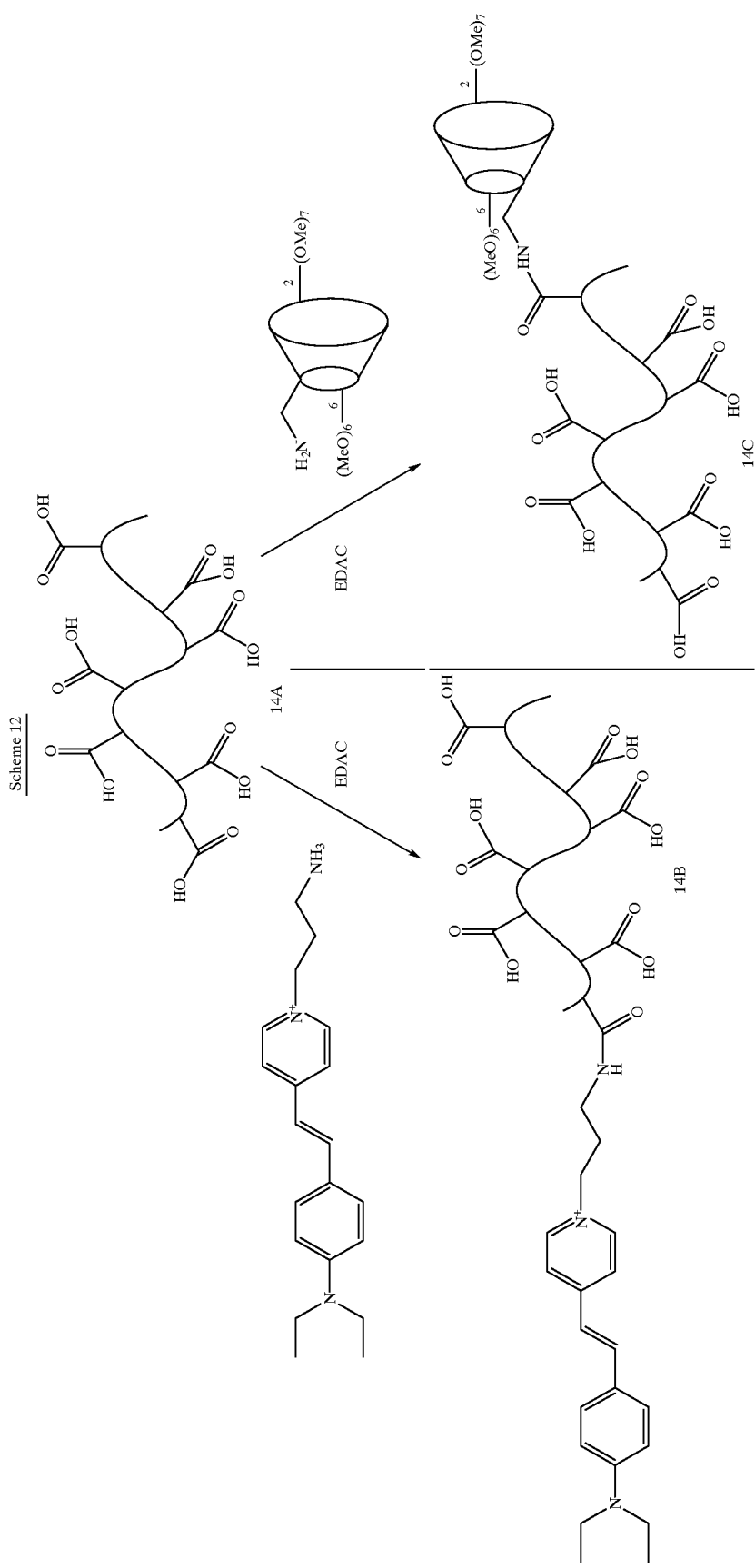

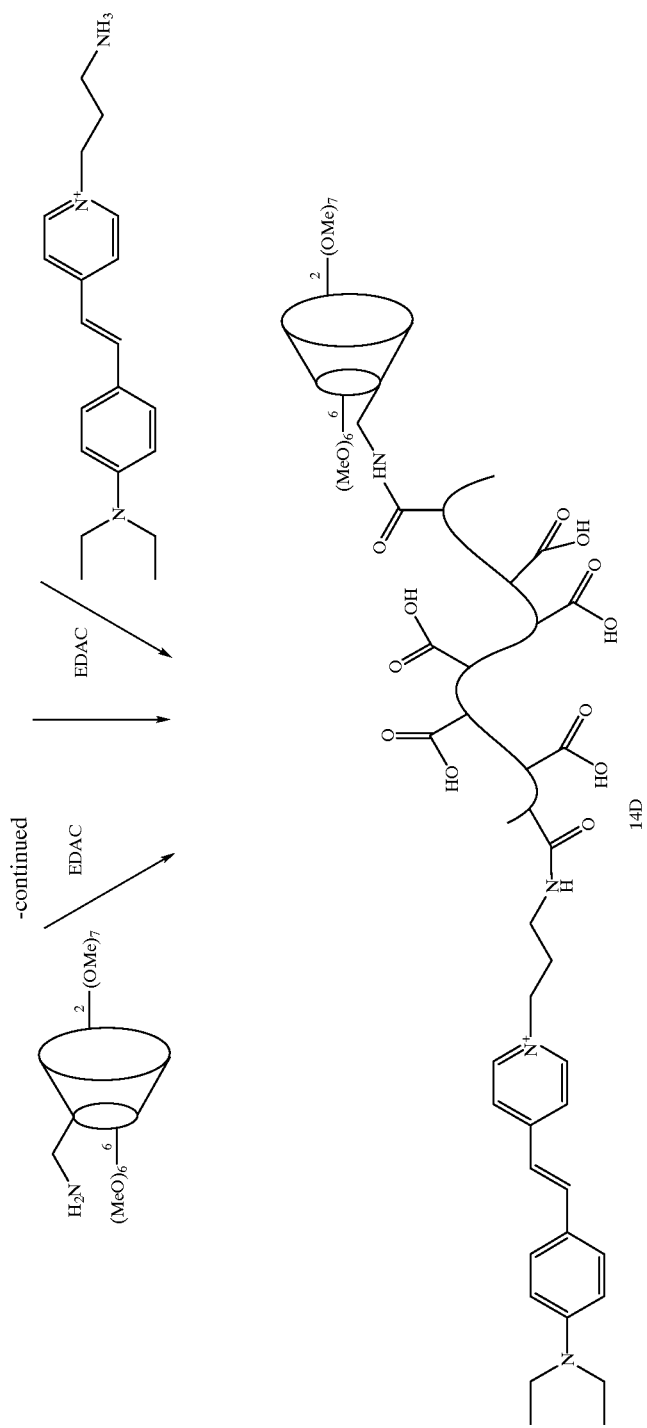

Figure 8:
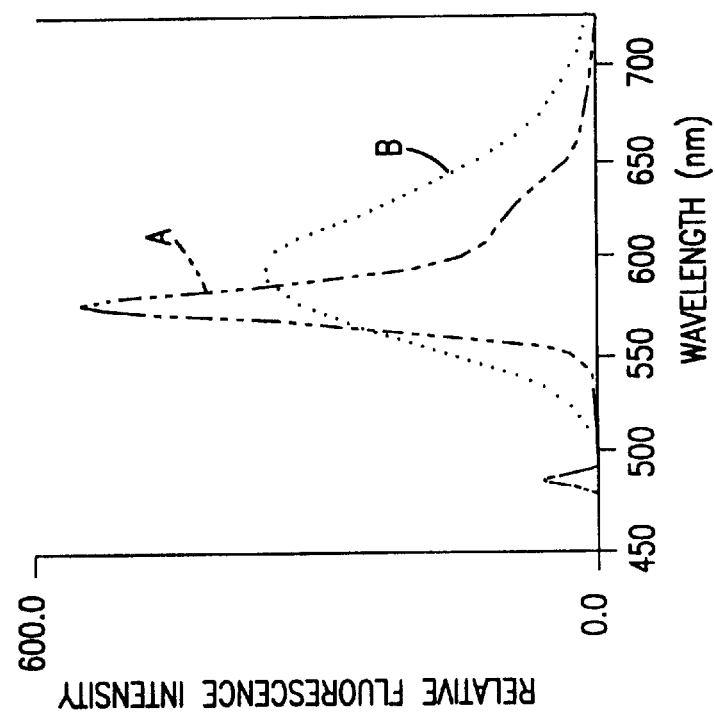
FIG. 8 compares fluorescence of natural phycobilliprotein phycoerythrin and polymeric dye 14D on a mole to mole basis at excitation wavelength of 488 nm.

The resultant polymeric dye 14D was then tested for fluorescence and its intensity was compared with the intensity of phycobilliprotein phycoerythrin. FIG. 8 shows the results of the fluorescence test comparing the fluorescence of polymeric dye 14D (Curve A) and phycoerythrin (Curve B) at the same concentration.

Figure 9B:
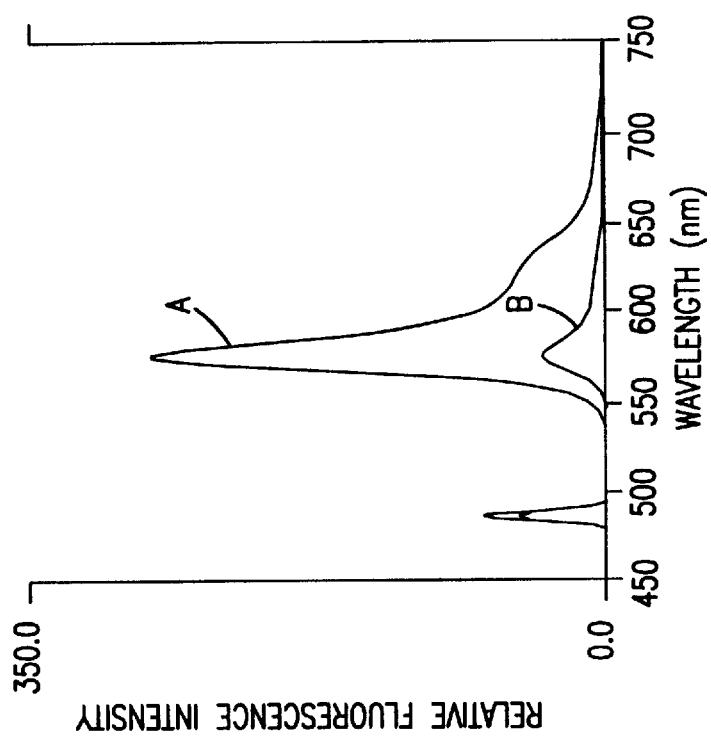
FIGS. 9A and 9B compare stability of polymeric dye 14D after 16 hours exposure to ambient room light with stability of phycoerythrin after 16 hours exposure to the same ambient room light.
Figure 9A:
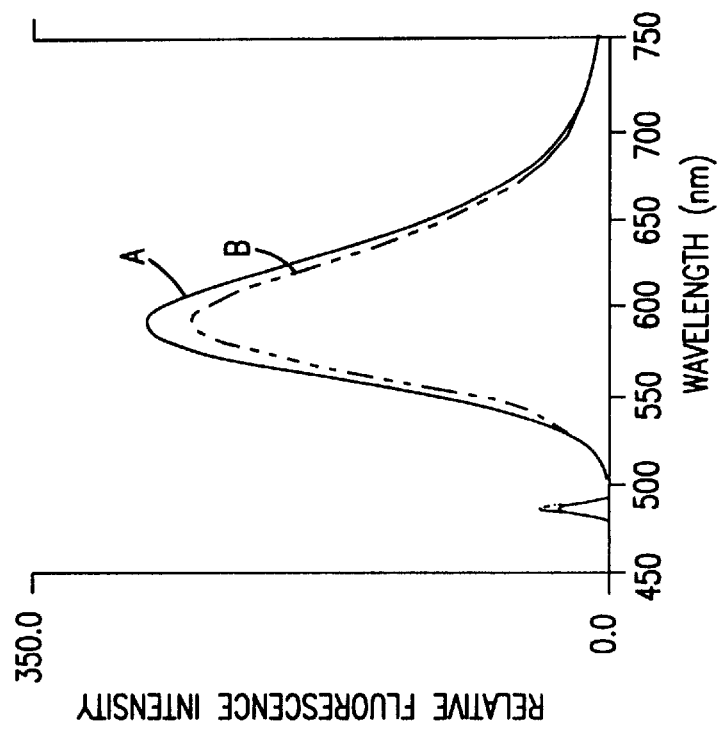

The relative photostability over 16 hours for polymeric dye 14D compared with that of phycoerythrin under the same conditions in ambient room light is shown in FIGS. 9A and 9B. In FIG. 9A, Curve A indicates the initial relative fluorescence intensity of polymeric dye 14D as a function of wavelength; Curve B indicates the relative fluorescence intensity of polymeric dye 14D as a function of wavelength 16 hours after the initial spectra were observed. In FIG. 9B, Curve A indicates the initial relative fluorescence intensity of phycoerythrin as a function of wavelength; Curve B indicates the relative fluorescence intensity of phycoerythrin as a function of wavelength 16 hours after the initial spectra were observed. FIGS. 9A and 9B indicate that polymeric dye 14D is more stable than phycoerythrin.

EXAMPLE VIII

Preparation Of Acrylic Acid Pyridinium Aniline Diene Polymer

Preparation Of Dye 5

Dye 5 was prepared by the condensation of Synthetic Intermediate VI with trans-4-(diethylamino)cinnamaldehyde in a procedure identical to that described in Example VI for the preparation of Dye 4, except that trans-4-(diethylamino)cinnamaldehyde was substituted for N,N-diethyl benzaldehyde. The procedure is illustrated in Scheme 13.

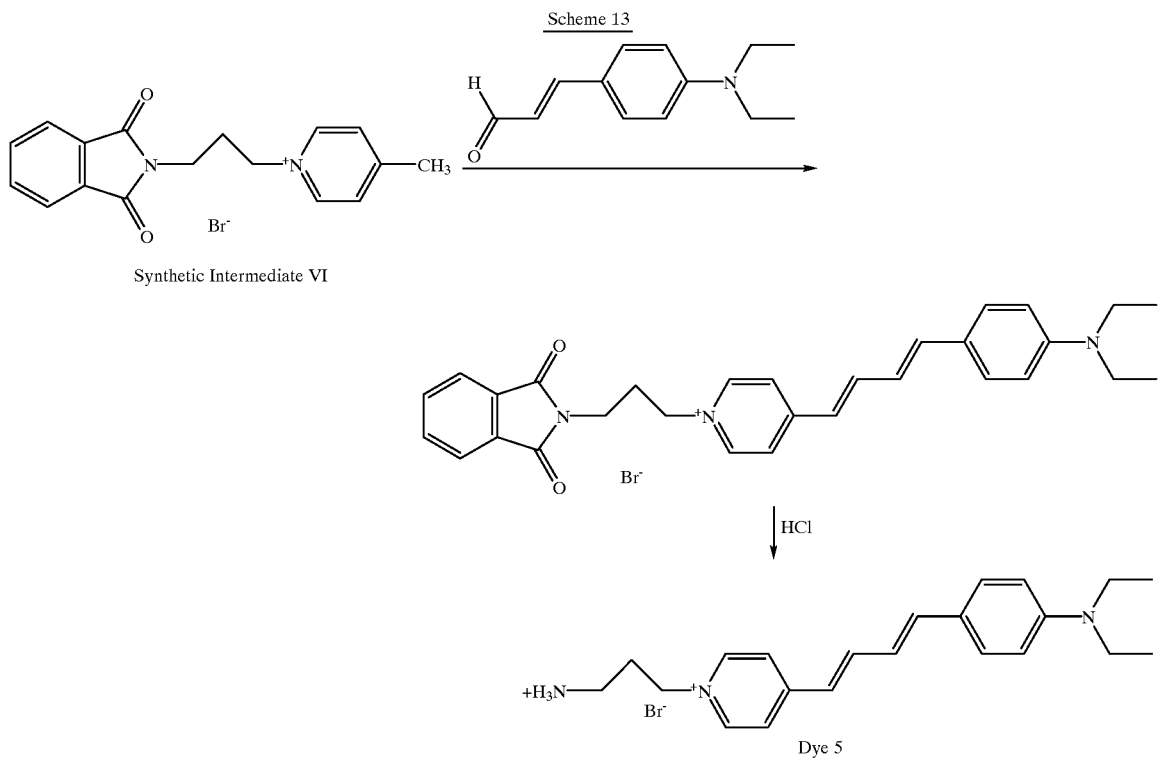

Dye 5 was purified by C-8 reverse phase HPLC using acetonitrile (25% by volume)/water (75% by volume) mobile phase.

Preparation Of Cyclodextrin Modified Acrylic Acid Pyridinium Aniline Diene Polymer (Polymeric Dye 18D)

Acrylic acid pyridinium aniline diene polymer can be prepared as described in Example VI, except that Dye 5 is substituted for Dye 4. This procedure is illustrated in Scheme 14.

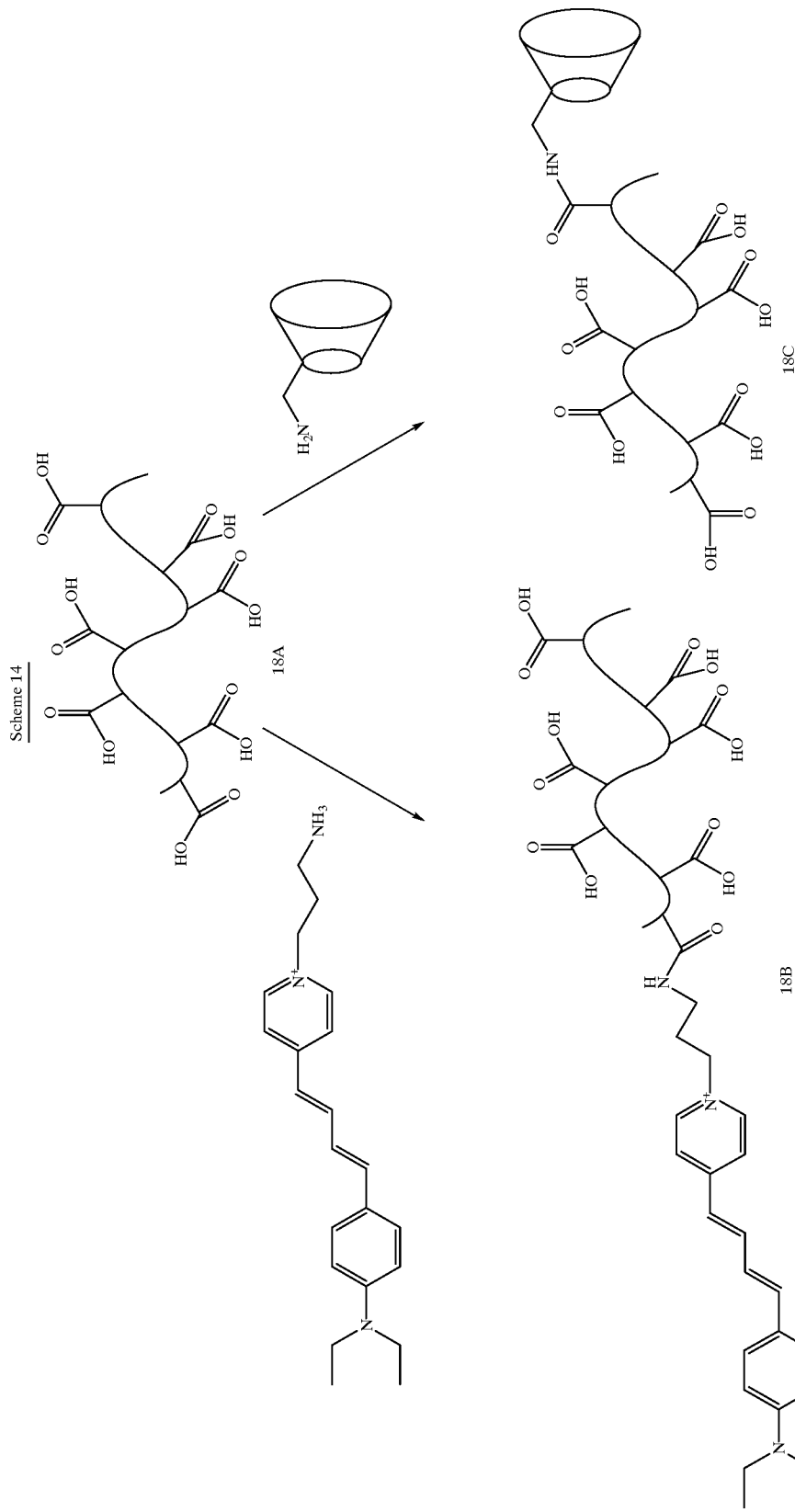

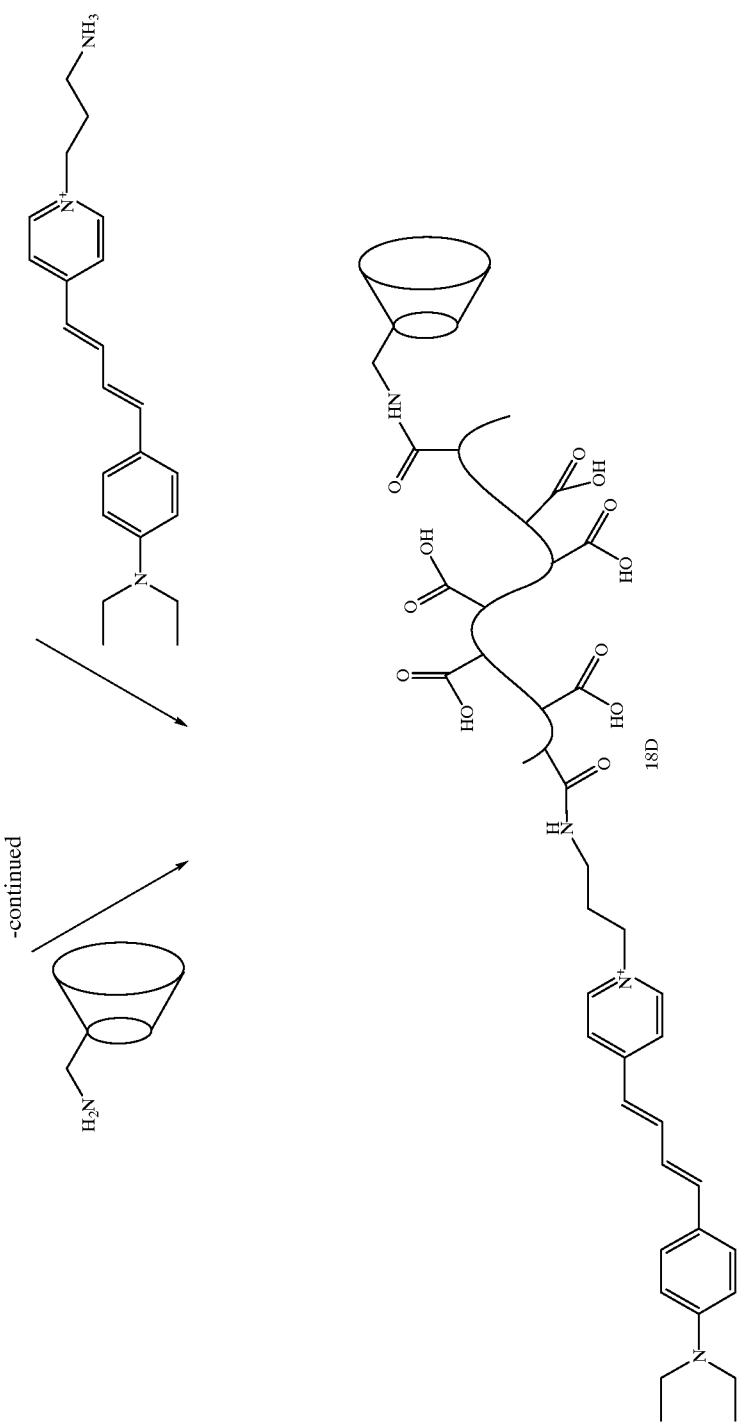

EXAMPLE IX

Conjugation Of Acrylamide Hydrazide Pyridinium Aniline Monoene Polymer To Anti-CD8 IgG Antibody A stock solution of polymeric dye 11D was prepared as described in Example I to give a concentration of 2.7 mg/mL. A stock solution of anti-CD8 IgG antibody was prepared in Buffer No. 2 at a concentration of 10 mg/mL. An aliquot containing 5.0 mg anti-CD8 IgG antibody was removed from the stock solution and concentrated to around 300 uL using a microconcentrator ("CENTRICON-30"). The concentrated material was then diluted with a buffer containing 50 mM triethanolamine, 160 mM NaCl, pH 8.0 (hereinafter "Buffer No. 3"). The final concentration of anti-CD8 IgG antibody was approximately 3 to 4 mg/mL.

A stock solution of sodium periodate in Buffer No. 3 was prepared at a concentration of 42.8 mg/mL. Approximately 120 $\mu$L of this stock solution was added to the anti-CD8 IgG antibody in triethanolamine buffer. The reaction mixture was incubated at a temperature of 2–8° C. in the dark while it was gently shaken with a mechanical shaker for one hour. The resultant oxidized IgG antibody was then purified by elution through a column (100–300 mesh, "SEPHADEX G-25") with Buffer No. 1. Fractions were assayed by ultraviolet spectroscopy (UV), and those void volume fractions with greater than 0.2 AU (blanked against the same Buffer No. 1) were pooled and concentrated to give a final volume of from 1 to 3 mg/mL.

Polymeric dye 11D was prepared by the reaction of polymeric dye 11B (0.24 mg/ml) with cyclodextrin aldehyde (6.0 mg/mL, prepared as described in *J Org. Chem.*, 1994, 59, 7511–7516). The progress of the reaction was monitored by size exclusion HPLC using a size exclusion column ("BIO-GEL TSK-50XL" or "BIO-SIL SEC-300") at a flow rate of 1.0 ml/minute in Buffer No. 2. Polymeric dye 11D, prepared as described in Example I, was then combined with the freshly prepared oxidized antibody. The molar ratios of polymeric dye 11D to IgG antibody antibodywere either 1.5/1.0 or 3.0/1.0. The yield of the bioconjugation was estimated by accurate injections of starting material stocks and reaction mixture on a size exclusion column ("BIO-SIL SEC-300" or "BIO-GEL TSK-50XL"). The resulting conjugate was then purified on a medium pressure column ("SEPHACRYL S-300") by elution with Buffer No. 2. The high molecular weight fractions were collected and concentrations estimated from ultraviolet spectra of the fractions. Fractions were tested in a flow cytometer for performance.

EXAMPLE X

Conjugation Of Acrylamide Hydrazide Pyridinium Aniline Monoene Polymer To Anti-CD8 IgG Antibody Alternatively, polymeric dye 11B can be conjugated to IgG antibody. The conjugate comprising polymeric dye 11B is used in place of a conjugate comprising polymeric dye 11D (see Example IX) and the former is then converted to the latter in situ by the addition of cyclodextrin aldehdye at a concentration of about 6 mg/ml. In the alternate method, the concentration of conjugate is from about 0.2 to about 0.4 mg/ml.

EXAMPLE XI

Conjugation Of Acrylamide Hydrazide Pyridinium Aniline Diene Polymer To Anti-Cd8 IgG Antibody Polymeric dye 12B was conjugated to IgG antibody in the following manner. IgG antibody was oxidized as described in Example IX. The IgG antibody was purified using a column ("SEPHADEX G-25") equilibrated with Buffer No. 1. The antibody was then diluted to a concentration of about 3.0 mg/ml (as determined by $A_{280}$ UV measurement). The IgG antibody was then exchanged into acetate buffer (pH 4.5, 0.1 N acetate, 0.1 N NaCl) (hereinafter "Buffer No. 4") using a microconcentrator ("CENTRICON-30"), with the final concentration being about 3.0 mg/ml. Polymeric dye 12B (prepared as described in Example IV) was then exchanged into acetate buffer (pH 5.5, 0.1 N acetate, 0.1 N NaCl) (hereinafter "Buffer No. 5") using a microconcentrator ("CENTRICON-30"). Finally, a portion (400 microliter, 1.2 mg) of antibody stock in Buffer No. 4 at a concentration of 3.0 mg/ml was added to a portion of polymeric dye 12B (1.5 ml, 4.5 mg) at a concentration of 3.0 mg/ml in Buffer No. 5. The resulting mixture was allowed to react overnight at a temperature of 2–8° C. with gentle shaking in the dark.

The resultant conjugate was then reacted with cyclodextrin aldehyde by adding sufficient cyclodextrin aldehyde to give a final concentration of 3.0 mg of cyclodextrin aldehyde per ml of buffer. The crude bioconjugate was then incubated overnight in the presence of cyclodextrin aldehyde and and purified using a column ("SEPHACRYL S-300").

EXAMPLE XII

Conjugation Of Acrylamide Hydrazide Pyridinium Aniline Diene Polymer To Anti-Cd8 IgG Antibody In an alternative embodiment, polymeric dye 12D was conjugated to IgG antibody in the following manner. Polymeric dye 12B was prepared as described in Example IV. Then, solid cyclodextrin aldehyde was added at a ratio of 1.5 mg cyclodextrin aldehyde for each 0.4 mg of polymeric dye 12B in 0.250 ml of Buffer No. 5. The cyclodextrin aldehyde and polymeric dye 12B reacted as the reaction mixture was stirred overnight at room temperature in the dark. The reaction product was purified by size exclusion chromatography ("SEPHADEX G-25") to yield polymeric dye 12D. Polymeric dye 12D was then reacted at a ratio of 3.0 equivalents of polymeric dye for each equivalent of IgG antibody as described in Example Xl using polymeric dye 12B. Bioconjugation was then followed by HPLC as described in Example XI. The resulting conjugate was purified using a size exclusion column ("SEPHACRYL S-300").

EXAMPLE XIII

Conjugation Of Acrylamide Hydrazide Benzothiazolium Aniline Monoene Polymer To IgG Antibody Polymeric dye 17D was prepared in the manner described in Example V. An aliquot of polymeric dye (3.0 ml, 1.0 mg of polymeric dye per 1.0 ml of solution) was removed from a stock solution of the polymeric dye in Buffer No. 2. Buffer No. 1 was used to exchange out Buffer No. 2 using a microconcentrator ("CENTRICON-30"). The concentration of the polymeric dye was then 2.36 mg/ml. The antibody was oxidized in the manner described in Example IX, and bioconjugation of polymeric dye 17D to IgG antibody was conducted in the manner described for polymeric dye 11D in Example XI.

Scheme 15 is a schematic diagram of the process for preparing the conjugate of this example.

Scheme 15

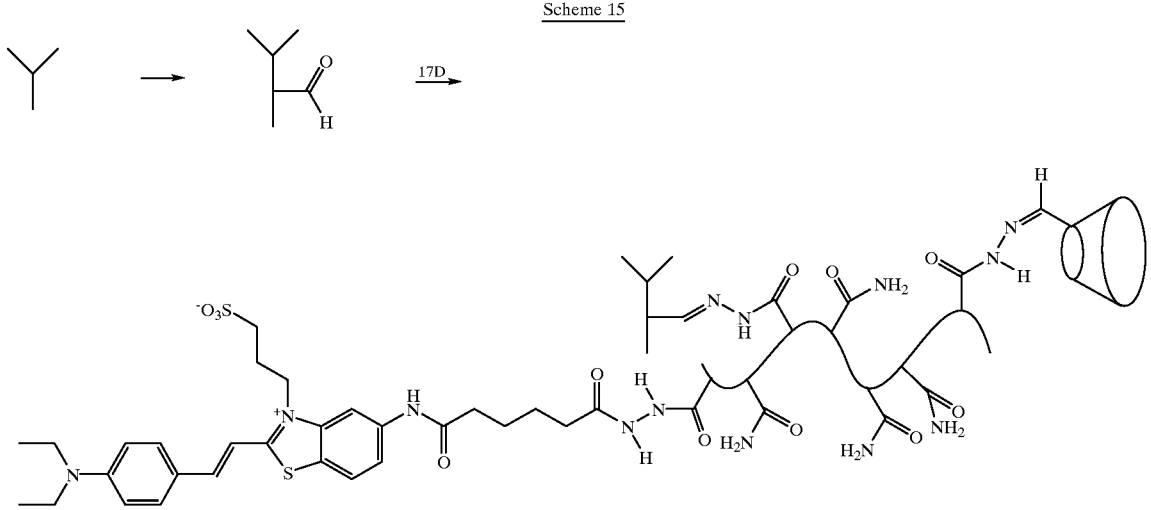

EXAMPLE XIV

Conjugation Of Thiolated Acrylic Acid Pyridinium Aniline Monoene Polymer To Maleimide Derivatized Anti-Cd4 IgG Antibody Preparation Of Thiophosphorylated Acrylic Acid Polymer Acrylic acid polymer (100 mg) was dissolved in deionized water (50 ml). Cystamine S-phosphate (1.6 mg, Aldrich Chemical Company) was added to the solution. Then five aliquots of EDAC (8.5 mg each) were added to the solution at ½ hour intervals over a several hour period as the solution was stirred continuously. The resulting product was purified by filtration purification ("CENTRIPREP-30"). A portion was dispensed, hydrolyzed, and assayed. Standard DTNB thiol assay methodology was used to determine that the portion was found to contain nine thiol groups per polymeric dye on the average.

Preparation of Cyclodextrin Modified Acrylic Acid Pyridinium Aniline Monoene Thiophosphorylated Polymer (Polymeric dye 15D)

Thiophosphate polymer (5.0 mg) was dissolved in of deionized water (1.0 mL). Next, Dye 4 (1.7 mg, prepared in the manner described in Example VI) and cyclodextrin amine 7 (12 mg, prepared as described in Example VI) were added to this solution. Five aliquots of EDAC (26 mg each) were added to the reaction mixture at ½ hour intervals. The material was then purified by centrifugation ("CENTRIPREP-30") and used for conjugation to IgG antibody.

Conjugation Of Polymeric Dye 15D To IgG Antibody

An aliquot of anti-CD4 IgG antibody (0.500 ml) was taken from a stock solution containing 4.0 mg antibody per 1.0 ml solution. The material was exchanged into Buffer No. 3 using a microconcentrator ("CENTRICON-30"). A second exchange was conducted to bring the IgG antibody back into Buffer No. 3. Oxidation was conducted by dissolving sodium periodate (42.8 mg) in Buffer No. 3 and adding 0.100 ml of this stock solution to the antibody to form a reaction mixture. The concentration of antibody for this reaction was at 1.0 mg/ml. The reaction mixture was incubated for one hour at a temperature of 2–8° C. The oxidized antibody was then purified using a column ("SEPHADEX G-25") equilibrated with Buffer No. 5. Fractions were collected and those void volume fractions containing AU readings of at least 0.1 at A280 were combined. Then the solution containing IgG antibody was concentrated to give a concentration of about 1.5 mg/ml.

Then, hydrazido maleimide M2C2H (0.369 mg, Pierce Chemical, catalogue #22304) was dissolved in Buffer No. 2 (0.100 ml) and added to the oxidized IgG antibody (about 2.0 mg IgG antibody). The mixture was then incubated at room temperature for two hours and gently shaken overnight at a temperature of about 2–8° C. The maleimide derivatized IgG antibody was then purified by size exclusion chromatography ("SEPHADEX G-25"), and the void volume fractions were combined.

The IgG antibody solution (1.7 mg) was first concentrated to around 0.3–0.4 ml and then diluted to 1.0 ml with pH 7.0 phosphate buffer with 0.1 mM $ZnCl_2$ and 1 mM $MgCl_2$ (hereinafter "Buffer No. 6"). An aliquot of alkaline phosphatase (0.005 ml of a 10 mg enzyme/ml stock concentration, Boehringer-Mannheim) was then added to this solution.

Next, polymeric dye 15D (2.55 mg) was diluted with deionized water (2.31 ml), and the resulting solution added to the maleimide derivatized IgG antibody/alkaline phosphatase system. The reaction mixture was incubated for 24 hours at a temperature of 2–8° C. in the dark with gentle shaking. Optionally, the remaining thiols can be capped with 100 equivalents of N-ethyl maleimide before purification. The reaction mixture was purified using a column ("SEPHACRYL S-300") with Buffer No. 2, and the conjugate was isolated from the void volume. The amount of conjugate was estimated from UV analysis or visual scoring. Analysis by HPLC indicated consumption of unconjugated IgG antibody.

Scheme 16 illustrates preparation of the bioconjugate of this example.

Scheme 16
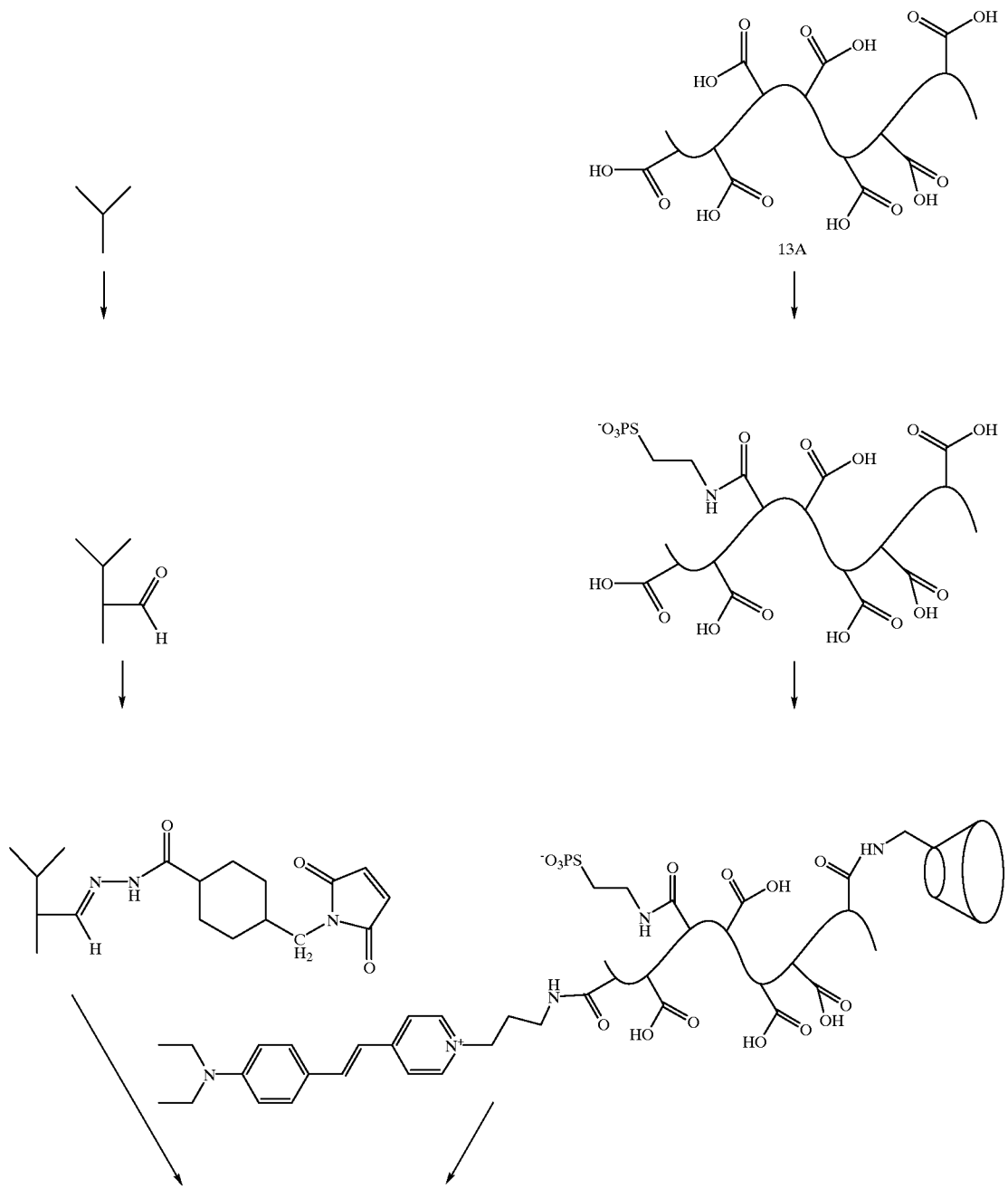

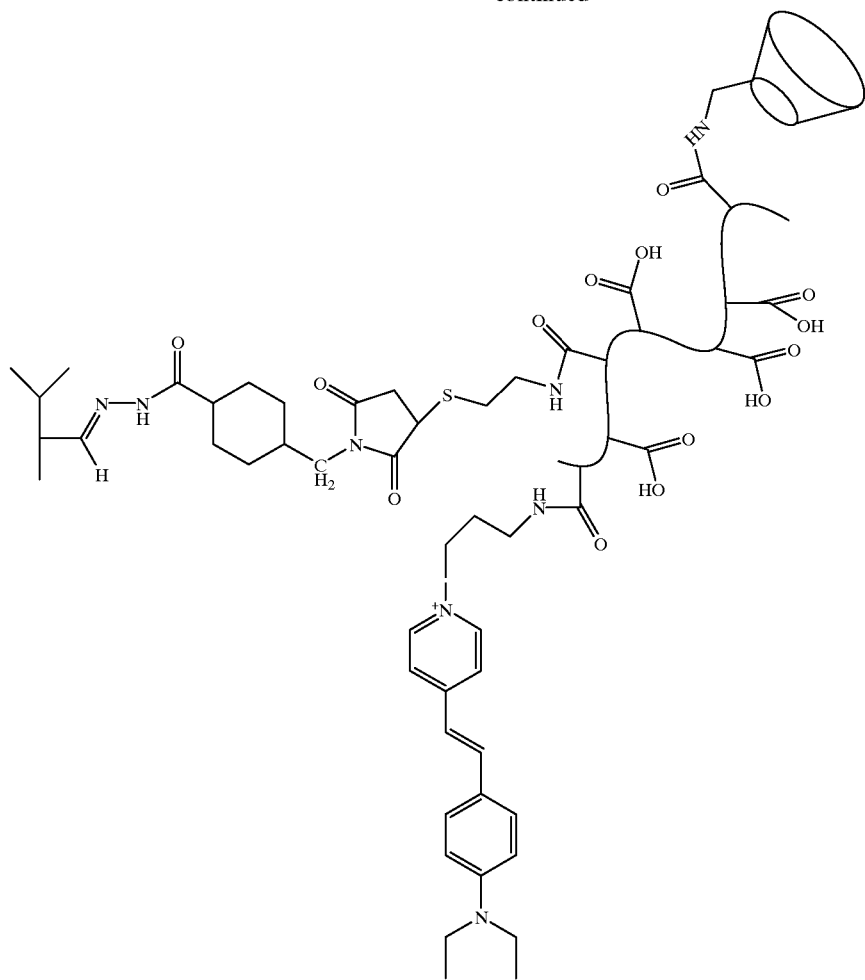

EXAMPLE XV

Conjugation Of Acrylic Acid Pyridinium Aniline Monoene Polymer To IgG Antibody Polymeric dye 13D was prepared in the manner described in Example VI. Polymeric dye 13D was then conjugated to IgG antibody in the following manner. Anti-CD4 IgG antibody was exchanged into pH 6.8 HEPES buffer (0.1 N HEPES) (hereinafter "Buffer No. 7") using a microconcentrator ("CENTRICON-30"). IgG antibody was then diluted with Buffer No. 7 to give a concentration of 1.0 mg antibody per ml. Polymeric dye 13D was then exchanged into deionized water using a microconcentrator ("CENTRICON-30") to a give a concentration of about 1.0 mg polymeric dye per ml. Then, sulfo-N-hydroxy-succinimide (0.0036 ml of a 30 mg/ml stock) in deionized water (0.108 mg) and EDAC (0.0039 ml of 50 mg/ml stock) in deionized water was added to polymeric dye 13D in deionized water to activate polymeric dye 13D for conjugation. Activated polymeric dye 13D in deionized water (1.8 ml, 1.8 mg) was mixed with IgG antibody (1.0 ml, 1.0 mg) in Buffer No. 7. The progress of the reaction was then monitored by size exclusion HPLC using a "BIO-GEL TSK-50XL" column with Buffer No. 1 as the mobile phase. The reaction product was then purified by size exclusion chromatography ("SEPHACRYL S-300") using Buffer No. 7 as the mobile phase.

Scheme 17 illustrates the procedure of this example.

Scheme 17

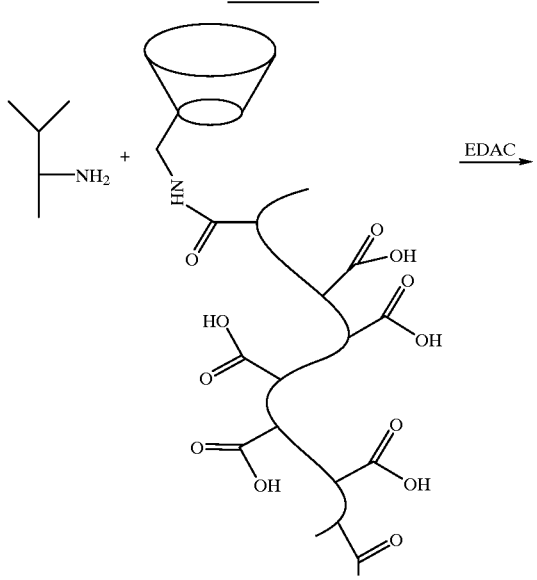

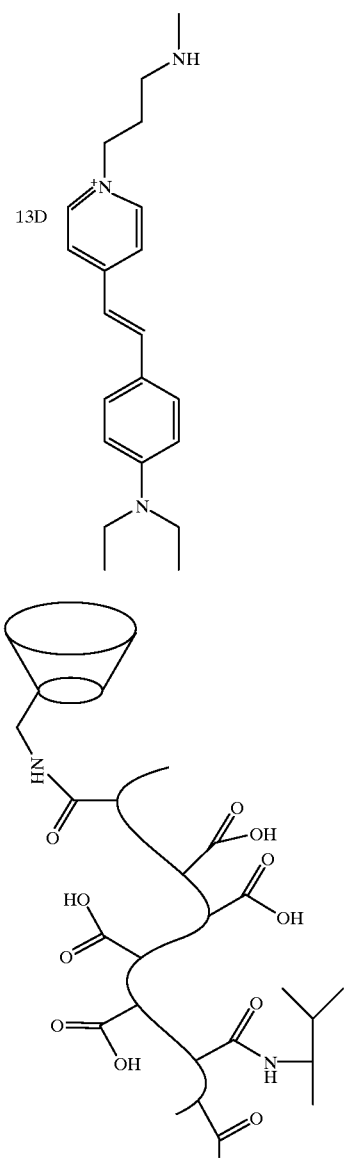

EXAMPLE XVI

Conjugation Of Maleime Conjugation Of Maleimide Derivatized Acrylic Acid Pyridinium Aniline Monoene Polymer To Thiolated IgG Antibody Acrylic acid polymer (100 mg) was dissolved in deionized water (5.0 mL) and reacted with hydrazidomaleimide linker M2C2H (15 mg, Pierce Chemical Co., Rockford, Ill.) by EDAC coupling. The coupling was effected by the addition of five aliquots of EDAC (15 mg each) over a two hour period at room temperature with stirring. The resultant maleimide derivatized polymer was purified by centrifugation ("CENTRIPREP-30").

To assay for maleimides, maleimide derivatized polymer 13A (1 mg) was dissolved in 1 mL of 100 mM phosphate buffer at pH 7.5. Cystaeamine.HCl (0.1 mg) was added to the solution, and the mixture allowed to incubate for one hour. Exactly 0.100 mL of the above mixture was diluted to 1 mL with phosphate buffer that contained 100 mM phosphate and 100 mM NaCl, pH 7.5 (hereinafter "Buffer No. 8"), and a standard DTNB assay for thiols was conducted. The solution adsorption was read at 412 nm and compared to the cysteamine/DTNB standard curve. Thus, the number of thiols that had been covalently bonded to the available maleimides could be indirectly determined from the difference observed.

The maleimide derivatized polymeric dye (5.0 mg) as prepared above was dissolved in deionized water (1.0 mL). Dye 4 (1.7 mg) and cyclodextrin amine 7 were then added to this solution. Finally, five aliquots of EDAC (26 mg each) were added at equal intervals over a two hour period. The resulting material was then purified by size exclusion chromatography ("SEPHADEX G-25").

Polymeric dye 16 was conjugated to thiolated IgG antibody in the following manner. Anti-CD4 IgG antibody (3.0 mg) was exchanged into Buffer No. 3 using a microconcentrator ("CENTRICON-30") and diluted to a final volume of 1.0 ml. Then NaIO4 (0.110 ml of 42.8 mg/ml stock solution) was added to this IgG antibody-containing solution, and the resulting solution incubated for one hour at a temperature of 2 to 8° C. The oxidized IgG antibody was then purified by gel filtration chromatography ("SEPHADEX G-25") with Buffer No. 2 as the eluant. The void volume fractions were then combined and concentrated to a volume of 0.086 ml to give a final concentration of IgG antibody of about 3.5 mg/ml.

Cystamine (0.250 ml of 170 mg/ml stock solution) in Buffer No. 3 was added to the freshly oxidized IgG antibody prepared as described above to form a reaction mixture. After the reaction mixture had been incubated for 15 minutes at ambient temperature, NaCNBH$_3$ (0.063 ml of 20 mg/ml stock solution) in Buffer No.3 was added to this mixture, and the resulting mixture incubated for about one hour at ambient temperature. The modified IgG antibody was then purified on a column ("SEPHADEX G-25") and the void volume fractions were concentrated using a microconcentrator ("CENTRICON-30"). The resultant disulfide-functionalized IgG antibody was then reduced by the addition of 0.050 ml of a 6.2 mg/ml stock solution of dithiothreitol in Buffer No. 2. After the mixture had been incubated at room temperature for 15 minutes, the reduced IgG antibody was purified by size exclusion chromatography ("SEPHADEX G-25"), and the void volume was pooled and concentrated using a microconcentrator ("CENTRICON-30"). The solution was diluted to about 0.30 mg/ml using 20 mM phosphate buffer, pH 7.0 (0.02 N phosphate, 0.02 N sodium chloride) (hereinafter "Buffer No. 9").

Polymeric dye 16D, prepared in the manner described above, was then exchanged into deionized water using a microconcentrator ("CENTRICON-30"), and then diluted to give a final concentration of 1.0 mg/ml. A portion of polymeric dye stock (0.500 ml, 0.5 mg polymer, 1 mg / ml) in deionized water was added to maleimide derivatized IgG antibody (1.0 ml, 0.3 mg/ml, 0.3 mg maleimide derivatized IgG antibody) in Buffer No. 9. The progress of the reaction was monitored by HPLC and consumption of IgG antibody was indicated by loss of area for the unmodified IgG peak. The mixture was fractionated by size exclusion chromatography ("SEPHACRYL S-300").

Scheme 18 illustrates the procedure of this example.

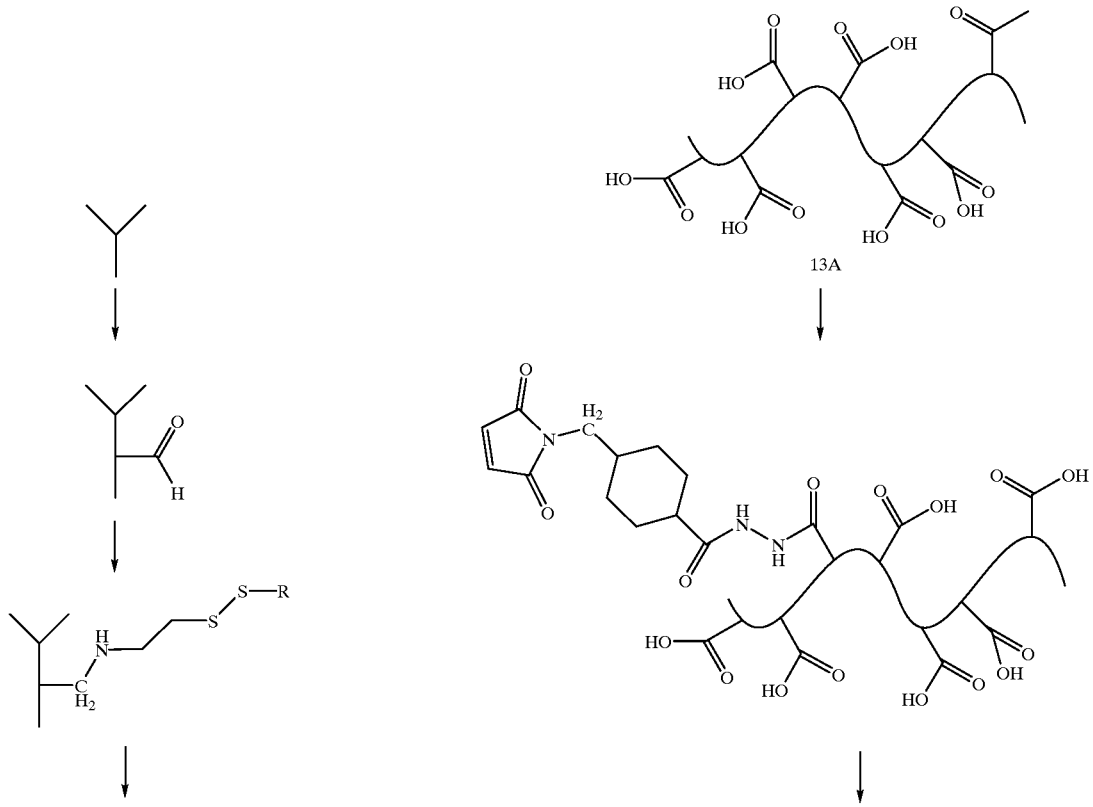

Scheme 18

-continued

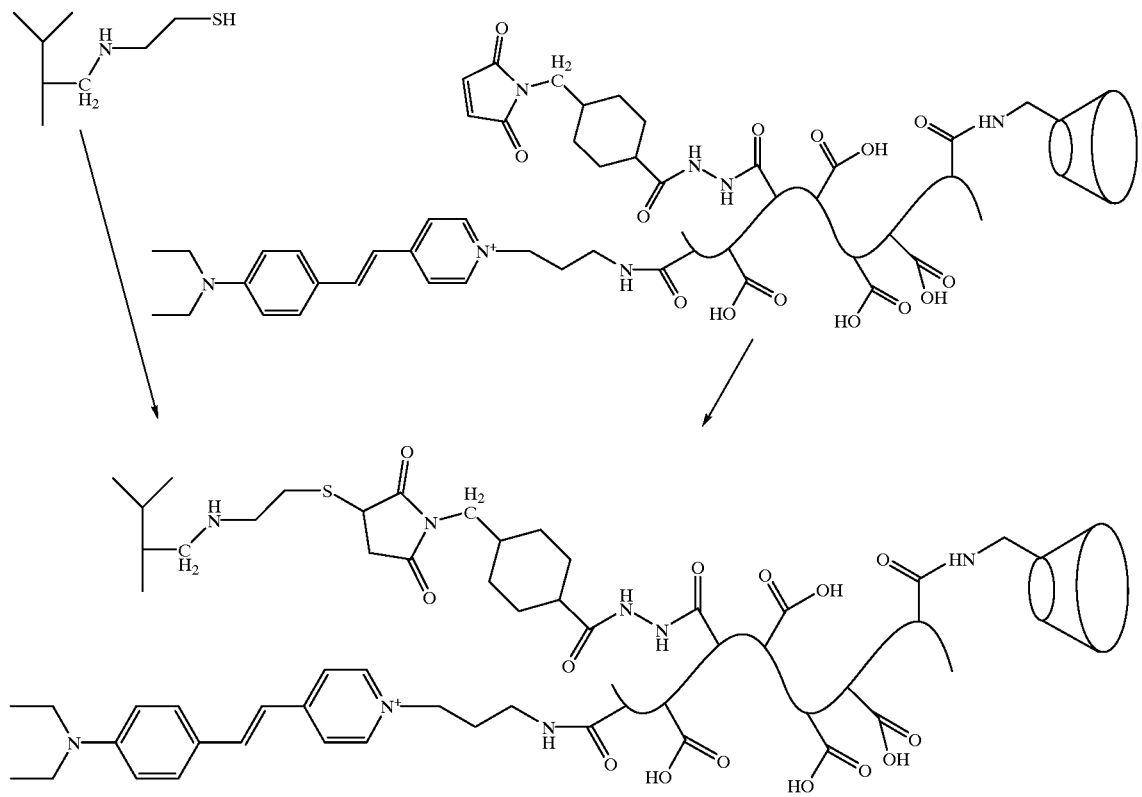

EXAMPLE XVII

Comparison Of Commercially Available Fluorescent Conjugates With Conjugates Of This Invention In this example, a flow cytometry format was used to make a comparison between the signals generated from commercially available or otherwise readily prepared fluorescent phycobiliprotein-based immunoconjugates and the synthetic polymeric fluorescent immunoconjugates as prepared in Example IX, X, and XI. The comparison was made between conjugates that are specific for lymphocyte markers CD4 or CD8.

Figure 10A:
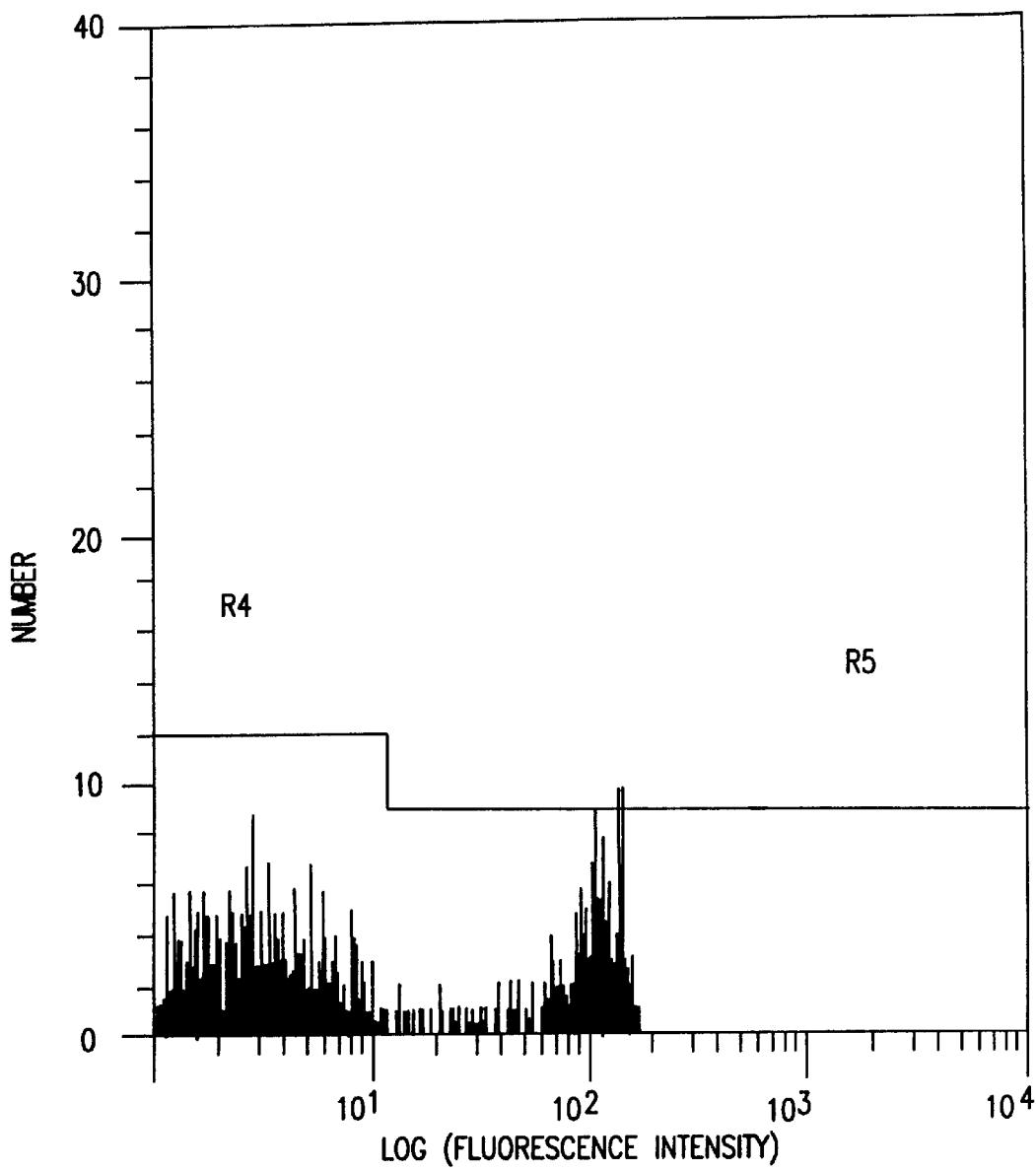
FIGS. 10A and 10B show the utility of a conjugate comprising polymeric dye 11D and IgG antibody in a flow cytometry assay. Both assays were performed using one microgram of conjugate and 10 mM dextran sulfate in the diluent.
Figure 10B:
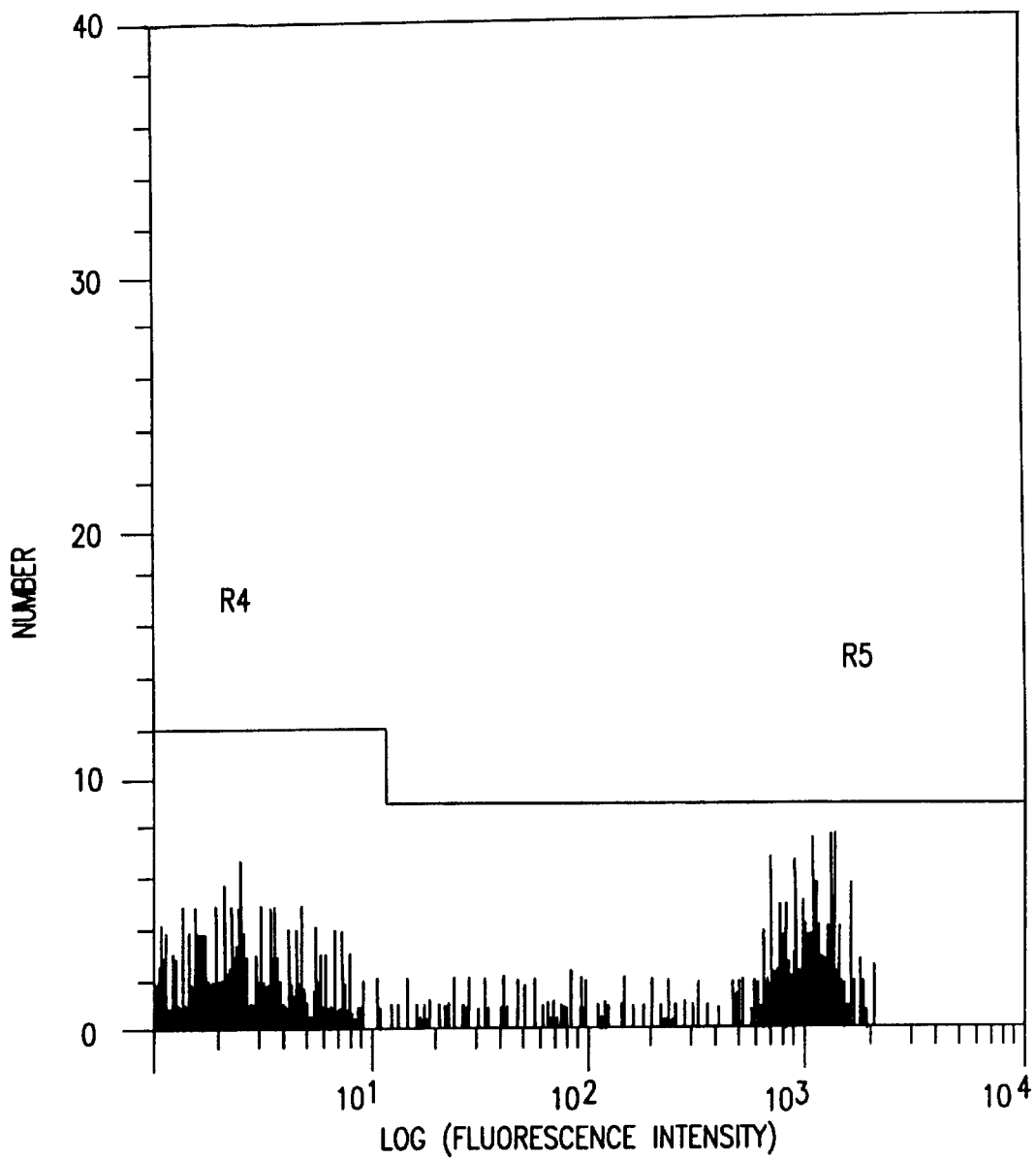
Figure 11A:
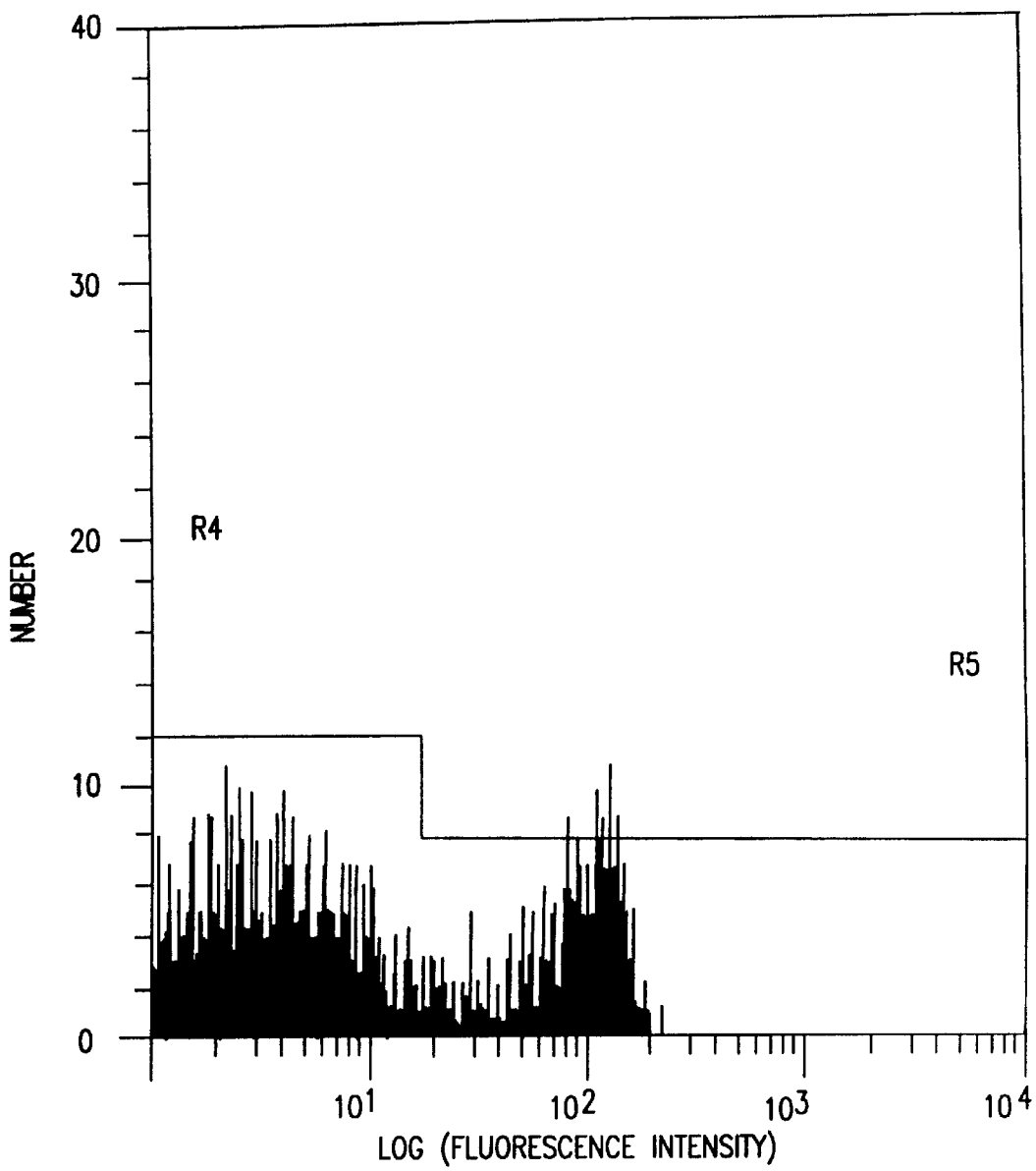
FIG. 11A and 11B show the utility of a conjugate comprising polymeric dye 11D and IgG antibody in a flow cytometry assay. Both assays were performed using one microgram of conjugate and 10 mM dextran sulfate in the diluent.
Figure 11B:
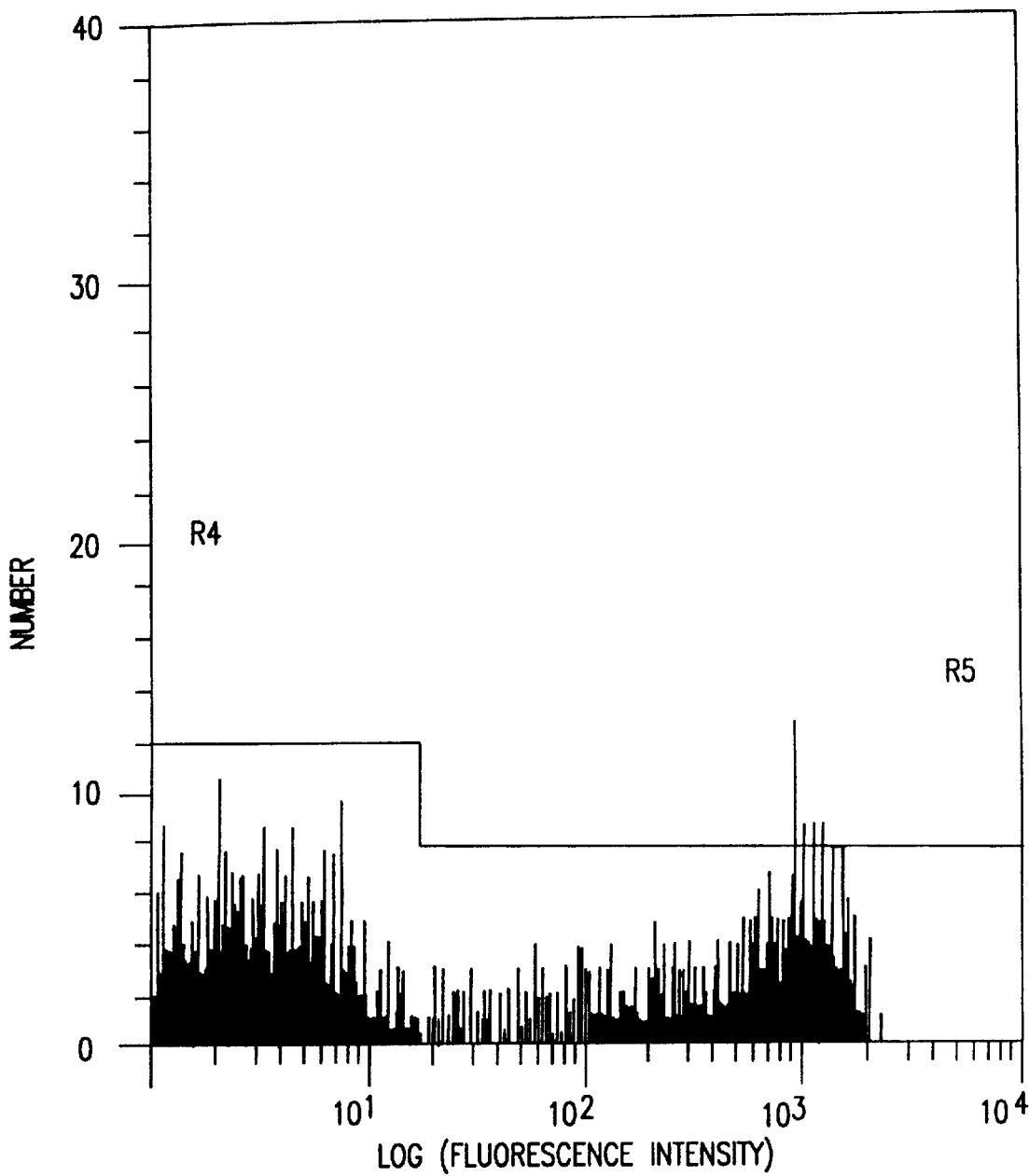
Figure 12A:
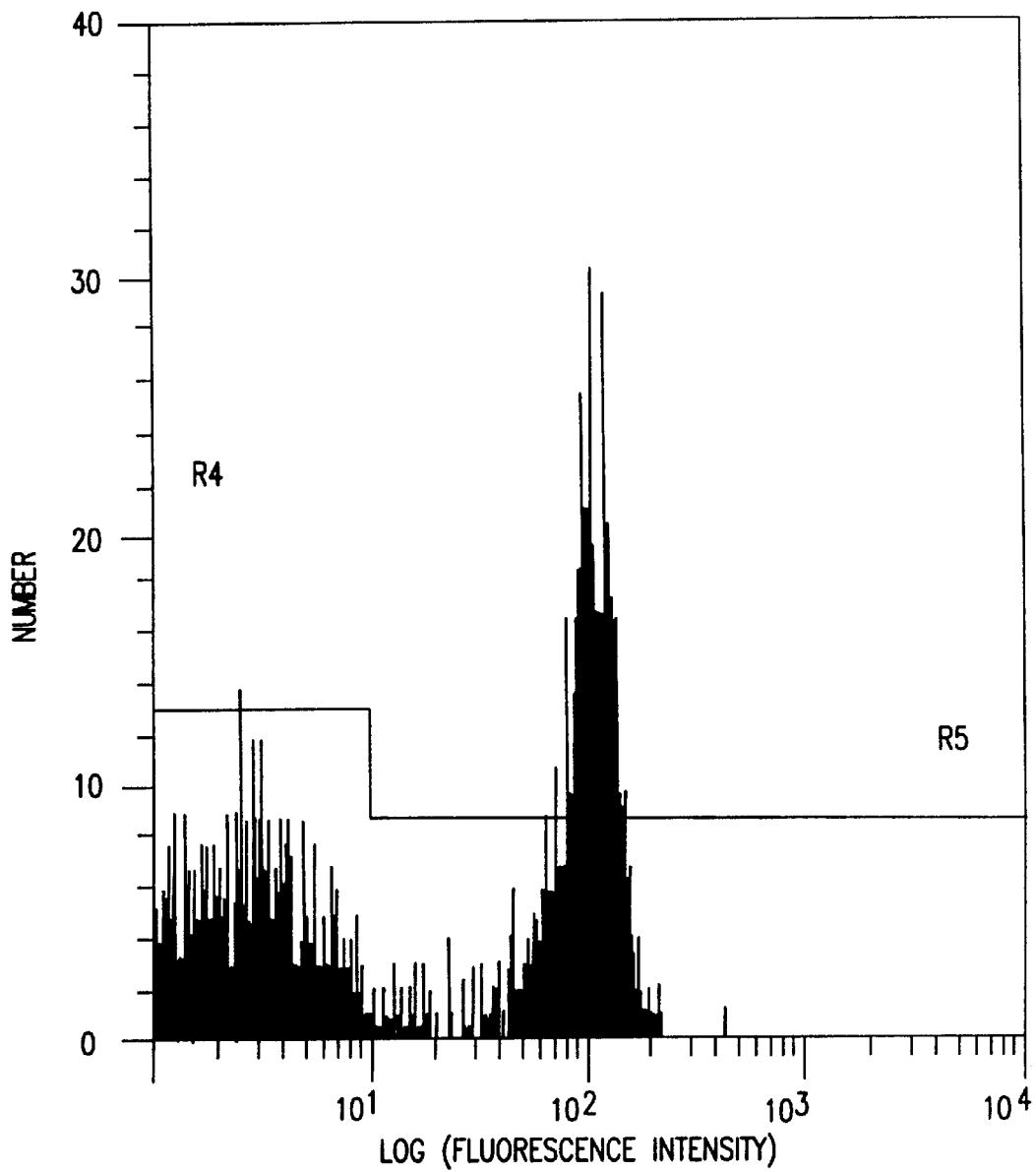
FIG. 12A and 12B show the utility of a conjugate comprising polymeric dye 11D and IgG antibody in a flow cytometry assay. Both assays were performed using one microgram of conjugate and 10 mM dextran sulfate in the diluent.
Figure 12B:
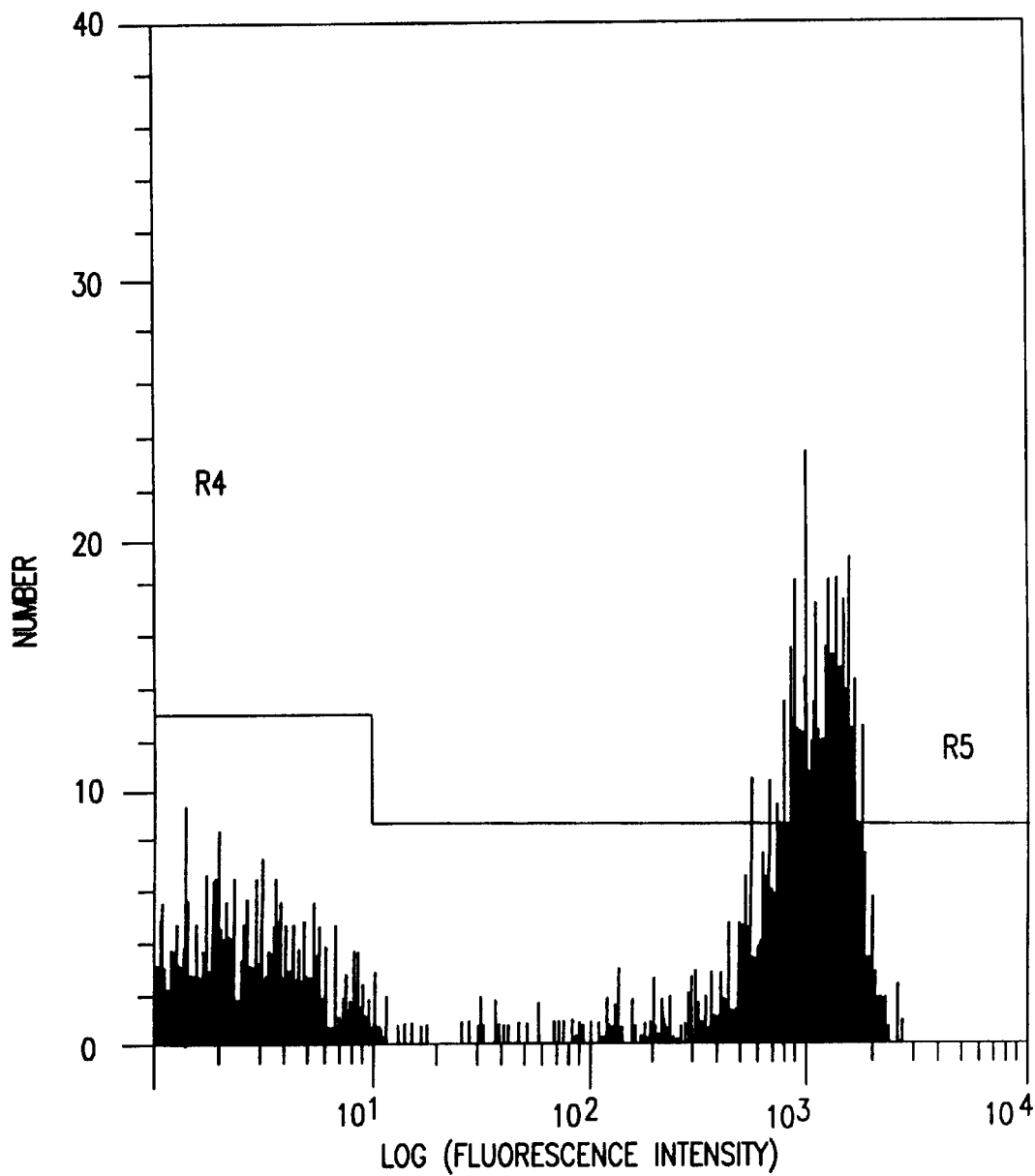

The results for the comparison of the conjugates derived from polymer 11D, prepared as described in Example IX, and phycoerthyrin conjugates derived from antibody with the same specificity are shown in FIGS. 10–12.

The conjugates of the anti-phycoerythrin were obtained from Coulter (Hialeah, Fla.) or derived from anti-CD8 antibody available from Coulter. Alternatively, anti-CD8 antibody can be obtained from Sigma Chemical Co. (St. Louis, Mo.) or DAKO Corporation (Copenhagen, Denmark). In another alternative embodiment, phycoerythrin (product #P-801) can be obtained from Molecular Probes (Eugene, Oreg.). SMCC and Traut's reagent can be obtained from Pierce (Rockford, Ill.). Thiolation of IgG antibody using Traut's reagent and maleimide derivatization of phycoerthyrin can be carried out using standard bioconjugation chemistry known to one of ordinary skill in the art. Purification and characterization of thiolated IgG antibody and maleimide derivatized phycoerythrin can be conducted using procedures known to one of ordinary skill in the art. Bioconjugation and purification of the thiolated IgG antibody and maliemide derivatized phycoerthrin can be conducted using methods known to one of ordinary skill in the art. Alternatively, the phycoerythrin can be derivatized with Traut's reagent and IgG antibody can be derivatized with maleimide using SMCC and the conjugation of the two entities can be carried out by methods known to one of ordinary skill in the art.

Figure 13A:
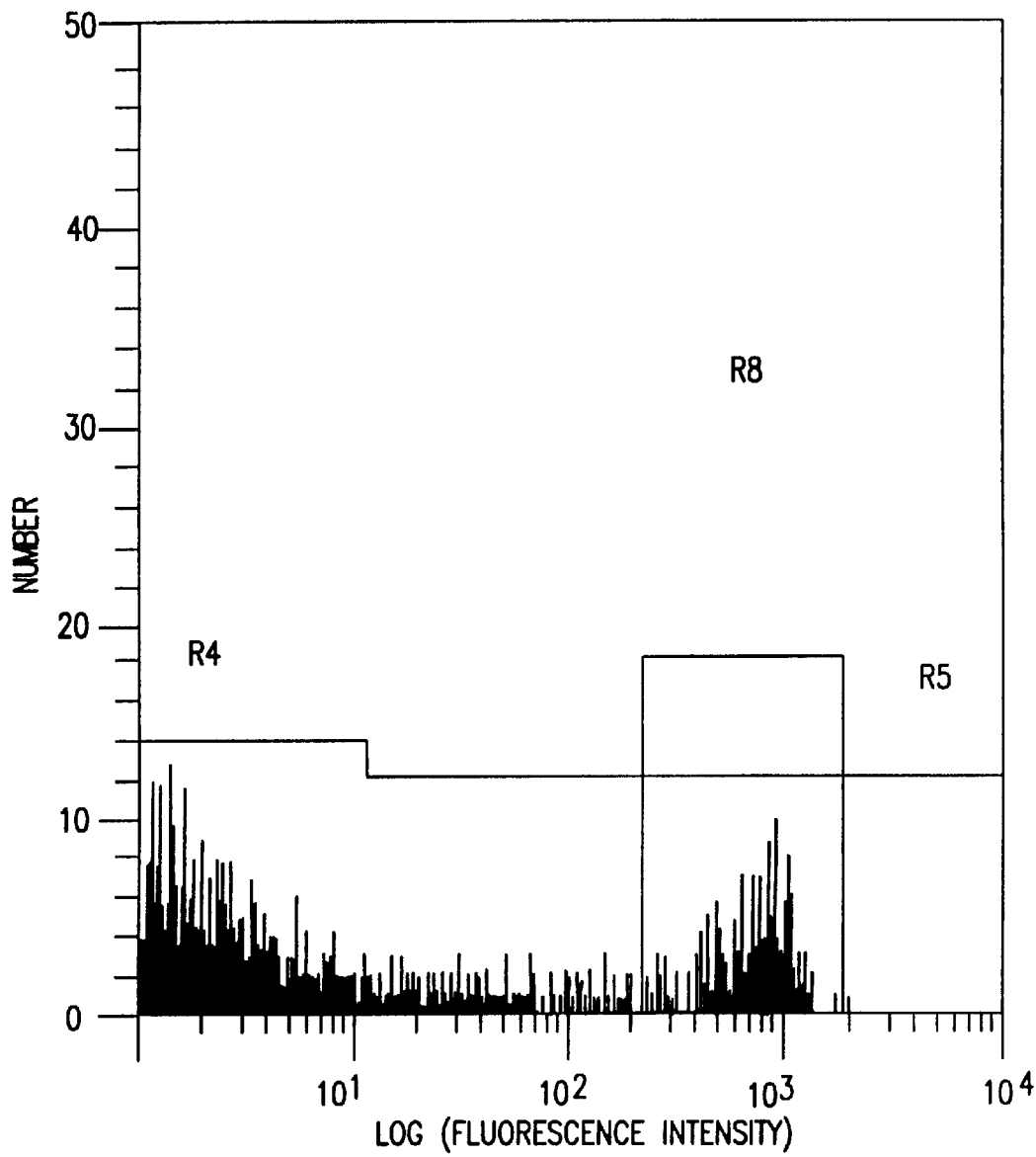
FIG. 13A and 13B compare performance of commercially available anti-CD8-phycoerythrin-cyanine tandem conjugates comprising anti-CD8 antibody and -phycoerythrin-cyanine dye (Dako) with a conjugate comprising anti-CD8 antibody and polymeric dye 12D for staining lymphocytes in flow cytometry.
Figure 13B:
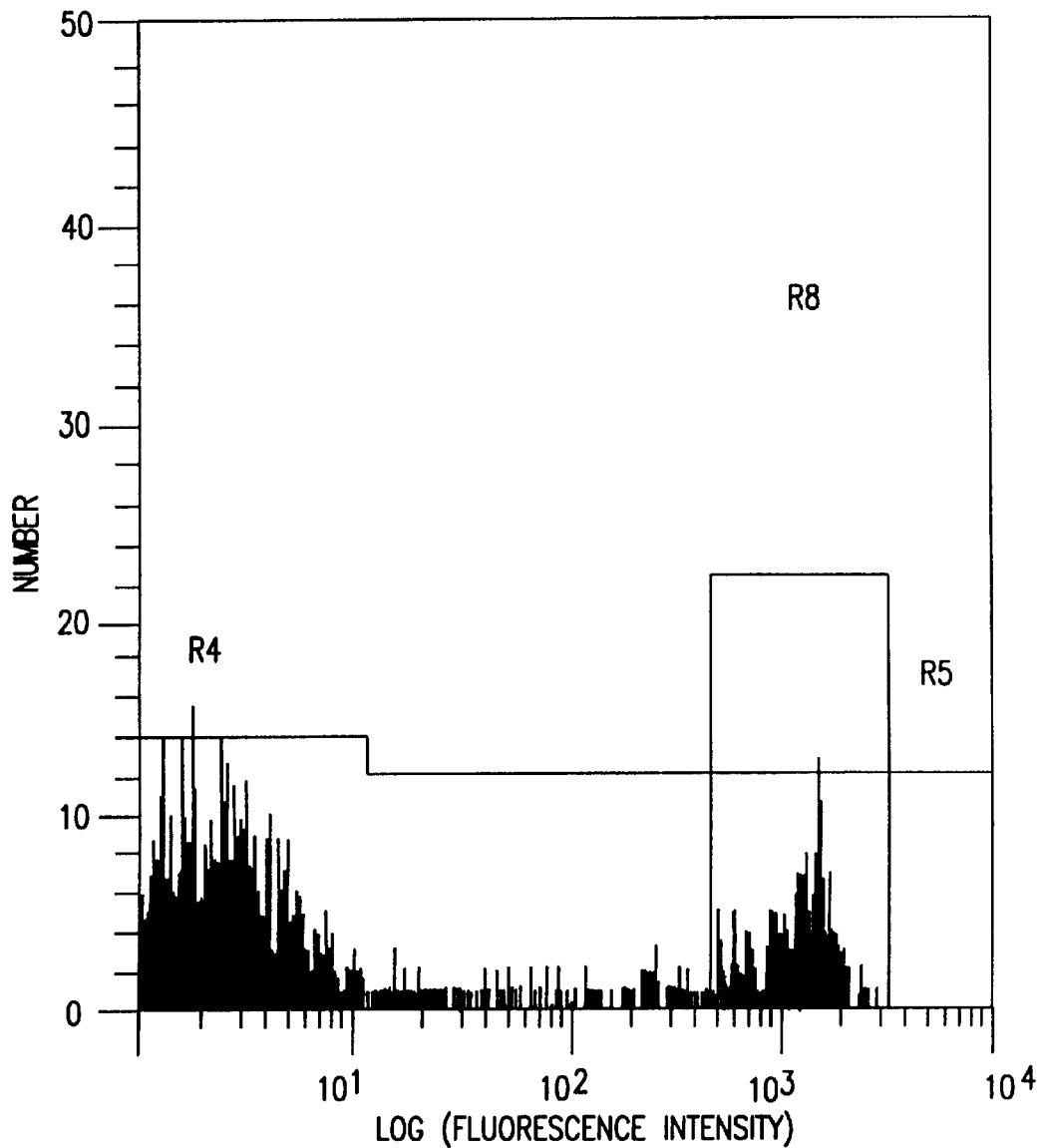
Figure 14:
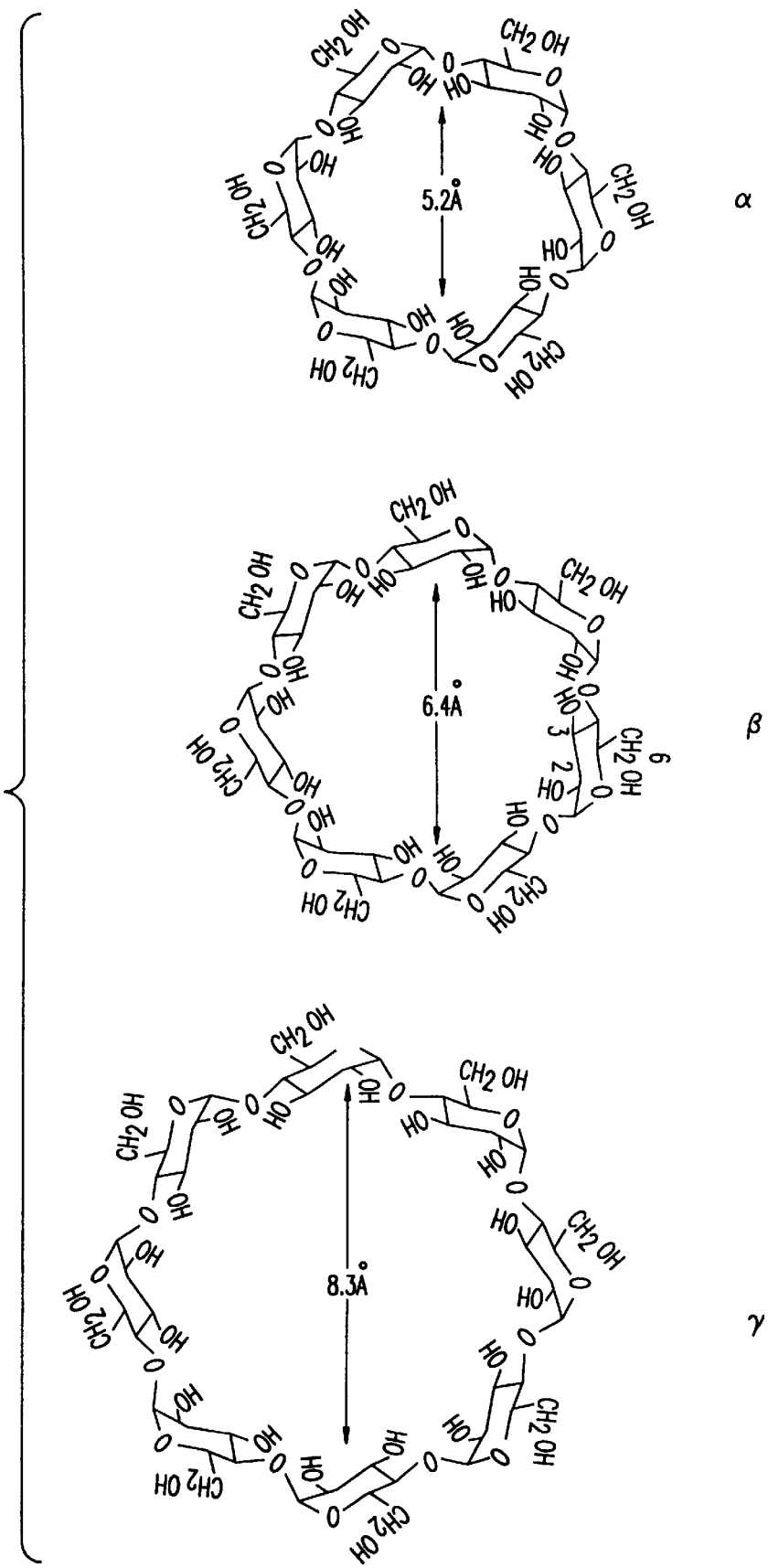
FIG. 14 shows alpha (α), beta (β), and gamma (γ) cyclodextrins and the system for numbering the glucose units therein.

The results for the comparison of the conjugates derived from polymer 12D, prepared as described in Example Xl, and phycoerythrin-cy5 conjugates derived from antibody with the same specificity are shown in FIG. 13.

Phycoerythrin-Cy5 conjugates were obtained by reacting phycoerythrin with Cy5 as follows. Reactive Cy5 (Biological Detection Systems, Pittsburgh, Pa.) was reacted with R-phycoerythrin (Molecular Probes Corporation, Eugene, Oreg.). Ratios of dye to phycoerythrin were calculated to be between 5:1 to 15:1.

Derivatization was accomplished using methods known to one of ordinary skill in the art. Purification was accomplished by methods such as gel filtration chromatography or centrifugal-based membrane concentration, which methods are known to one of ordinary skill in the art. Conjugation of the resultant phycoerythrin- Cy5 dye tandem to the anti-CD8 antibody was effected using methods known to one of ordinary skill in the art. A 30-atom linker, prepared as described in U. S. Pat. No. 5,002,883, incorporated herein by reference, was used to derivative the phycoerythrin-Cy5 tandem dye. Anti-CD8 antibody was thiolated using methods known to one of ordinary skill in the art. The thiolated anti-CD8 antibody and maleimide derivatized phycoerythrin-Cy5 were then conjugated and purified by size exclusion chromatography or other method known to one of ordinary skill in the art. Alternatively, SMCC can be used in place of the 30-atom linker. SMCC can be used to derivatize the phycoerythrin-Cy5 tandem by reaction with phycoerythrin-Cy5, followed by purification using column chromatography or other purification methods known to one of ordinary skill in the art.

Alternatively, phycoerythrin-Cy5-anti-CD8 conjugates can be obtained from Dako (Copenhagen, Denmark), Coulter (Hialeah, Fla.) or Sigma Chemical Company (St. Louis, Mo.). Alternatively, anti-CD8-Tricolor can be obtained from Caltag.

Other reagents used in this example included pH 7.0 phosphate buffered saline (PBS) having 0.1% sodium azide and 1.0% bovine serum albumin (BSA), which were added to the conjugates, and ammonium chloride lysing solution. The lysing solution was prepared as follows:

| Ingredient | Amount (g) |
|---|---|
| NH$_4$Cl | 8.26 |
| KHCO$_3$ | 1.0 |
| NaEDTA | 0.037 |

The ingredients listed above were dissolved in distilled water (1.0 liter) and the resulting solution was adjusted to a pH of 7.3 with HEPES buffer, which is commercially available from Sigma Chemical Co., St. Louis, Mo. The lysing solution was warmed to a temperature of 41° C. before use.

Protocol

The reagents were used directly to detect a specific cell surface receptor. The test tubes in which the tests were carried out contained the primary reagents in the amount of 5 μg. Fresh whole blood (200 μL) was then placed in each of the test tubes. Then the contents of each tube were gently vortexed and incubated at room temperature in the dark for 15 minutes. After incubation, the tubes were washed once in 3 ml of the modified PBS. The washed tubes were then centrifuged for 3 minutes at 500× gravity, the supernatants from these tubes were then aspirated, and the cell pellets were resuspended in the modified PBS.

After incubation, the tubes were treated with ammonium chloride lysing solution according to the following protocol.

1. 3.0 ml of the lysing solution was added to each tube.
2. The contents of each tube were thoroughly mixed by a disposable pipette.
3. The contents of each tube were incubated at room temperature for 7 minutes.
4. The contents of the tubes were centrifuged for 3 minutes at 2000 rpm.
5. All but 100 μL of the supernatants from each tube were aspirated.
6. The contents of the tubes were vortexed to resuspend the pellets.
7. 3.0 ml of PBS having 0.1% sodium azide and 1.0% BSA was then added to the resuspended pellets.
8. Steps 4–7 were repeated.
9. 0.5 ml of PBS having 0.1% sodium azide and 1.0% BSA was then added to the resuspended pellets. The PBS also contained 10 mM (60 mg/ml) pentosan-polysulfate (Sigma Chemical Company (P8275) ) adjusted to pH 7.5.

The contents of each tube was analyzed using a Facscan II fluorescence activated cell sorter available from Becton-Dickinson Inc. The instrument settings were optimized for visualization on lymphocytes, monocytes, and granulocytes on forward verse side scatter parameters. "Quick Cal" beads (available from Flow Cytometry Standards Corporation, Durham, N.C.) were run, as instructed by the accompanying software program, in order to generate a calibration curve. The percent fluorescent events on the histogram was determined for each tube using the three light scatter gates.

Results

The results of these experiments are shown in FIGS. 10, 11, and 12 for anti-CD8/phycoerythrin and the anti-CD8-pyridinium aniline monoene conjugate of Example IX, and in FIG. 13 for the anti-CD8/phycoerythrin-cyanine and the anti-CD8-pyridinium aniline diene conjugate of Example X. The conjugates of the present invention provided adequate resolution of labeled and unlabeled lymphocytes and provided resolution results comparable to those of commercially available conjugates.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A polymeric dye comprising:

(a) a nucleophilic polymeric entity; and (b) covalently bonded to said nucleophilic polymeric entity a plurality of electrophilic signal-generating groups, wherein said electrophilic signal-generating groups are derived from a dye having at least one anilino moiety coupled to a heterocyclic moiety containing at least one nitrogen atom in the heterocycle by means of an ethylenically unsaturated linking group, said polymeric dye having hydrophobic and conformationally restricting moieties associated therewith, said signal-generating groups containing carboxylic groups, wherein said signal-generating groups are derived from a dye having the following structure:

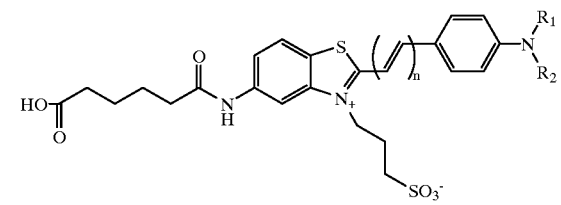

where $R_1$ represents an alkyl group and $R_2$ represents an alkyl group and n represents an integer from 1 to 3, inclusive.

2. A polymeric dye comprising:

(a) a nucleophilic polymeric entity; and (b) covalently bonded to said nucleophilic polymeric entity a plurality of electrophilic signal-generating groups, wherein said electrophilic signal-generating groups are derived from a dye having at least one anilino moiety coupled to a heterocyclic moiety containing at least one nitrogen atom in the heterocycle by means of an ethylenically unsaturated linking group, said polymeric dye having hydrophobic and conformationally restricting moieties associated therewith, said signal-generating groups containing carboxylic groups, wherein said signal-generating groups are derived from a dye having the following structure:

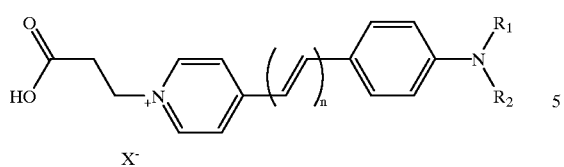

where $R_1$ represents an alkyl group and $R_2$ represents an alkyl group and n represents an integer from 1 to 3, inclusive, and $X^-$ represents a negatively charged counterion.

3. A conjugate comprising;

a member of a binding pair;

at least one polymeric dye bonded to said member; and hydrophobic and conformationally restricting moieties associated with said polymeric dye, wherein said polymeric dye comprises a benzothiazole pyridinium triene of the formula:

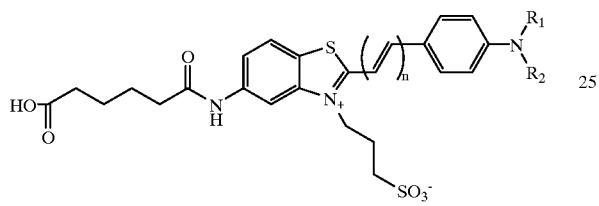

where $R_1$ represents an alkyl group and $R_2$ represents an alkyl group and n represents an integer from 1 to 3, inclusive.

4. A conjugate comprising;

a member of a binding pair;

at least one polymeric dye bonded to said member; and hydrophobic and conformationally restricting moieties associated with said polymeric dye, wherein said polymeric dye comprises an aminosytryl pyridinium of the formula:

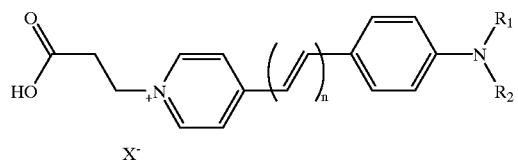

where $R_1$ represents an alkyl group and $R_2$ represents an alkyl group and n represents an integer from 1 to 3, inclusive, and $X^-$ represents a negatively charged counterion.

* * * * *